(12) United States Patent
Wuttke et al.

(10) Patent No.: US 12,138,381 B2
(45) Date of Patent: Nov. 12, 2024

(54) NEBULIZER AND CARTRIDGE

(71) Applicant: Boehringer Ingelheim International GmbH, Ingelheim am Rhein (DE)

(72) Inventors: Gilbert Wuttke, Ingelheim am Rhein (DE); Herbert Graessl, Murrhardt (DE)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 865 days.

(21) Appl. No.: 16/954,121

(22) PCT Filed: Dec. 18, 2018

(86) PCT No.: PCT/EP2018/085552
§ 371 (c)(1),
(2) Date: Jun. 15, 2020

(87) PCT Pub. No.: WO2019/121722
PCT Pub. Date: Jun. 27, 2019

(65) Prior Publication Data
US 2021/0146066 A1    May 20, 2021

(30) Foreign Application Priority Data
Dec. 21, 2017  (EP) ..................... 17020588

(51) Int. Cl.
*A61M 11/02*     (2006.01)
*A61M 15/00*     (2006.01)
(52) U.S. Cl.
CPC ........ *A61M 11/02* (2013.01); *A61M 15/0013* (2014.02); *A61M 15/0025* (2014.02)
(58) Field of Classification Search
CPC .............. A61M 11/02; A61M 15/0013; A61M 15/0025; A61M 2205/128; A61M 16/208; A61M 15/0065; A61M 11/06; B05B 11/026; B05B 11/1091; B05B 11/0054; B05B 15/33
See application file for complete search history.

(56) References Cited

U.S. PATENT DOCUMENTS

| | | | |
|---|---|---|---|
| 4,245,788 A | 1/1981 | Wright |
| 5,370,272 A | 12/1994 | Gueret |
| 5,497,944 A | 3/1996 | Weston |
| 5,642,838 A | 7/1997 | Stoody |

(Continued)

FOREIGN PATENT DOCUMENTS

| | | |
|---|---|---|
| CA | 2319834 A1 | 9/1999 |
| EP | 1312418 A2 | 5/2003 |

(Continued)

OTHER PUBLICATIONS

International Search Report and Written Opinion for corresponding PCT Application No. PCT/EP2018/085552, 19 pages, dated May 28, 2019.

*Primary Examiner* — Justine R Yu
*Assistant Examiner* — Matthew R Moon
(74) *Attorney, Agent, or Firm* — Matthew B. Dernier, Esq.

(57) ABSTRACT

A cartridge and a nebulizer for nebulizing a fluid as well as a method for fluidically connecting the cartridge to the nebulizer are proposed. The cartridge comprises a closure with a valve, wherein the valve displaces fluid into the nebulizer when opened. Further, the cartridge forms two axially spaced sealings with the nebulizer when connected.

42 Claims, 24 Drawing Sheets

(56) References Cited

U.S. PATENT DOCUMENTS

| | | | |
|---|---|---|---|
| 5,992,692 | A | 11/1999 | Boissay |
| 6,412,659 | B1 | 7/2002 | Kneer |
| 6,988,496 | B1 | 1/2006 | Eicher |
| 7,341,208 | B2 | 3/2008 | Joachim |
| 8,734,392 | B2 * | 5/2014 | Stadelhofer ......... B05B 11/0027 128/200.14 |
| 9,623,200 | B2 * | 4/2017 | Holakovsky ........... A61M 11/02 |
| 9,757,750 | B2 | 9/2017 | Holakovsky |
| 10,016,568 | B2 * | 7/2018 | Bach ................... B05B 11/0054 |
| 11,033,920 | B2 * | 6/2021 | Toh .................... B05B 11/0054 |
| 2003/0209238 | A1 | 11/2003 | Joachim |
| 2004/0015126 | A1 | 1/2004 | Zierenberg |
| 2006/0016449 | A1 | 1/2006 | Eicher |
| 2007/0090205 | A1 | 4/2007 | Kunze |
| 2008/0029099 | A1 | 2/2008 | Storz |
| 2008/0245758 | A1 | 10/2008 | Geser |
| 2008/0257915 | A1 | 10/2008 | Wold |
| 2010/0300441 | A1 | 12/2010 | Von Schuckmann |
| 2011/0168175 | A1 | 7/2011 | Dunne |
| 2012/0132198 | A1 * | 5/2012 | Hausmann ............. A61M 11/06 128/200.14 |
| 2012/0325204 | A1 * | 12/2012 | Holakovsky ........ B05B 11/0054 128/200.23 |
| 2015/0320948 | A1 | 11/2015 | Eicher |
| 2017/0203056 | A1 | 7/2017 | Dunne |

FOREIGN PATENT DOCUMENTS

| | | |
|---|---|---|
| EP | 2614848 A1 | 7/2013 |
| GB | 2144997 A | 3/1985 |
| WO | 0049988 A2 | 8/2000 |
| WO | 2004062813 A1 | 7/2004 |
| WO | 2005063591 A1 | 7/2005 |
| WO | 2006136426 A1 | 12/2006 |
| WO | 2009103510 A1 | 8/2009 |
| WO | 2009115200 A1 | 9/2009 |
| WO | 2010094305 A1 | 8/2010 |
| WO | 2012130757 A1 | 10/2012 |
| WO | 2012162305 A1 | 11/2012 |
| WO | 2015178914 A1 | 11/2015 |

* cited by examiner

NEBULIZER AND CARTRIDGE

BACKGROUND

The present invention relates to a cartridge for a nebulizer, to a nebulizer, and to a method.

WO 00/49988 A2 relates to a cartridge that can be detachably connected to a withdrawing device, in particular an atomizer for generating an aerosol which can be inhaled and which is provided for treating illnesses. The cartridge is suited for aqueous and alcoholic liquids which contain a pharmacologically active ingredient. The cartridge is a container which can comprise a collapsible bag containing the fluid, a dimensionally stable container and a stiff metal shell. The dimensionally stable container can have an opening which is closed by a closure comprising an insertion port. A withdrawal element of the withdrawal device can be inserted into the cartridge via the insertion port for withdrawal of fluid. The insertion port can be closed by a membrane initially which can be pierced by the withdrawal element upon insertion. The membrane prevents leaking of liquid while storing the cartridge.

WO 2009/103510 A1 and WO 2010/094305 A1 disclose a device and a cartridge for dispensing a liquid, preferably a drug. The liquid is pressurized in the cartridge to a first lower pressure and, then, pressurized in doses by a pump to a second higher pressure. A valve arranged between cartridge and the pump is normally closed and/or opened only temporarily.

WO 2012/130757 A1 relates to a hand-held device, in particular an atomizer, for discharging a liquid pharmaceutical preparation from a container having a container cap. The pharmaceutical preparation can, for example, be based on an alcoholic solvent. The atomizer having the inserted container comprises a sealing system composed of two seals at the connecting site between the device and the container which prevent loss of liquid, diffusion leaks and gas exchange with the surroundings at this site.

WO 2005/063591 A1 relates to an inhaler which can dispense a pharmaceutical liquid as an aerosol for inhalation. The inhaler comprises an insertable cartridge containing the fluid, a housing for receiving the cartridge and a pressure generator with a drive spring in order to pressurize a dose of the fluid to be dispensed. When mounting the cartridge to the inhaler, a device is pushed into the liquid to displace a respective volume of liquid from the cartridge into a liquid conducting system of the inhaler.

US 2012/0132198 A1 relates to a reservoir comprising a closure for a fluid chamber with a medicament formulation and a nebulizer having such a reservoir. The closure is formed by two closure members welded together.

GB 2 144 997 A relates to a dosage inhalator comprising a dosing unit for dosing a pharmacologically active compound, a propellant container containing a liquid or gaseous propellant and a propellant dispensing unit. The propellant container comprises a valve which is normally closed and opened only temporarily for filling a chamber of the propellant dispensing unit with propellant.

U.S. Pat. No. 5,497,944 A relates to a metered dose inhaler for dispensing a fluid medicament. A liquid drug is contained in a reservoir, and metered quantities of the drug are presented into a pressure chamber and subsequently pressurized for atomization. The flow of liquid through the device is controlled by non-return valves. The reservoir can comprise such a non-return valve, allowing liquid flow only out of the reservoir and into the pressure chamber.

SUMMARY

It is an object of the present invention to provide a cartridge for a nebulizer, a nebulizer comprising a cartridge and a method for fluidically connecting a cartridge to a nebulizer, wherein a simple construction of the cartridge or its closure, an improved sealing, a secure fluid connection of the cartridge with the nebulizer and/or a simple operation is enabled or supported.

The present invention relates to a nebulizer/dispensing device for nebulizing/dispensing of a fluid, preferably a liquid, in particular a liquid pharmaceutical composition/formulation and/or liquid medicament from a preferably replaceable cartridge containing the fluid, and further relates to the cartridge of such a nebulizer/dispensing device.

Mostly preferred, the fluid is aqueous and/or comprises an aqueous solution and/or water as a solvent. Alternatively, the fluid may comprise an alcoholic solution and/or an alcohol, in particular ethanol, as solvent.

The cartridge comprises preferably a container and/or a bag containing the fluid, in particular multiple doses of the fluid, to be nebulized/dispensed.

The cartridge further comprises a closure, preferably forming a head of the cartridge and/or being located at the top of the cartridge. In particular, the closure closes the cartridge or container initially, i.e. before connection to the nebulizer, in particular preventing fluid to escape from the cartridge, and is adapted for fluidically connecting the container or cartridge to the nebulizer or a pump/pressure generator or delivery mechanism thereof.

The location of the closure on the cartridge preferably defines the top or head of the cartridge. In the following description, terms relating to positions and orientations, such as top, bottom, above, below or the like, preferably refer to said location of the closure, even if the cartridge is in a different position/orientation.

Further, the axial direction is to be understood as the direction from the closure or top of the cartridge to the bottom or opposite end of the cartridge. Preferably, the main length extension of the cartridge is in the axial direction. The radial direction is the direction perpendicular to said axial direction.

Particularly preferably, the cartridge is at least essentially cylindrical. In this case, the axial direction is the direction of the longitudinal axis of the cylinder and the radial direction is the direction of the radius of the cylinder.

The proposed nebulizer comprises a preferably insertable cartridge with a container containing a fluid to be nebulized and further comprises a housing for receiving the cartridge and a delivery mechanism for delivering or pressurizing the fluid.

The nebulizer comprises a preferably rigid connecting element for fluidically connecting the cartridge to the nebulizer or delivery mechanism, in particular being constructed as an elongated hollow cylinder or tube, in particular as a capillary.

The connecting element is preferably adapted to be inserted into the cartridge or closure and/or the cartridge or closure is preferably adapted to receive the connecting element. In particular, the closure comprises an opening for receiving the connecting element.

According to one aspect of the present invention, the closure comprises a valve that is adapted to open preferably permanently when the connecting element is received, preferably wherein the valve stays open as long as the connecting element is received. In particular, the valve is closed (only) initially, in particular before the cartridge is connected to the nebulizer and/or before the connecting element is received.

The valve preferably seals the cartridge, container or closure, in particular closes the opening in the closure. In this way, it is ensured that the cartridge is sealed from the environment, in particular preventing fluid from escaping and/or impurities from entering the cartridge and contaminating the fluid. Particularly preferably, the cartridge can thus be stored over a period of time before being used in the nebulizer.

When the connecting element of the nebulizer is received by or inserted into the closure or opening thereof, the valve preferably opens and a fluidical connection between the cartridge or container on the one hand and the nebulizer, delivery mechanism or connecting element on the other hand is formed or established, in particular permanently. Preferably, the fluidical connection is established such that no empty space, dead volume, gap and/or capillary stop is formed at the transition to the connecting element.

Particularly preferably, the valve is or stays open and/or the fluidical connection between the cartridge or container on the one hand and the nebulizer, delivery mechanism or connecting element on the other hand is maintained as long as the cartridge is connected with the nebulizer and/or as long as the connecting element is held in the closure or opening thereof. In particular, it is not possible to close the valve or to break the fluidical connection as long as cartridge and nebulizer are connected with each other.

Preferably, opening of the valve can be reversed, and/or the valve can be closed again after opening, particularly preferably only when the cartridge is disconnected from the nebulizer.

Particularly preferably, the cartridge or container can be filled with fluid via the closure, in particular after the cartridge has been assembled. In particular, the valve is adapted to open for filling and to close again after filling is completed.

In particular, a preferably elongate filling element can be inserted into or received by the closure or opening. The valve preferably opens and establishes a fluidical connection between the filling element and the cartridge or container, or is adapted thereto. This preferably allows the cartridge or container to be filled with fluid by the filling element.

When the filling element is removed, the valve preferably closes such that the now filled cartridge or container is sealed against the environment.

Advantageously, construction or manufacture of the cartridge is simplified since the cartridge can at least essentially be completely assembled before being filled with fluid.

Preferably, the closure comprises a movable closure element which is arranged within the closure or opening.

Particularly preferably, the closure element can move in the axial direction within the closure or opening thereof, thereby opening the valve.

Preferably, the closure further comprises a preferably integrally formed closure part which forms or comprises the opening. In particular, the closure element is movably held in or received by the closure part.

Further, the closure part can at least essentially form the head of the cartridge, in particular being arranged at the top of the container and particularly preferably extending axially into the interior of the container.

Particularly preferably, the closure element and the closure part form or comprise the valve. Preferably, the closure part forms or comprises a valve seat, in particular an inner wall of the closure part delimiting the opening, and the closure element, preferably arranged within the opening of the closure part, forms or comprises a valve member. When the valve is closed, the closure element or valve member preferably seals against the closure part or valve seat.

Preferably, the closure part is softer or more flexible than the closure element. In particular, the closure element or valve member is made of a rigid material, in particular hard plastic, and/or the closure part or valve seat is made of a flexible or elastic material, in particular rubber or soft plastic. In this way, the valve is formed or realized in a particularly simple and easy manner and/or a reliable closing or sealing of the cartridge, container and/or closure by the valve is realized.

According to another aspect of the invention, the closure element is adapted to displace a displacement volume of the fluid from the cartridge or container into the connecting element and/or nebulizer when the connecting element is received by or inserted into the closure or opening.

Preferably, the closure element is or forms or comprises a displacement device.

In particular, the closure element can be adapted to move towards the bottom of the cartridge or container or into the fluid when the connecting element is received or inserted.

Moving of the closure element into the fluid preferably displaces the fluid as desired. Thus, advantageously, the nebulizer, in particular its delivery mechanism and/or connecting element, can preferably automatically be filled with fluid when the cartridge is inserted or received. This reduces or eliminates the need that the nebulizer has to be actuated a couple of times before its delivery mechanism is completely filled with fluid, before the nebulizer can dispense a dose of fluid and/or before the nebulizer can be used as desired.

Particularly preferably the nebulizer can be used or can dispense a desired dose of fluid already with the first actuation. In particular, the size of the displacement volume is at least about the size of one dose of fluid to be nebulized.

To ensure that the delivery mechanism is completely filled with fluid, the size of the displacement volume is preferably more than one dose of fluid, in particular about the size needed to fill the delivery mechanism completely with fluid, particularly preferably two to four doses of fluid. This ensures, that the delivery mechanism is completely filled, in particular both the connecting element and a chamber of the nebulizer for pressurizing one dose of fluid. Advantageously, dead volume is further reduced or completely eliminated since the whole delivery system is preferably automatically filled with fluid when the cartridge is received or inserted.

Especially preferably, moving of the closure element, in particular in the axial direction towards the fluid or bottom of the cartridge or container, opens the valve on the one hand and displaces the displacement volume on the other hand. Thus, advantageously, both aspects are combined by providing the proposed closure element. This is especially conducive to simple and/or cost-effective manufacturing, in particular since the number of parts of the cartridge is reduced.

Preferably, the closure element is moved by the connecting element pushing or being pressed on the closure element, in particular in the axial direction and/or from above, when being inserted or received. Thus, the closure element is preferably moved automatically from a closed position into an open position when the cartridge is connected to the nebulizer.

According to another aspect of the present invention, which can also be implemented independently, the closure or closure part is adapted to form a sealing with the outer container of the cartridge on the one hand and to sealingly receive the connecting element and/or form a sealing with a holder of the nebulizer for holding the cartridge on the other hand.

In particular, the closure part is integrally formed or formed as one piece and provides or forms both the sealing with the outer container of the cartridge on the one hand and the connecting element and/or holder on the other hand.

Preferably, the outer container comprises a portion which is integrally formed or formed as one piece with the container for forming the sealing with the closure or closure part. In particular, the container is at least essentially cylindrical and/or forms an outer cylindrical shell of the cartridge with the integrally formed portion protruding radially towards the longitudinal or central axis of the container, in particular at the top of the container.

Preferably, the integrally formed portion comprises a central opening or defines an opening of the container, in particular the closure being received in said opening.

The closure, in particular the closure part, preferably comprises a circumferential notch or neck for engagement with the container, in particular the integrally formed portion thereof. The sealing is preferably formed between the closure part, in particular the neck, and the integrally formed portion, in particular a circumferential edge thereof.

Alternatively or preferably additionally, the closure part forms a further sealing with an axial abutment face of said integrally formed portion of the container, in particular by (axial) press/tight-fit between the closure part, in particular its outer portion, and said axial abutment face.

Particularly preferably, the closure part is softer or more flexible than the container, in particular the integrally formed portion thereof. In particular, the container is made of a rigid material, such as glass, metal or hard plastic and the closure part is made of a flexible and/or elastic material such as rubber. This ensures that a reliable sealing between the closure and the container is formed, in particular in a press/tight-fit manner.

Preferably, at least separate sealings are formed when the connecting element is inserted into or received by the closure, closure part or opening thereof.

In particular, the closure or closure part or its opening comprises a preferably tapered first portion and a preferably at least essentially cylindrical second portion with one sealing being formed or established at the first portion and another sealing being formed or established at the second portion.

The closure or closure part, in particular the at least essentially cylindrical second portion thereof, is preferably adapted to encompass or seal the connecting element in a liquid- and/or gas-tight manner. In particular, the closure or closure part can be stretchable or flexible, at least in part. When the preferably rigid connecting element is inserted into or received by the closure, closure part or opening, in particular the second portion, the closure or closure part, in particular the second portion, preferably stretches apart and/or forms a sealing with the connecting element in a press/tight-fit manner.

A sealing at the first portion can be realized in the same manner as for the sealing at the second portion. However, preferably the sealing is formed or established by press-fit in a direction different from the radial direction. In particular, a part of the nebulizer, in particular a holder for holding the cartridge, can be pressed at least essentially axially, preferably with a surface inclined with respect to the radial direction, onto a corresponding surface of the closure or first portion. This preferably improves or enhances the sealing as both sealing in the radial direction and at least essentially the axial direction is provided.

By providing sealings as described above, it is ensured that fluid can only exit the cartridge as desired via the connecting element or via the fluidical connection between the cartridge and connecting element, but cannot escape the cartridge via any other (undesired) passages. Further, sealing the connecting element, in particular radially at its axial end, reduces the dead volume as there is no annular gap between closure and connecting element into which fluid could get.

According to another aspect of the present invention, which can also be implemented independently, the closure is self-locking and/or self-sealingly connected with the container of the cartridge, in particular the outer container of the cartridge.

This connection with the container is preferably realized in the manner described above, in particular by the closure or closure part being held in an opening of the container, in particular by a preferably integrally formed portion thereof in a press/tight-fit manner. In this way, corresponding advantages can be achieved.

According to another aspect of the present invention, which can also be implemented independently, the preferably integrally formed closure part forms at least two sealings with the (outer) container by direct abutment or pressing against the container. In particular, one of the sealings is formed or established in the axial direction of the cartridge or container and another sealing is formed or established in the radial direction of the cartridge or container. Both sealings are preferably formed/established by press/tight-fit of the closure part with the container.

Preferably, in this way, a very secure liquid- and/or gas-tight connection between the closure and the container is provided such that no fluid can escape therethrough. In particular, these sealings are formed both in the initial state of the cartridge, i.e. before being inserted into the nebulizer, and when being connected. Thus, for the initial state, a very storage-stable cartridge is provided. On the other hand, it is ensured that fluid can only exit the cartridge via the connecting element, when the cartridge is connected to the delivery mechanism.

According to another aspect of the present invention, which can also be implemented independently, the outer container of the cartridge comprises an annular, flange-like portion holding the closure and/or forming an axial abutment face for the closure.

In particular, the annular portion is flat, planar and/or in the normal operating position preferably at least essentially horizontal.

Particularly preferably, the annular portion is integrally formed or formed as one piece with the outer container. In particular, the annular portion can be the same portion which engages with the neck of the closure part. Thus, advantageously, said portion both forms an axial abutment face for the closure or closure part on the one hand and radially holds and/or seals the closure or closure part, preferably by press/tight-fit.

Preferably, one sealing is formed/established by axial press/tight-fit between said annular portion, in particular its axial abutment face, and the closure part, in particular its outer portion.

Preferably, one sealing is formed/established by radial press/tight-fit between said annular portion, in particular a circumferential edge thereof, and the closure part, in particular its neck.

According to another aspect of the present invention, the cartridge or closure is adapted to compensate for length tolerances of the connecting element, in particular both in the axial and the radial direction.

Compensation of radial length tolerances is preferably realized by the closure or closure part being made of a flexible or elastic material and/or by the connecting element being made of a rigid material.

In particular, when the preferably rigid connecting element is inserted into or received by the closure opening, the closure or closure part preferably stretches apart. Advantageously, in this manner preferably both a sealing is formed or established as described above and further any radial length tolerances of the connecting element are compensated for.

Compensation of axial length tolerances of the connecting element is preferably realized by providing the movable closure element. In particular, the axial stroke of the closure element when being pushed by the connecting element can be variable, depending on the length of the connecting element.

Preferably, the closure or valve is adapted to establish the fluidical connection between the connecting element or nebulizer on the one hand and the cartridge or container on the other hand for connecting elements of different length. In particular, the valve is adapted to open for connecting elements of different length and/or to open already for small axial stroke of the closure element.

Further, displacing of fluid as explained above is preferably possible for connecting elements of different length. Preferably, it is ensured that enough fluid is displaced, in particular a displacement volume having at least the size of one dose of fluid.

According to another aspect of the present invention, the cartridge or closure comprises a securing element. Preferably, the closure or closure part is secured, mounted or fixed to or held at the container by means of the securing element.

Particularly preferably, the securing element secures, holds or fixes the closure or closure part in the axial direction and/or in a form-fitting manner.

By providing the securing element, preferably very simple and reliable fixing, securing or mounting of the closure or closure part to the container is facilitated, which is in particular insensitive to changes in temperature.

Particularly preferably, the closure or closure part is pressed onto the container, in particular in the axial direction, by means of the securing element and/or the closure part is clamped between the securing element and the container. Preferably, in this way, the sealing in the axial direction between the closure and the container is achieved.

Particularly preferably, the securing element is embodied as a crimp cap and/or encompasses or engages with a flange or flange-like portion of the container.

The securing element preferably comprises a central recess/opening and/or is formed ring-like, in particular such that the connecting element of the nebulizer can pass or reach through the securing element or central recess/opening thereof when the cartridge is inserted into the nebulizer and/or connected to a delivery mechanism of the nebulizer.

According to another aspect of the present invention, the cartridge or closure comprises at least one seal which closes or seals the cartridge, container or closure, in particular the opening of the closure, initially or before receiving the connecting element.

Preferably, the seal is formed by the closure element or is embodied as a cap or cover covering the opening, as a spherical seal which is preferably press-fitted into the opening or as a membrane or sealing wall which is located within the opening and preferably formed as one piece with the closure part.

The connecting element is preferably adapted to pierce through or break the cover and/or membrane or sealing wall and/or to push the spherical seal further into the cartridge. In particular, the connecting element is adapted to open or break any seal which closes the opening initially in order to establish a fluidical connection.

Another aspect of the present invention relates to a nebulizer comprising the proposed cartridge. In this way, corresponding advantages can be achieved.

A further aspect of the present invention relates to a method for fluidically connecting the proposed cartridge to the delivery mechanism of the nebulizer for nebulizing the fluid. In particular, the method comprises the steps of inserting the connecting element into the closure, to open the valve and to displace the displacement volume of fluid into the connecting element and/or delivery mechanism of the nebulizer.

In particular, opening of the valve and displacement of the fluid is performed simultaneously or displacing the fluid is performed immediately after opening the valve. In particular, opening of the valve establishes a fluidical connection between the cartridge or container on the one hand and the connecting element on the other hand, such that displacing of the fluid into the connecting element via said connection is made possible.

The aspects of the present invention mentioned above and in the following can be realized independently of one another and in any combination.

BRIEF DESCRIPTION OF THE DRAWINGS

Further advantages, features, characteristics and aspects of the present invention will become apparent from the claims and the following description of a preferred embodiment with reference to the drawings.

DETAILED DESCRIPTION

Figure 1:
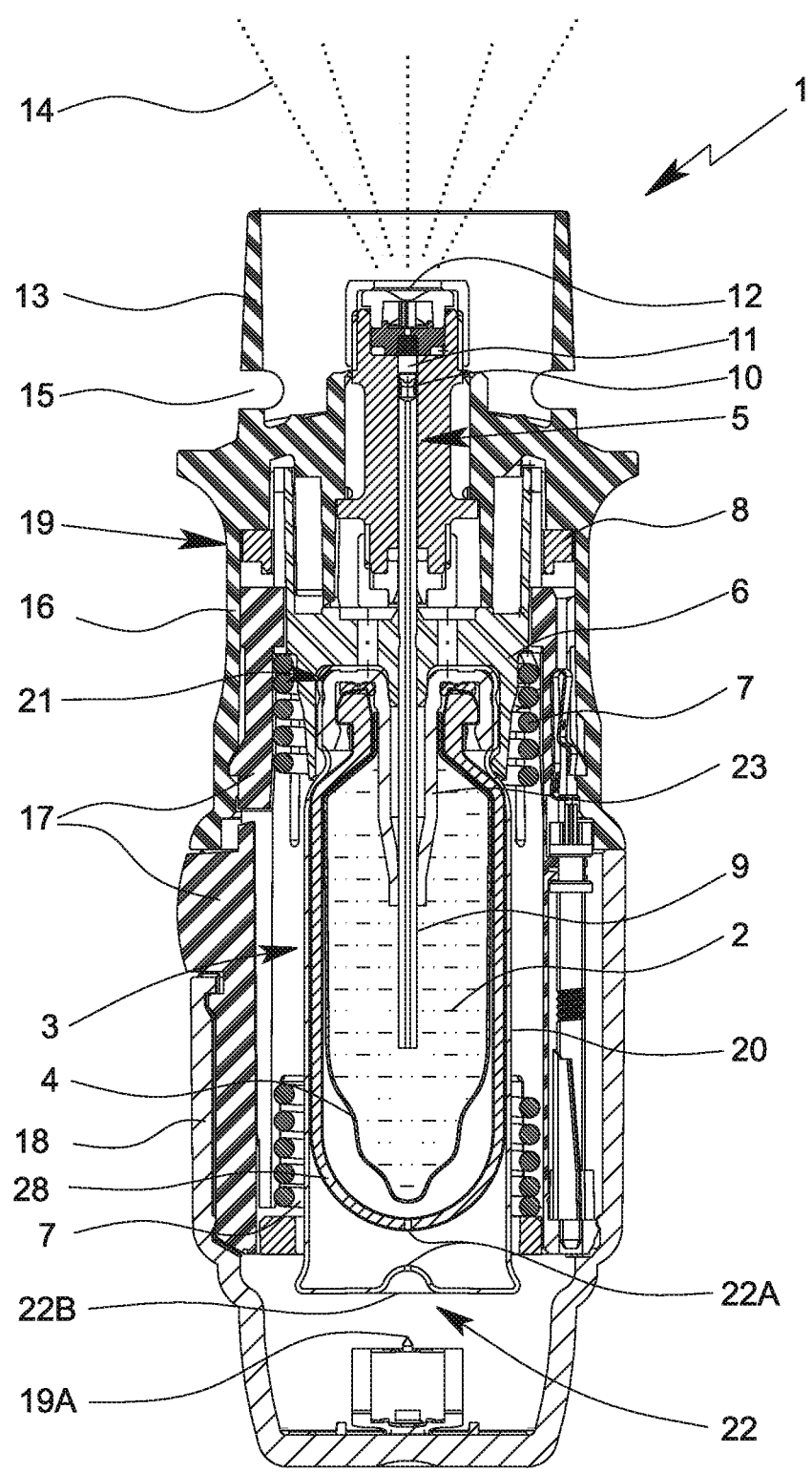
FIG. 1 is a schematic section of a known nebulizer in a non-tensioned state.

In the figures, the same reference numerals are used for identical or similar parts, preferably resulting in corresponding or comparable properties and advantages, even if the associated description is not repeated.

Figure 2:
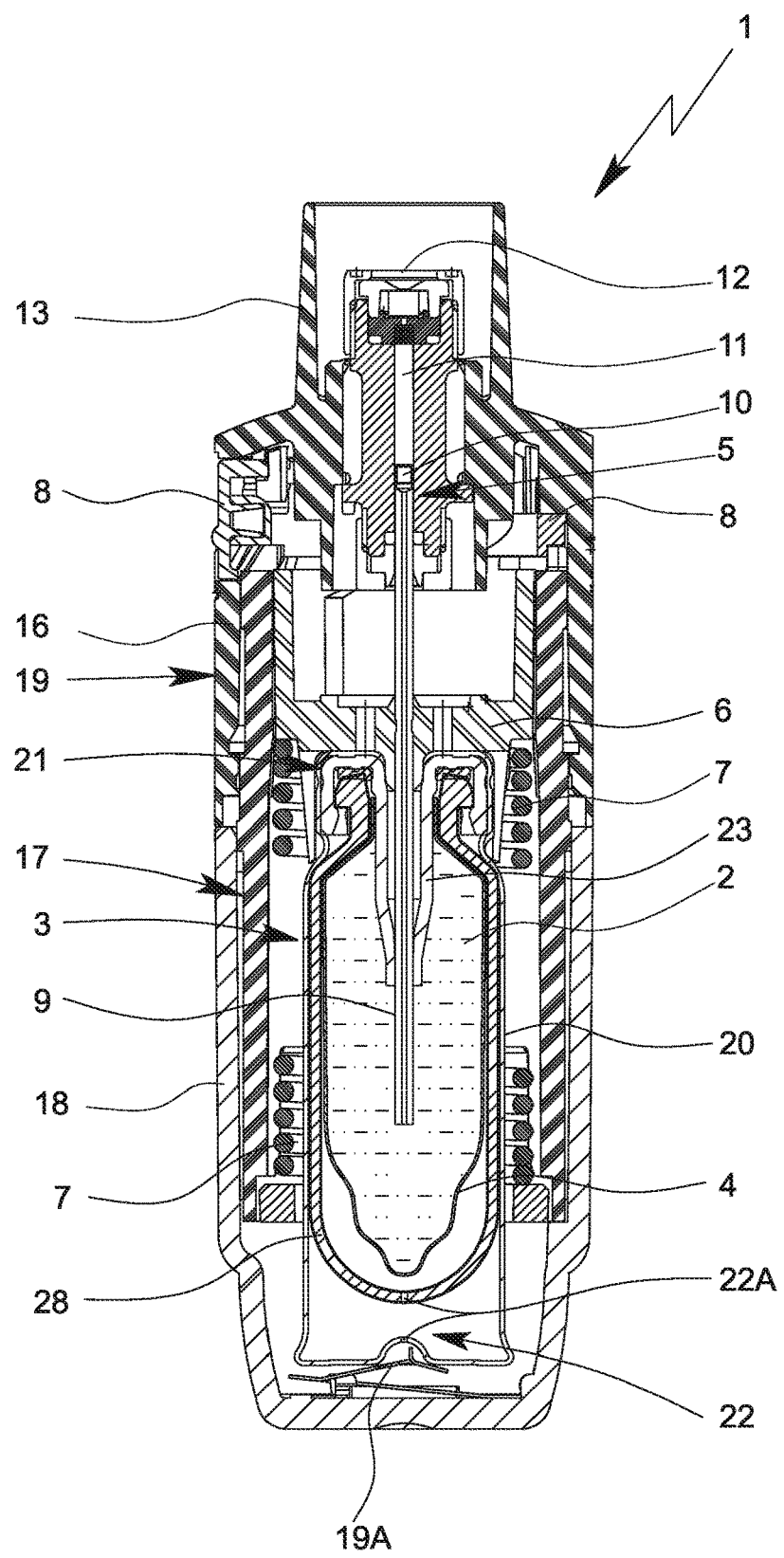
FIG. 2 is a schematic section, rotated by 90° compared to FIG. 1, of the known nebulizer in a tensioned state.

FIG. 1 and FIG. 2 show a known system or nebulizer/dispensing device 1 for atomizing/nebulizing/dispensing of a fluid 2, in particular a pharmaceutical composition, medicament or the like, schematically shown in a non-tensioned/initial state (FIG. 1) and in a tensioned (ready to use) state (FIG. 2).

The system or nebulizer 1 is preferably adapted to dispense and/or nebulize the fluid 2 or a dose thereof.

Preferably, when the fluid 2, preferably a liquid, more particularly a pharmaceutical component, is nebulized/dispensed, an aerosol 14 (as indicated by dashed lines in FIG. 1) is formed or dispensed, which can be breathed in or inhaled by a user (not shown).

Usually, the inhaling is done at least once a day, more particularly several times a day, preferably at set intervals, depending on the complaint or illness from which a patient is suffering.

The system or nebulizer 1 is constructed in particular as a portable inhaler and/or operates preferably only mechanically and/or without a propellant/gas. Nevertheless, other constructions are possible as well.

The nebulizer 1 is provided with or comprises or is adapted to receive an insertable or replaceable cartridge 3 containing the fluid 2 as shown in FIGS. 1 and 2. Thus, the cartridge 3 forms a reservoir for the fluid 2, which is to be nebulized/dispensed.

In particular, a system for nebulizing the fluid 2 comprises the nebulizer 1 and the cartridge 3, and/or the nebulizer 1 and cartridge 3 form a system. In such a system, the cartridge 3 can preferably be replaced or exchanged by another cartridge 3, in particular when the amount of fluid 2 provided by the cartridge 3 is used up. However, it is possible to limit the number of possible replacements of cartridges 3 with the same nebulizer 1.

For the sake of brevity, the following description does not differ between the system and the nebulizer 1. However, when in the description reference is made to nebulizer 1, this shall also encompass a system comprising the nebulizer 1 and the cartridge 3.

Preferably, the cartridge 3 contains multiple doses of the fluid 2, in particular sufficient to provide at least 100 or 150 and/or up to 200 or more dosage units or doses, i.e. to allow at least 100 and/or up to 200 sprays or applications.

The cartridge 3 preferably holds a volume of about 0.5 ml to 30 ml, particularly preferably about 4 ml to 20 ml. Further, the number of doses contained in the cartridge 3 and/or the total volume of the fluid 2 contained in the cartridge 3 can vary depending on the fluid 2 or respective medicament and/or depending on the cartridge 3 and/or depending on necessary medication or the like.

Preferably, the nebulizer 1 is adapted to nebulize/dispense a dose of 1 µl to 80 µl of fluid 2, even more preferably a dose of more than 5 µl, 10 µl or 20 µl or of about 15 µl or 50 µl within one actuation/use of the nebulizer 1 and/or within one spray/aerosol delivery/dispension.

Preferably, the cartridge 3 can be replaced or exchanged, in particular as disclosed in WO 2012/162305 A1. Preferably, the total number of uses of the nebulizer 1 and, thus, the number of cartridges 3, which can be used with the same nebulizer 1, is restricted, e.g. to a total number of four, five or six cartridges 3. WO 2012/162305 A1 discloses such a restriction to the total number of cartridges 3 which can be used with the present nebulizer 1.

The cartridge 3 comprises a preferably rigid (outer) container 20. The fluid 2 can be held directly in the container 20, or in an inner container or bag.

The cartridge 3 or container 20 can comprise or form a variable or collapsible volume 4 for the fluid 2, such as a (flexible) inner container of variable volume, preferably a collapsible bag. In FIGS. 1 and 2, the collapsible volume 4 is formed by a bag.

Figure 3:
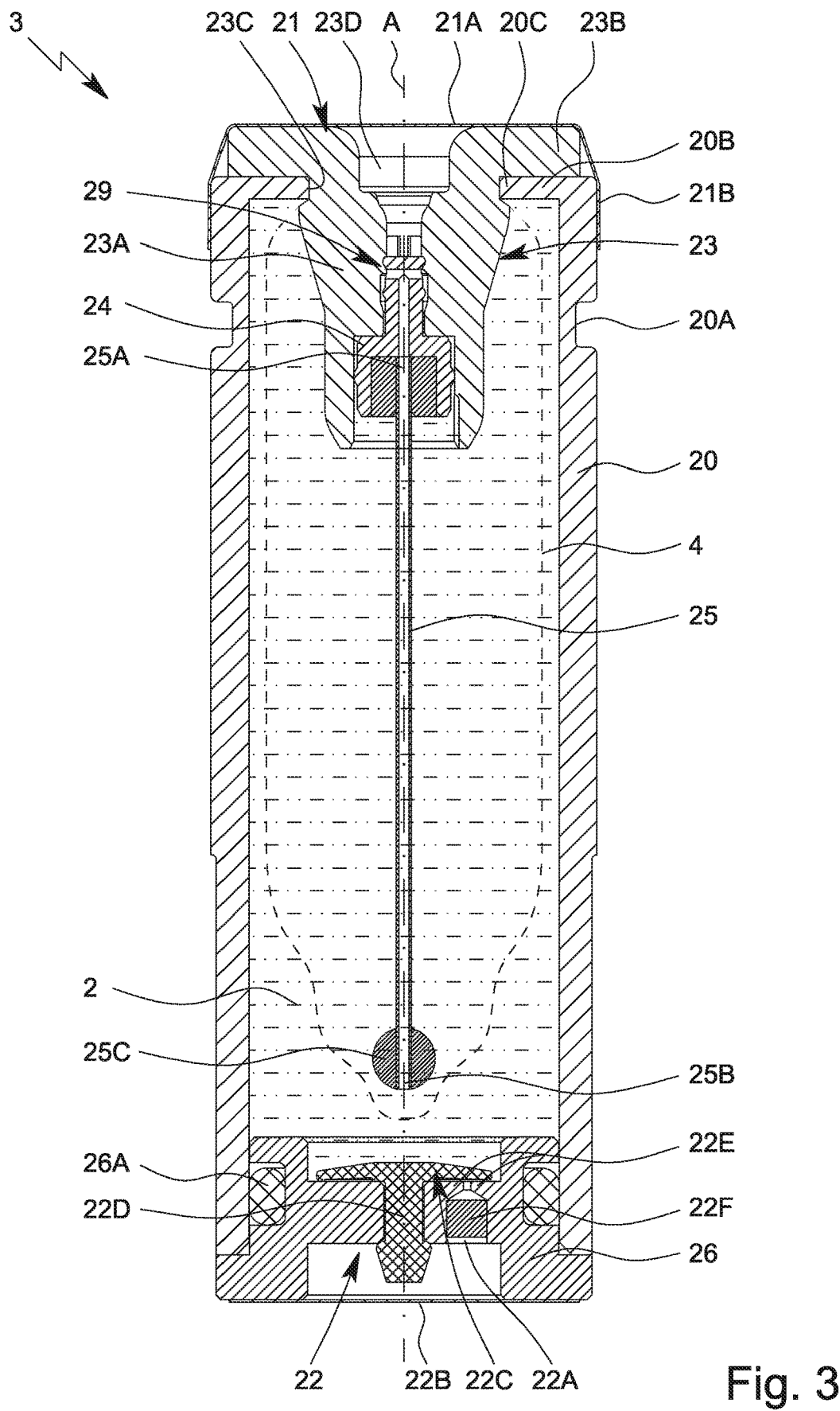
FIG. 3 is a schematic section of a cartridge according to a preferred embodiment of the invention.

The cartridge 3 can in particular be formed of or comprise a plurality of containers. In the example shown in FIGS. 1 and 2, the cartridge 3 comprises three containers, in particular the outer container 20, an intermediate container 28 and the collapsible volume 4 in the form of a flexible bag. However, also other structural solutions are possible here. FIG. 3 shows for example a construction comprising only one container 20 which directly contains the fluid 2 as well as a construction with two containers, in particular (outer) container 20 and collapsible volume 4 in the form of a flexible bag (indicated by dashed lines).

The cartridge 3, in particular the container 20, is preferably substantially cylindrical or cartridge-shaped and/or of rigid construction. Nevertheless, other constructional solutions are possible as well. In particular, the cartridge 3 or container 20 can be at least partially spherical.

Preferably, once the nebulizer 1 has been opened, the cartridge 3 can be inserted therein, preferably from below and changed if desired.

The cartridge 3 is preferably closed and/or sealed and/or comprises preferably a closure 21, preferably wherein the closure 21 is adapted to close and/or seal the container 20 and/or volume 4, here at one end, in particular in a gas-tight and/or liquid-tight manner.

Optionally, the cartridge 3, in particular the container 20, comprises a ventilation/aeration 22, e.g. a valve, opening or hole, for venting/aeration of the cartridge 3, in particular container 20, preferably in order to enable or support withdrawal of fluid 2 from the container 20.

Preferably, the ventilation 22 forms a direct or indirect gas connection between the interior of the container 20 and its surroundings and/or the ambient and/or allows a pressure compensation between the interior of the container 20 and its surroundings and/or the ambient.

In FIGS. 1 and 2, the ventilation 22 is preferably realized as an aeration hole 22A. The aeration hole 22A can be closed initially, in particular by a film, foil or cover 22B. The cover 22B is preferably pierceable or breakable in order to open the ventilation 22.

When the ventilation 22 is open, air or any other gas can flow through the ventilation 22 into the container 20 so that pressure compensation between the interior of container 20 and its surrounding is possible or achieved. In particular, negative air pressure can be avoided or at least compensated when withdrawing the fluid 2 and/or optionally collapsing the volume 4, in particular the flexible bag.

Preferably, the ventilation 22 opens automatically and/or before or during first use of nebulizer 1.

Optionally, the ventilation 22 can be integrated in the closure 21 and/or opened together with closure 21, as described in WO 2006/136426 A1, e.g. on page 9, line 20, to page 14, line 2.

In such an embodiment, the ventilation 22, such as a thin canal, is preferably opened/created by opening/piercing the closure 21 or a cover 21A thereof, in particular wherein pressure compensation through the ventilation 22 takes places without fluid 2 leaking therethrough.

The nebulizer 1 comprises preferably a delivery/pressurizing mechanism 5, preferably a pressure generator or pump, for withdrawal, pressurizing, conveying and/or nebulizing/dispensing of fluid 2, particularly in a preset and optionally in an adjustable dosage amount.

In particular, the delivery mechanism 5 withdraws or sucks fluid 2, namely a dose of the fluid 2, from the fluidically connected cartridge 3, in particular from container 20 and/or volume 4, preferably when cocking or tensioning or loading the nebulizer 1. Subsequently, the withdrawn fluid 2 or dose of fluid 2 is dispensed, in particular pressurized and/or nebulized, preferably in a second step, in which the mechanical energy which has been stored during the earlier tensioning is released.

In particular, the nebulizer 1 comprises an energy store (preferably a drive spring 7) which is loaded (preferably tensioned) during the loading or tensioning process and the energy is released for nebulizing the fluid 2 or dose of fluid 2 which has been drawn into the nebulizer 1 during the tensioning or loading process. Thus, the normal use of the nebulizer 1 encompasses the loading process and the dispensing process.

The nebulizer 1 or delivery mechanism 5 comprises preferably a holder 6 for (releasably) holding the cartridge 3, the energy store or drive spring 7 being associated to the holder 6 (partly shown in FIG. 1 and FIG. 2), and/or comprises a blocking element 8 preferably connected to a button for preferably manual actuation or depressing.

The blocking element 8 can preferably catch and block the holder 6 and/or can be manually operated to release the holder 6 allowing the energy store or drive spring 7 to expand.

The nebulizer 1 or delivery mechanism 5 comprises preferably a conveying/connecting element 9, such as a conveying tube, a non-return valve 10, a pressure chamber 11, a nozzle 12 for nebulizing the fluid 2 and/or a mouthpiece 13.

The completely inserted cartridge 3, preferably its closure 21 or head, is fixed or held in the nebulizer 1 via the holder 6, preferably in a form-fit manner, in particular such that the connecting element 9 fluidically connects the container 20 and/or volume 4 to the nebulizer 1 or delivery mechanism 5.

Preferably, when inserting the cartridge 3 into the nebulizer 1 and/or when connecting cartridge 3 to the delivery mechanism 5, the connecting element 9 penetrates into the closure 21, container 20 and/or volume 4.

Preferably, the connecting element 9 is constructed as an elongated hollow cylinder, in particular as a, preferably capillary, tube.

Preferably, the connecting element 9 is rigid, in particular made of metal, mostly preferred of stainless steel, and/or adapted to pierce or break the cover 21A and to open the closure 21.

The axial end of the connecting element 9 is preferably planar or flat and/or lies in a plane at least essentially perpendicular to the longitudinal axis of the connecting element 9.

The edge of the axial end of the connecting element 9 is preferably sharp such that piercing or breaking of the cover 21 by the connecting element 9 is facilitated.

Mostly preferred, the connecting element 9 is constructed as a capillary, in particular having an inner diameter of less than 1 mm or 0.8 mm, mostly preferred less than 0.7 mm or 0.5 mm, and/or more than 0.1 mm or 0.2 mm. However, the inner diameter should not be dimensioned too small as this reduces the flow rate that can be achieved within the connecting element 9.

The nebulizer 1, in particular holder 6, is preferably constructed so that the cartridge 3 can be released or exchanged.

When the energy store or drive spring 7 is axially loaded/tensioned in the tensioning process or during cocking, the holder 6, the cartridge 3 and the connecting element 9 are moved downwards and/or towards the base of cartridge 3.

Through the movement of the connecting element 9 downwards and/or towards the base of cartridge 3 the volume of pressure chamber 11 is enlarged and/or the pressure within pressure chamber 11 is decreased, in particular such that fluid 2 is withdrawn or sucked out of the container 20 and/or volume 4 via the connecting element 9 into the delivery mechanism 5, in particular into pressure chamber 11 through the non-return valve 10. In this state, the holder 6 is caught by the blocking element 8 so that the energy store or drive spring 7 is kept compressed. Subsequently, the nebulizer 1 is in the cocked or tensioned state.

In particular, in the sense of the present invention, tensioning of the energy store or drive spring 7 is preferably to be understood as compressing the energy store or drive spring 7. Thus, energy is preferably stored in the compressed drive spring 7 and/or the tensioned state is preferably the state in which the energy store or drive spring 7 is (further) compressed with respect to its non-tensioned/initial state and/or in which the nebulizer 1 can be actuated and/or a dose of the fluid 2 can be dispensed.

The non-tensioned/initial state is preferably the state in which the energy store or drive spring 7 is relaxed and/or less compressed compared to the tensioned state. Mostly preferred, the non-tensioned/initial state is the state after actuation of the nebulizer 1 and/or after dispensing a dose of the fluid 2.

In particular, the energy stored in the energy store or drive spring 7 is released by (partial) expansion of the energy store or drive spring 7 from the compressed/tensioned state into the relaxed/non-tensioned state. However, also other solutions are possible here, for example in which tensioning of the energy store or drive spring 7 is to be understood as (further) expanding the energy store or drive spring 7 with respect to its non-tensioned/initial state and the energy stored in the energy store or drive spring 7 is released by (partial) contraction of the energy store or drive spring 7.

During the subsequent relaxation in the dispensing/nebulization process, i.e. after actuation or pressing of the blocking element 8, the connecting element 9 with its now closed non-return valve 10 is moved back towards the pressure chamber 11, in the FIG. 1 and FIG. 2 upwards, thereby decreasing the volume of pressure chamber 11. Due to the now closed non-return valve 10 the fluid 2 or a dose thereof in the pressure chamber 11 is put under pressure. Thus, in this state, the non-return valve 10 acts as a pressing ram or piston.

The pressure generated in this way forces the fluid 2 or the dose thereof through the nozzle 12, whereupon it is nebulized into an aerosol 14, as indicated by dashed lines in FIG. 1.

Generally, the nebulizer 1 operates with a spring pressure of 5 MPa to 300 MPa, preferably 10 MPa to 250 MPa on the fluid 2, and/or with a volume of fluid 2 delivered per stroke of 10 to 80 μl, preferably about 15 μl or about 40 to 50 μl.

The fluid 2 is converted into or nebulized as aerosol 14, the droplets of which have an aerodynamic diameter of up to 20 μm, preferably 3 μm to 10 μm.

Preferably, the generated jet spray is cone-shaped and/or has an opening angle of 20° to 160°, preferably 80° to 100°. These values also apply to the nebulizer 1 according to the teaching of the present invention as particularly preferred values.

A user or patient (not shown) can inhale the aerosol 14 generated in this way, preferably while air can be sucked into the mouthpiece 13 through at least one optional air supply opening 15.

Preferably, when normally operated, the aerosol 14 is dispensed at the top of the nebulizer 1 and/or the mouthpiece 13 is located at the top of the nebulizer 1. In this normal operating position, the axial direction and/or longitudinal axis of the nebulizer 1 or cartridge 3 runs preferably at least essentially vertically. However, it is particularly preferably also possible to use the nebulizer 1 in a position different from said normal operating position.

The nebulizer 1 comprises preferably a housing 19 with an upper housing part 16, an inner housing part 17 and/or a lower housing part 18.

The inner housing part 17 and/or lower housing part 18 are/is preferably rotatable relative to the upper housing part 16. In particular, the lower housing part 18 is manually operable and/or releasable fixed, particularly fitted or held onto the inner housing part 17, preferably by means of a retaining element.

In order to insert and/or replace the cartridge 3, preferably the housing 19 can be opened and/or the lower housing part 18 can be detached from nebulizer 1, in particular from inner housing part 17.

Preferably, the cartridge 3 can be inserted before the housing 19 is closed and/or before the lower housing part 18 is connected to the inner housing part 17 or upper housing part 16. Alternatively, the cartridge 3 may be inserted, opened and/or fluidically connected to the delivery mechanism 5 automatically or simultaneously when (completely) connecting the lower housing part 18 to the upper housing part 16 and/or the inner housing part 17 and/or when (completely) closing the housing 19 or nebulizer 1.

The lower housing part 18 preferably forms a cap-like lower housing part and/or fits around or over a lower free end portion of the cartridge 3.

Preferably, the nebulizer 1 or drive spring 7 can be manually activated or tensioned or loaded, in particular by actuation or rotation of an actuation member, here preferably by rotation of lower housing part 18 or any other component.

The actuation member, preferably the lower housing part 18, can be actuated, here rotated relative to the upper housing part 16, carrying with it or driving the inner housing part 17.

The inner housing part 17 acts on a gear or transmission to transform the rotation into an axial movement of the holder 6 and cartridge 3. As a result, the energy store or drive spring 7 is loaded or tensioned in the axial direction by means of the gear or transmission (not shown) formed between the inner housing part 17 and the holder 6.

During tensioning the cartridge 3 and holder 6 are moved axially downwards until the cartridge 3 occupies or assumes an end position, as shown in FIG. 2. In this activated or tensioned state, the energy store or drive spring 7 is under tension and can be caught or held by the blocking element 8.

During the nebulizing process the cartridge 3 is moved back into its original position (non-tensioned state shown in FIG. 1) by (the force of) the energy store or drive spring 7. Thus, the cartridge 3 executes a lifting or stroke movement during the tensioning process and during the nebulizing process.

As the energy store or drive spring 7 is loaded or tensioned the cartridge 3 moves with its end portion into the lower housing part 18 or towards the end face thereof.

An aeration means, such as a piercing element 19A arranged in the housing 19, in particular the lower housing part 18, preferably opens or pierces the cartridge 3, preferably the container 20, in particular the ventilation 22 or its cover 22B, when the cartridge 3 makes contact with it for the first time. In this way, air can flow into the cartridge 3, in particular container 20, and pressure compensation can take place when fluid 2 is withdrawn from the cartridge 3 during the tensioning of the nebulizer 1.

In the following and with reference to the further figures, preferred embodiments of the nebulizer 1 and/or cartridge 3 are described and shown according to the invention, wherein primarily important aspects and differences will be described and the previous aspects, features and explanations apply preferably additionally or correspondingly even without repetition.

FIGS. 3 to 11 show the cartridge 3 according to a first embodiment of the present invention.

FIG. 3 shows the cartridge 3 according to the present invention in a schematic section, in particular before being connected to the nebulizer 1.

The fluid 2 is preferably directly contained within container 20, but also an optional bag or another variable/collapsible volume 4 could be used as indicated by dashed lines.

Optionally, the intermediate container 28 can be provided as explained in connection with FIGS. 1 and 2. However, in the preferred embodiment as shown in FIG. 3 the intermediate container 28 is omitted. In particular, cartridge 3 only comprises one rigid container 20.

The cartridge 3, in particular container 20, further preferably comprises an indentation or recess 20A. Recess 20A can be embodied e.g. as a circumferential notch around container 20. Preferably, the nebulizer 1, in particular the holder 6 holds the cartridge 3 when connected to the nebulizer 1 by engaging into the recess 20A.

Preferably, the cartridge 3, in particular the closure 21, comprises a preferably pierceable cover 21A.

The cover 21A is schematically shown in FIG. 3, in which the cartridge 3 according to a preferred embodiment of the invention is in a closed/unpierced state. The cover 21A is further shown schematically in FIG. 6 in a closed/unpierced state and in FIG. 7 in an open/pierced state according to the preferred embodiment of the present invention.

The cover 21A covers or seals preferably the container 20 and/or the closure 21 or a closure part 23 or opening 23D thereof, at least before the cartridge 3 is inserted into the nebulizer 1. Preferably, the cover 21A is a foil or film.

Preferably, the cover 21A covers the closure 21 axially completely and/or extends around or over the circumference of the closure 21. In particular, the cover 21A comprises a preferably annular cover portion 21B which extends over the container 20 and/or is attached to or fixed at the (outer) container 20, preferably a circumferential side wall thereof. Thus, the cover 21A preferably covers the whole closure 21. Particularly preferably, the cover 21A forms a seal preventing that any fluid 2 can escape at the top/head of the cartridge 3 or container 20.

In particular, the cover 21A protects the cartridge 3, container 20 and/or fluid 2 from contamination, for example by dust. Preferably, the shelf-life of the cartridge 3 is increased by providing the cover 21A. In addition, the cover 21A preferably provides a tamper-proof seal or originality seal such that a user can easily see if the cartridge 3 is unopened/sealed.

Preferably, the connecting element 9 of the nebulizer 1 pierces or breaks/opens the cover 21A when the cartridge 3 is inserted into and/or connected to the nebulizer 1, or is adapted thereto.

Preferably, when inserting the cartridge 3 into nebulizer 1 and/or when connecting cartridge 3 to the delivery mechanism 5 the connecting element 9 pierces or breaks cover 21A, at least partially.

Preferably, the closure 21A is only pierced or broken in the region of the opening 23D. In particular, the cartridge 3 and closure 21/closure part 23 is laterally sealed by the cover 21A, in particular cover portion 21B, particularly preferably also after the cover 21A has been broken or pierced and/or after the cartridge 3 is connected to the nebulizer 1.

Preferably, the closure 21 comprises the closure part 23 which in particular extends into the interior of the container 20.

The closure part 23 preferably comprises an at least essentially cylindrical or inner portion 23A and a preferably flange-like or outer portion 23B protruding radially therefrom, in particular at the top.

Preferably, the outer portion 23B rests on top of the container 20 with the inner portion 23A extending into the interior of container 20.

Particularly preferably, the closure part 23 is integrally formed or formed as one piece.

The closure part 23 is preferably embodied as a plug which is inserted into an opening of the container 20 to close and/or seal the container 20.

The container 20 can comprise a portion 20B, in particular at the top or end of the container 20 which protrudes radially, in particular in the normal operating position horizontally, towards the longitudinal or central axis of container 20 or cartridge 3. In particular, the portion 20B forms a preferably circular opening at the top of container 20 which receives the closure 21, in particular the closure part 23.

The portion 20B is particularly preferably integrally formed or formed as one piece with the (outer) container 20.

The portion 20B preferably forms the top of container 20. In particular, the portion 20B can be understood as the top portion of container 20. Preferably, said (top) portion 20B has a reduced inner diameter compared to the main portion of the container 20, i.e., the portion of the container 20 containing the fluid 2 or forming the volume 4.

Preferably, the outer portion 23B of the closure part 23 rests on the portion 20B or outside of the container 20 with the inner portion 23A extending into the interior of container 20 through the opening formed by the portion 20B.

Preferably, the portion 20B forms an annular face against which the closure part 23 abuts or covers with its outer portion 23B, preferably in the axial direction.

In particular, the portion 20B is at least essentially flat, planar, annular, and/or flange-like and/or is in the normal operating position at least essentially horizontal and/or extends radially to the longitudinal axis of the cartridge 3/container 20.

Particularly preferably, the closure 21 or closure part 23 is held by the portion 20B at or in the container 20.

Preferably, the closure part 23 further comprises a preferably circumferential indentation or neck 23C. In particular, the closure part 23 or closure 21 is fixed or held on the container 20 at the neck 23C, in particular by portion 20B, in particular an edge 20C thereof, engaging with or into the neck 23C, particularly preferably in a press/tight-fit manner.

The edge 20C is preferably annular and/or forms in the normal operating position preferably an at least essentially vertical face.

Preferably, the opening of the container 20 which receives the closure 21 or closure part 23 is formed or defined by the edge 20C.

Preferably, the edge 20C forms a radial abutment face for the closure 21, in particular for neck 23C.

Preferably, the portion 20B forms an axial annular support or abutment for the closure 21, closure part 23 or outer part 23B.

Preferably, the closure part 23 is made of flexible or elastic material, in particular a rubber or a plastic with elastomeric properties, such as polyamide, polyethylene, polypropylene, polyurethane, polybutylene terephthalate, polyether block amide, nitrile rubber, butadiene rubber, styrene-butadiene rubber, isoprene rubber, styrene-isoprene rubber, butyl rubber, ethylene propylene diene monomer rubber or the like. Other suitable materials might be used as well.

Particularly preferably the closure part 23 is made of butyl rubber.

The container 20, in particular portion 20B, is preferably made of a rigid material, in particular glass, metal or hard plastic, particularly preferably cyclic olefin polymers.

A sealing S1 is preferably formed between the preferably rigid container 20, in particular portion 20B, and the preferably flexible or deformable closure part 23, in particular neck 23C, particularly preferably in a gas- and/or liquid-tight manner.

Preferably, the closure part 23 is significantly softer than the container 20 or its edge or portion 20B.

The closure 21 or closure part 23 is preferably sealingly received or held in the container 20 or an opening thereof, here defined by the portion 20B or edge 20C.

Particularly preferably, the closure is self-locking and/or self sealingly connected with the container 20. This is in particular realized by the press/tight-fit or engagement of the closure 21 or closure part 23, in particular neck 23C, with the container 20, in particular portion 20B or edge 20C, or via versa.

The closure part 23 preferably comprises or forms an opening/channel 23D, in particular extending axially through the closure part 23.

Preferably, the longitudinal or central axis of the inner portion 23A runs through the opening 23D.

Particularly preferably, the closure part 23 or opening 23D is rotationally symmetric, preferably with the axis of rotation running through the opening 23D.

As already mentioned, the cartridge 3, in particular the container 20, is preferably at least essentially cylindrical and/or embodied as a hollow cylinder. Mostly preferred, the cartridge 3, in particular the container 20, is at least essentially rotationally symmetric and/or elongated.

The cartridge 3, in particular the container 20, preferably comprises or defines an axis A, preferably wherein the axis A is a longitudinal, central, motion and/or rotation axis of the cartridge 3, in particular the container 20.

The axis A preferably runs centrally through the cartridge 3, in particular the container 20, and/or the closure 21 or closure part 23, in particular its opening 23D. Preferably, the axis A forms a (common) central/longitudinal/rotational/motion axis of the container 20, closure 21 and/or closure part 23.

In the following—if not explicitly stated otherwise—spatial descriptions are in particular made with reference to the central axis A of the cartridge 3, in particular when radial and/or axial alignments or arrangements are specified. Thus, the terms "radial" or "axial" preferably relate to the axis A of the cartridge 3.

Preferably, the closure 21 further comprises a closure element 24.

The closure element 24 is preferably made of a rigid material, in particular hard plastic.

Preferably, the closure element 24 is injection-molded and/or formed as one piece.

Preferably, the closure part 23 is softer or more flexible than the closure element 24 so that these two components can form seals in between where desired and as explained later in more detail.

The closure element 24 is in particular movably arranged at or within the closure part 23 or opening 23D.

In particular, the closure element 24 is adapted to be moved/pushed axially, relatively to the closure part 23 and/or away from the holder 6 and/or towards the bottom of the cartridge 3 and/or with a stroke/distance D, in particular by means of the connecting element 9, as will be explained in the following.

The closure element 24 is preferably adapted to close the cartridge 3, in particular the closure 21, closure part 23 or opening 23D in an initial/closed position (shown in FIGS. 3 and 6) or initially, i.e. before use or connection to the nebulizer 1, and to establish a fluidical connection between cartridge 3 and nebulizer 1 in a connected/open position (shown in FIGS. 7 and 7A) or when in use.

Particularly preferably, a valve 29 is formed or comprised in or by the closure 21, in particular closure part 23 and closure element 24. In particular, the closure element 24 forms a movable valve member of the valve 29.

The valve 29 is preferably adapted to open when the connecting element 9 is inserted into or received by closure 21, closure part 23 or opening 23D.

The closure element 24 is preferably adapted to displace a displacement volume of fluid 2 from the container 20 into the delivery mechanism 5 and/or connecting element 9, in particular when being pushed by means of the connecting element 9.

The closure part 23, in particular opening 23D, is preferably adapted to receive the connecting element 9 and/or closure element 24.

Preferably, the closure part 23 forms or is a connection port for the connecting element 9.

Further aspects and features of the closure 21, in particular of valve 29, closure part 23, opening 23D and closure element 24 are explained in more detail further below in connection with FIGS. 4 to 11.

The cartridge 3 can further comprise a preferably flexible tube 25, in particular a capillary/dip/conveying tube, particularly preferred for suction and/or conveying of fluid 2 out of the container 20 and/or towards the delivery mechanism 5 or connecting element 9.

The tube 25 is preferably constructed as an elongated hollow cylinder or capillary.

Preferably, the tube 25 comprises a first axial or fixed end 25A and second axial or free end 25B, preferably wherein the first axial or fixed end 25A is fixed/attached to or formed by closure 21, closure part 23 or closure element 24 and/or the second axial or free end 25B is freely movable within the container 20 or fluid 2.

Preferably, embodiments of the present invention which comprise the tube 25 do not comprise the variable/collapsible volume 4, in particular the flexible/collapsible bag, in particular since the collapsing volume 4 could interfere with the tube 25 and/or limit its ability to freely move within container 20. Nevertheless, such embodiments might also incorporate a variable/collapsible volume 4.

Optionally, the cartridge 3 or tube 25 comprises an immersion/contact element 25C, e.g. a weight, a sponge, an anchor or the like, preferably wherein the immersion element 25C is attached to or formed by the tube 25, in particular its free end 25B.

In the embodiment shown in FIG. 3, the tube 25 and the immersion element 25C are preferably separate parts. Alternatively, tube 25 and immersion element 25C might be formed in one piece. For example, the wall thickness of the free end 25B of the tube 25 might be increased compared to the adjacent wall thickness. In this way, the free end 25B of tube 25 might form the immersion element 25C.

Preferably, the immersion element 25C is adapted to increase the weight force acting on the tube 25, in particular its free end 25B, causing bending of tube 25 in accordance with gravity and/or the spatial orientation of nebulizer 1 or cartridge 3. Further, the immersion element 25C preferably provides for the free end 25B and the walls of container 20 or volume 4 to be always spaced apart, in particular regardless of the spatial orientation, such that it is preferably prevented that the free end 25B sticks to or is blocked by said walls.

Preferably, the tube 25 is wettable and/or comprises an at least partially wettable, in particular hydrophilic and/or polar, surface. In particular, at least the free end 25B of tube 25 or the immersion element 25C comprises a partially wettable, in particular hydrophilic and/or polar, surface. However, it is preferred that the entire surface of tube 25 is wettable, in particular hydrophilic and/or polar.

Due to the hydrophilic and/or polar surface and/or polarity/wettability of tube 25, in particular free end 25B or immersion element 25C, the tube 25, in particular its surface, gets easily wetted with fluid 2 and/or, once wetted and/or immersed in the fluid 2, the tube 25, at least its free end 25B or immersion element 25C, is kept/pulled in the fluid 2, in particular due to adhesion and/or cohesion of the fluid 2. In this way it is preferably prevented that air is sucked into the delivery mechanism 5 of the nebulizer 1.

Preferably, the cartridge 3 comprises a base or base element 26. The base element 26 preferably closes the cartridge 3 or container 20 at the bottom or lower axial end or forms a bottom or base of the container 20. The base element 26 can be embodied as a separate part, as in particular shown in FIG. 3, or can be integrally formed or formed as one piece with the container 20.

When embodied as two separate parts, the base element 26 preferably fits snuggly into the lower axial end of the container 4, in particular the inner diameter of the container 20 at the lower axial end being at least essentially the same as the outer diameter of the base element 26.

The base element 26 can further comprise a portion radially protruding over the edge formed by the lower axial end of the container 20.

The base element 26 is preferably immovably fixed at the lower axial end of the container 20 by form-fit, tight-fit and/or bonding. In this case, the cartridge 3 preferably comprises the ventilation 22.

Alternatively, the base element 26 can be moveable axially and/or within the container 20, preferably towards the upper axial end or top of the cartridge 3, in particular forming a piston or plunger.

In this case, the base element 26 is preferably located at the lower axial end of container 20 in an initial position, i.e. with the cartridge 3 completely filled with fluid 2.

The volume 4 delimited by container 20, closure 21 and base element 26 in that initial position preferably defines the maximum filling volume of container 20. The variable or collapsible volume 4 is then preferably realized by the base element 26 moving axially upwards or in the direction of closure 21, thus decreasing/shrinking volume 4 during use. In this case, a ventilation 22 is not necessary.

A preferred embodiment comprising such a movable base element/piston 26 is further explained in detail below in connection with FIGS. 14, 16, 17 and 18.

Preferably, the container 20 or base element 26 is provided with a sealing element 26A acting between the base element 26 and the inner wall of the container 20, in particular to seal the base element 26 against the interior of the container 20 in a liquid- and/or gas-tight manner, as shown in FIG. 3. The sealing element 26A can be formed e.g. as a ring or lip and/or held by the base element 26. However, other constructional solutions are possible as well.

The base element 26 can further comprise the aeration/ventilation 22, in particular the aeration opening 22A and/or the cover 22B. In this case, the base element 26 does not have to be (axially) movable, so that the cartridge 3/container 20 may provide an invariable volume for the fluid 2.

Preferably, the cover 22B covers or seals the cartridge 3, container 20 or aeration opening 22A at the bottom or from below, at least initially. The cover 22B is preferably a foil or film attached to the bottom of the base element 26 and/or container 20.

Particularly preferably, the cover 22B is pierceable and/or breakable, in particular to open aeration/ventilation 22, for example by a piercing element 19A of the nebulizer 1 as explained in the outset.

The cartridge 2, aeration/ventilation 22 or base element 26 preferably comprises a (aeration) valve 22C.

The valve 22C is preferably embodied as a one-way valve, and/or allows gas, in particular air, to enter container 20 on the one hand and prevents fluid 2 to exit or escape container 20 via ventilation 22 on the other hand. A preferred embodiment of the valve 22C is shown in FIG. 3.

The valve 22C preferably comprises a valve member 22D and a valve seat 22E. The valve member 22D has a preferably disc-like portion with an at least essentially cylindrical portion protruding perpendicularly therefrom and/or being at least essentially T-shaped in cross section and/or umbrella-shaped.

Particularly preferably, the valve 22C is embodied as an umbrella valve.

The disc-shaped portion preferably rests on the valve seat 22E which is in particular formed by the base element 26. A gas connection between the outside and inside of cartridge 3 or container 20, in particular aeration opening 22A, is preferably covered or closed by the valve member 22D resting on the valve seat 22E.

The aeration opening 22A is preferably embodied as a bore hole in the base element 26, which opening is sealed by the valve member 22D when the valve 22C is closed.

The sealing surface of the valve 22C, i.e. the surface where the preferably umbrella-like valve member 22D is pressed onto the valve seat 22E, which is in particular formed by a flat surface of the base element 26, is preferably ring-shaped.

Normally, the pressure of the fluid 2 and/or a biased construction preferably presses the valve member 22D onto the valve seat 22E, such that the valve 22C is closed and no fluid 2 can escape through the valve 22C.

On the other hand, if low pressure occurs in container 20 when fluid 2 is conveyed out of the cartridge 3, the pressure difference between the outside and the inside of the container 20 forces air through ventilation 22, in particular through aeration opening 22A, in particular lifting the valve member 22D from valve seat 22E such that the air can get into container 20 for pressure equalization. When the pressure is equalized, valve member 22D rests again on valve seat 22E such that valve 22C is closed again.

At least for the direct gas connection or aeration, it is preferred that the ventilation 22 comprises a sterile filter 22F such that the fluid 2 does not get contaminated by impurities or foreign substances of the air or any other gas. For the indirect gas connection, e.g. when providing the flexible bag, the gas does not come into direct contact with the fluid 2 and a sterile filter 22F can be omitted. However, it is also possible to provide the ventilation 22 with a sterile filter 22F for the indirect gas connection.

The filter 22F is in particular arranged within aeration opening 22A and/or upstream (with regard to gas flowing into container 20) of valve seat 22E.

Figure 4:
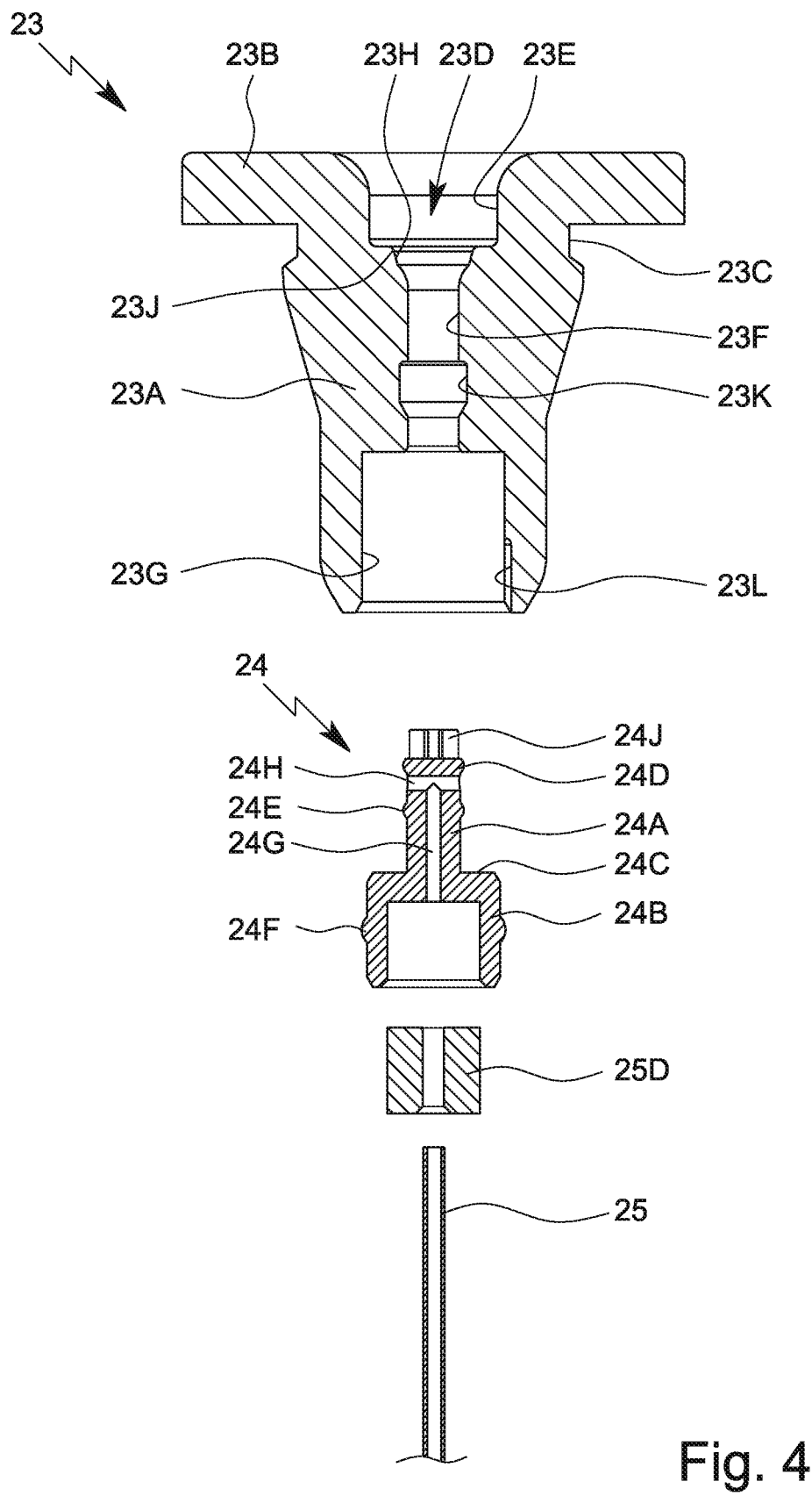
FIG. 4 is a schematic exploded view of a closure of the cartridge according to FIG. 3.
Figure 5:
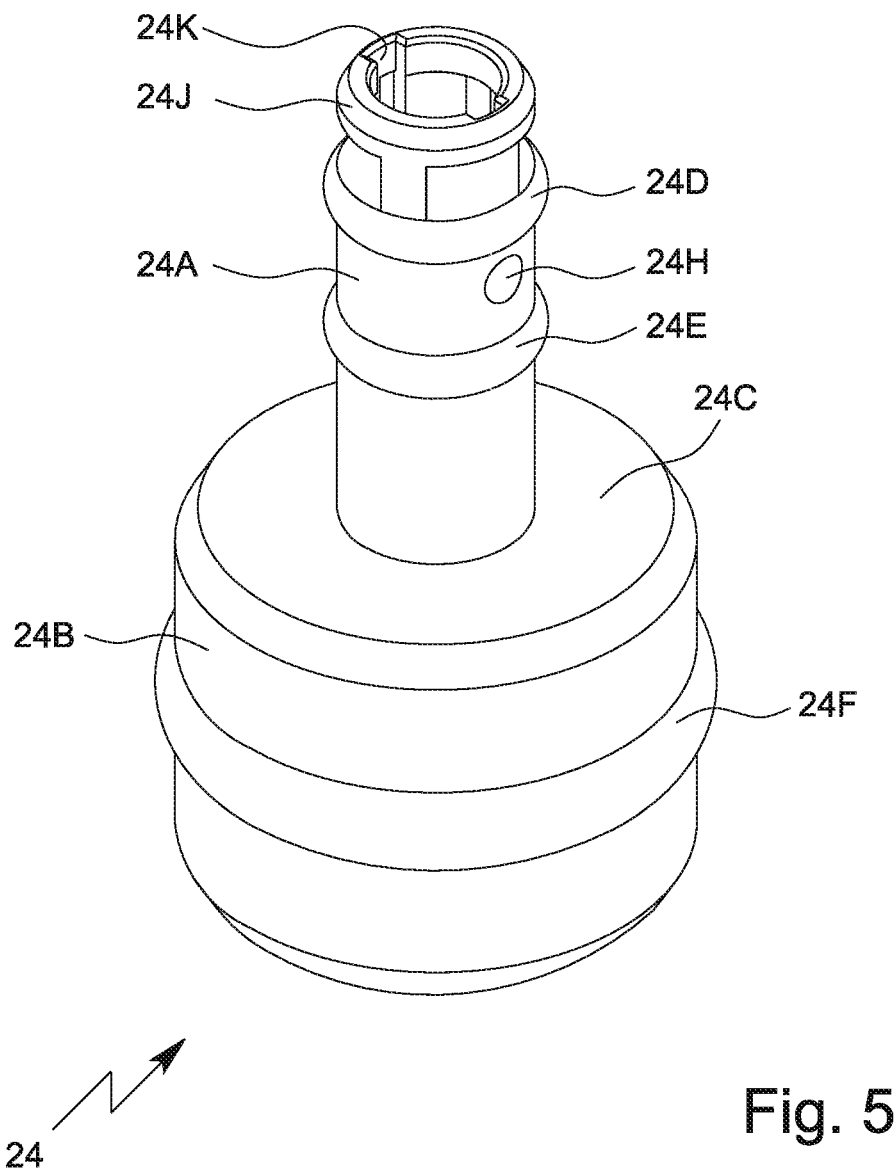
FIG. 5 is a schematic perspective view of a closure element of the cartridge according to FIG. 3.
Figure 6:
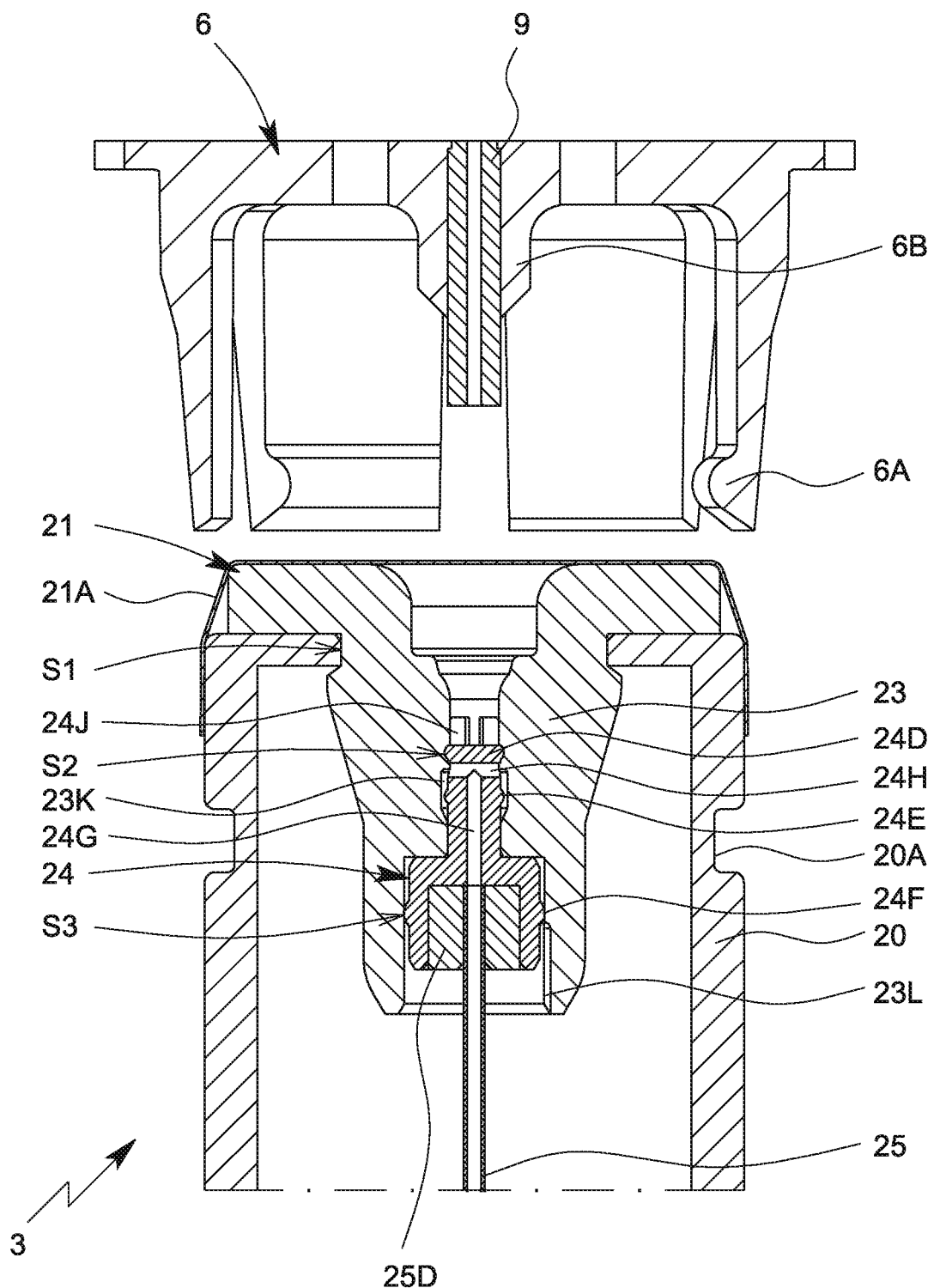
FIG. 6 is a schematic section of the cartridge according to FIG. 3 in the region of the closure before connection to the nebulizer.

FIG. 4 shows in a schematic exploded view the different parts of the closure 21, in particular closure part 23 and closure element 24. FIG. 5 is a perspective view of the closure element 24. FIG. 6 shows the upper portion of cartridge 3, in particular closure 21, before being connected to the nebulizer 1. It should be noted that for reasons of clarity, the fluid 2 is not explicitly depicted in FIG. 6 and subsequent figures.

Preferably, the longitudinal or central or symmetry axis of the closure 21 or closure part 23 runs through the opening 23D, in particular the closure part 23 or closure 21 being rotationally symmetric around said axis.

Preferably, the closure part 23 or opening 23D comprises a first portion 23E, a second portion 23F and/or a third portion 23G.

The first portion 23E opens preferably to the top of the closure part 23.

Particularly preferably, the first portion 23E comprises a funnel- or cone-shaped and/or tapered portion or surface 23H, at least in part, in particular the portion or surface 23H tapering to the second portion 23F.

The first portion 23E or surface 23H comprises preferably a sealing element 23J for providing a sealing S6 with the holder 6 or connecting element 9 when the cartridge 3 is inserted into the nebulizer 1 which will be explained in more detail below in connection with FIG. 7.

The second portion 23F is preferably at least essentially cylindrical.

The second portion 23F preferably comprises an annular channel portion 23K with a larger diameter than the rest of the second portion 23F.

Preferably, when the cartridge 3 is connected to the nebulizer 1 a conveying channel is formed in the channel portion 23K which will be explained in more detail below in connection with FIG. 7.

The third portion 23G is adapted to receive the closure element 24, in particular a displacement portion 24B thereof, and is preferably at least essentially cylindrical.

The diameter of the third portion 23G is preferably greater than the diameter of the first and/or second portions 23E, 23F. In particular, the diameter of the third portion 23G is two to four times greater than the diameter of the second portion 23F.

The closure element 24 is preferably arranged in the second and third portions 23F, 23G of the closure part 23 or opening 23D. In particular, different parts of the closure part 23 and the closure element 24 correspond to each other and/or are formed accordingly.

The closure element 24 is preferably integrally formed or formed as one piece.

Preferably, the closure element 24 comprises a control portion 24A and the displacement portion 24B. The portions 24A, 24B are preferably at least essentially cylindrical.

The outer diameter of the control portion 24A is preferably such that it fits into the second portion 23F. The outer diameter of the displacement portion 24B is preferably such that it fits into the third portion 23G.

In particular, the outer diameter of the control portion 24A is smaller than the diameter of the displacement portion 24B.

Preferably, an at least essentially annular shoulder or stop 24C is formed between the control portion 24A and displacement portion 24B.

The axial length of the control portion 24A preferably is at least essentially the same as the axial length of the second portion 23F.

The axial length of the displacement portion 24B is preferably smaller than the axial length of the third portion 23G.

FIGS. 3 and 6 show the closure 21, the closure valve 29 and the closure element 24 in the closed or initial position, which is the position before the cartridge 3 is inserted into nebulizer 1.

In the initial or closed position, the closure element 24 is preferably arranged or held in the closure part 23 or opening 23D, preferably by radial press fit, such that the displacement portion 24B is arranged in the upper part of the third portion 23G, in particular stop 24C abutting against a corresponding axial stop formed by the closure part 23 between the second and third portion 23F and 23G.

When the cartridge 3 is connected to the nebulizer 1 and/or when the connecting element 9 is inserted into or received by the closure ferential wall of channel portion 23K. In particular, no sealing is formed at sealing element 24E in the initial position.

The displacement portion 24B preferably comprises at least one ring-like portion with an enlarged diameter, preferably like a circumferential ridge, lip or bulge in particular with the diameter slightly bigger than the diameter of the third portion 23G, particular forming a sealing element 24F.

In the initial position, the sealing element 24F is preferably arranged in the third portion 23G such that a sealing S3 is formed in between. In particular, the preferably flexible closure part 23 or third portion 23G is stretched apart by the preferably rigid sealing element 24F so that an at least substantially fluid-tight sealing S3 is formed.

Preferably, in the initial or closed position, the at least two separate sealings S2, S3 are provided or formed between the closure part 23 and the closure element 24.

If the cartridge 3 comprises the optional tube 25, the tube 25 is preferably connected to the closure element 24. In particular, the closure element 24 or displacement portion 24B can comprise holding means, such as a recess for receiving or holding an intermediate piece 25D.

The intermediate piece 25D is preferably attached to or integrally formed with the fixed end 25A of tube 25. Alternatively, tube 25 and intermediate piece 25D are separate parts which are connected by force-fit, form-fit, tight-fit and/or bonding.

The intermediate piece 25D is preferably connected with the closure element 24, in particular held in the recess formed in the displacement portion 24B, by force-fit, form-fit, tight-fit and/or bonding, and/or is integrally formed with the closure element 24.

Alternatively, the tube 25 can be connected directly to the closure element 24, in particular without an intermediate piece 25D.

The closure element 24 preferably comprises a vertical or axial or connecting channel 24G and/or a horizontal or radial or distribution channel 24H for guiding the fluid 2 from the cartridge 3/container 20/volume 4 to the valve 29 and/or connecting element 9 and/or into the opening 23D or its second/central portion 23F or the channel portion 23K. In particular, the channels 24G and 24H are transversally to each other.

At its lower axial or inner end, the axial channel 24G preferably is fluidically connected with the tube 25, the volume 4 or the container 20.

At its upper axial end, the axial channel 24G preferably discharges into the radial channel 24H, which, in turn, guides the fluid 2 outwards or out of the closure element 24.

The radial channel 24H is preferably located in the control portion 24A, and particularly preferably opens between the sealing elements 24D and 24E.

The radial channel 24H preferably discharges into the opening 23D, in particular second portion 23F or channel portion 23K, particularly preferably at the circumferential outer wall of the closure element 24 or its control portion 24A and/or on two opposing sides.

Thus, in the initial or closed position, fluid 2 can preferably flow through channels 24G and 24H into the opening 23D, in particular second portion 23F or channel portion 23K.

Preferably, in the initial or closed position, flow of fluid 2 into the first portion 23E is prevented by the sealing S2 (which provides the valve function of the valve 29 when closed) and/or no fluid 2 can flow past sealing element 24D.

Thus, fluid 2 is preferably prevented from escaping the cartridge 3 through the closure 21 or opening 23D in the initial or closed position.

The closure element 24 comprises optionally a coupling element or socket 24J at its upper axial or outer end. The socket 24J is preferably provided for filling the cartridge 3 with fluid 2 and/or for closing valve 29 after it has been opened, which is described in more detail below in connection with FIGS. 8 to 11.

Figure 7:
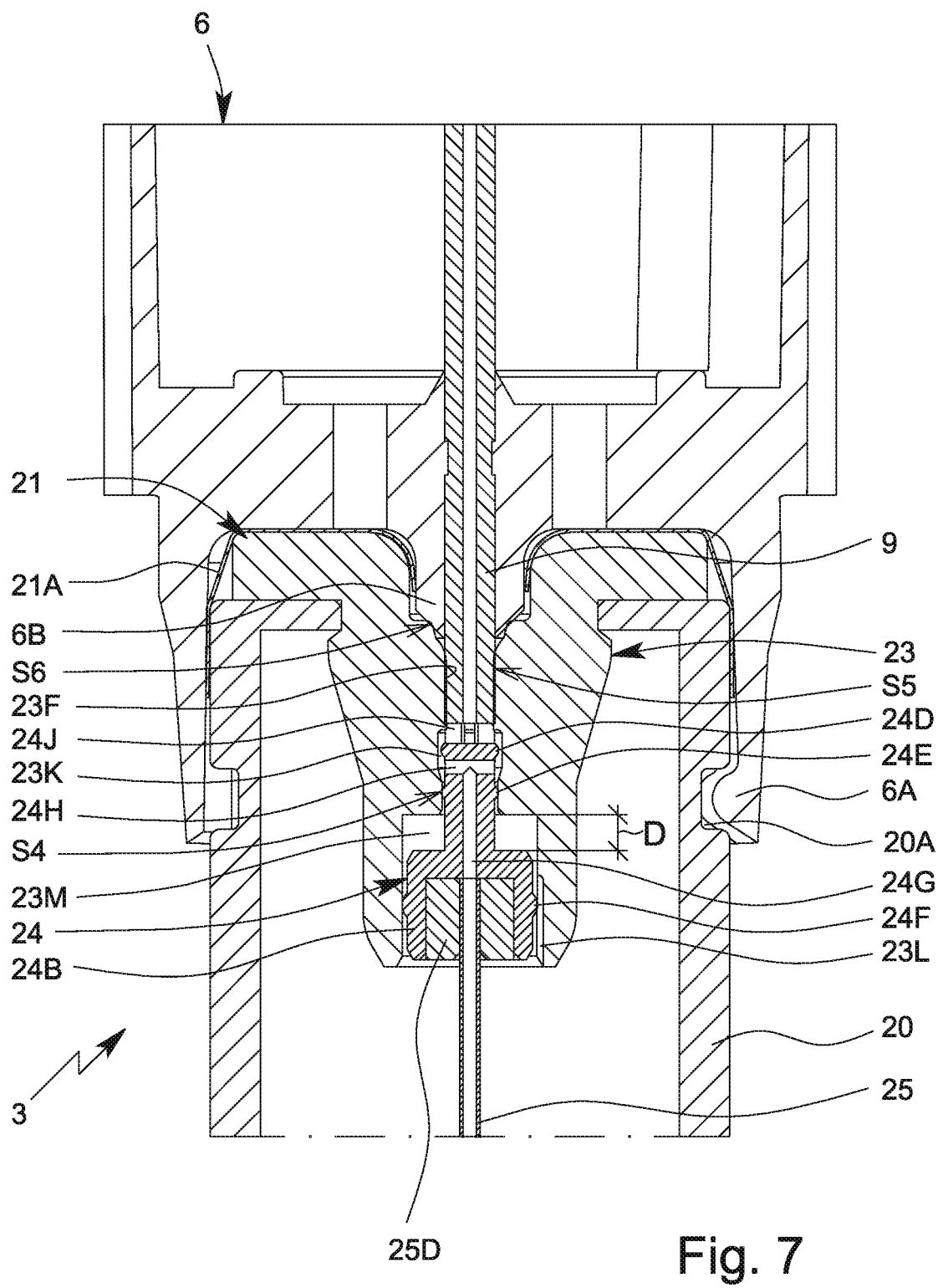
FIG. 7 is a schematic section of the cartridge according to FIG. 3 in the region of the closure connected to the nebulizer.
Figure 7A:
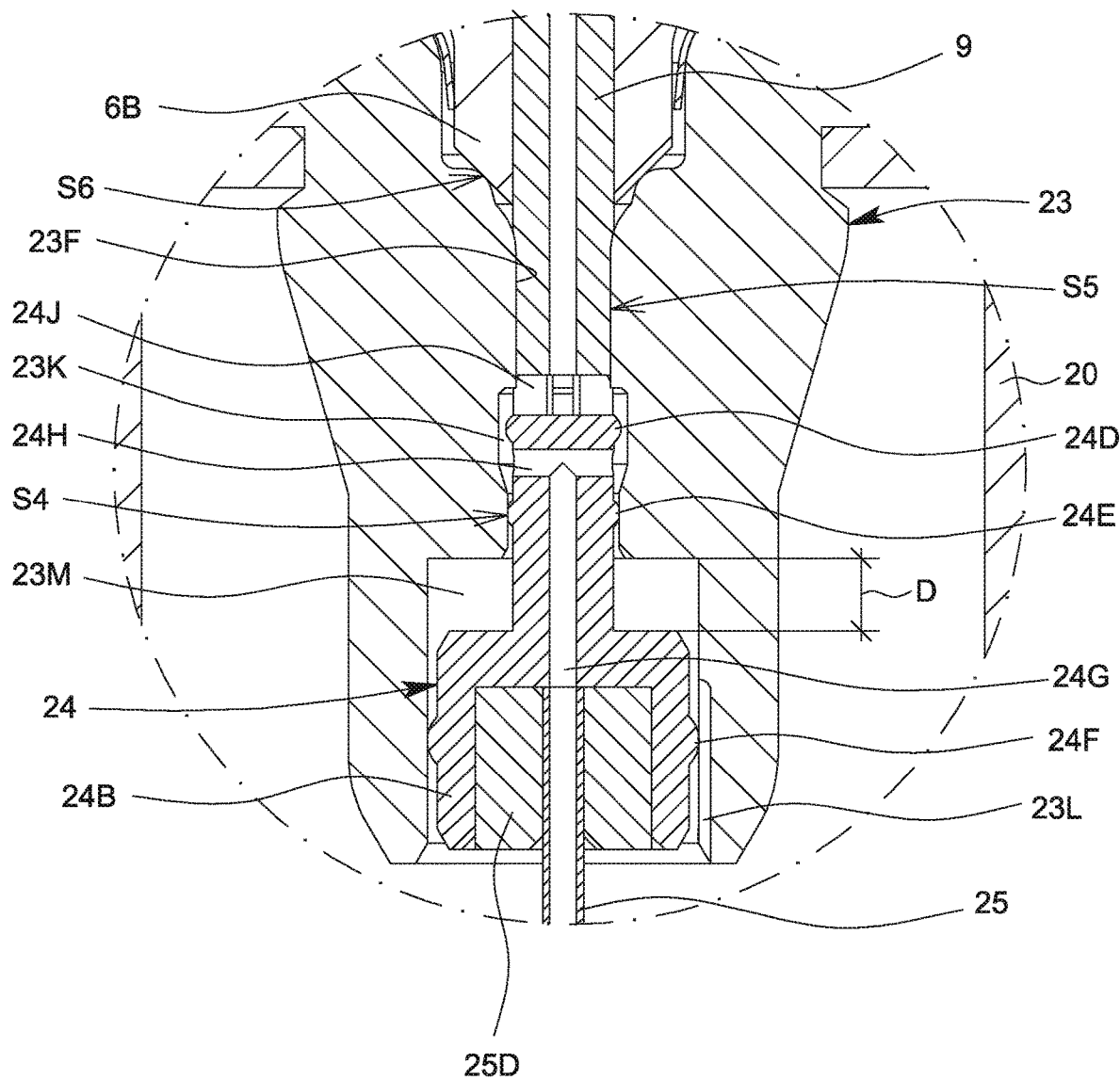
FIG. 7A is an enlargement of FIG. 7 in the region of the closure element.

FIG. 7 shows the cartridge 3 when being connected to the nebulizer 1 in a schematic section similar to FIG. 6. FIG. 7A is an enlargement of FIG. 7 in the region of the closure element 24.

When the cartridge 3 is connected to the nebulizer 1, in particular to the holder 6 thereof, the connecting element 9 preferably pierces or breaks the cover 21A, if provided, and is inserted or pushed into or received by the closure 21, in particular closure part 23 or opening 23D.

In the completely connected state shown in FIG. 7, the holder 6 mechanically holds the cartridge 3 preferably by means of holding arms or portions 6A engaging into the recess 20A of the container 20.

Preferably, the cartridge 3, in particular closure part 23 and/or second portion 23F, is adapted to sealingly receive the connecting element 9, preferably adjacent to its axial end, in a press/tight fit manner such that a sealing S5 is formed between the closure part 23 and the connecting element 9 and/or such that a fluidic and/or tight connection between cartridge 3 and the delivery mechanism 5 can be established (as shown in FIG. 7).

Mostly preferred, the (flexible) closure part 23 or second portion 23F is (laterally) expanded by the connecting element 9, in particular such that the closure part 23 or second portion 23F encompasses the connecting element 9 in a liquid- and/or gas-tight manner. Thus, radial tolerances of the connecting element 9 can preferably be compensated.

In particular, the second portion 23F is flexible, deformable and/or stretchable, at least in part, and has a diameter smaller than the outer diameter of the connecting element 9. Upon insertion of the connecting element 9, the second portion 23F can flex/deform/stretch such that the sealing S5 is formed between the connecting element 9 and the closure part 23, in particular second portion 23F.

Alternatively or additionally, a separate or other sealing S6 is formed or established which is spaced apart from sealing S5. In particular, the sealing S6 is formed or established at or with the closure 21 or closure part 23, preferably with first portion 23E, tapered portion 23H or sealing element 23J on one hand and preferably with holder 6 or a contact or sealing portion 6B thereof on the other hand.

The tapered surface 23H preferably forms an angle with the longitudinal or central axis running through closure part 23 or opening 23D between 5° and 85°, in particular between 30° and 60°. However, also structural solutions where the angle is about 90° and/or where the surface 23H is at least essentially horizontal in the normal upright position are possible here.

Preferably, the connecting element 9 or holder 6 comprises the contact or sealing portion 6B which is adapted to enter or being received by the closure part 23 or opening 23D, in particular first portion 23E.

Sealing portion 6B is preferably pressed onto surface 23H or sealing element 23J when the cartridge 3 is (completely) inserted into holder 6 and/or when the connecting element 9 has been (completely) received by closure 21.

The sealing portion 6B preferably has or forms an abutment surface for abutment with or against the tapered surface 23H or sealing element 23J.

The second or other sealing S6 is preferably oriented in a different direction than the first or radial sealing S5.

Particularly preferably, the closure part 23, which is integrally formed or formed as one piece, forms both sealing S1 to the container 20, in particular portion 20B, on the one hand, and sealing S5 to the connecting element 9 and/or sealing S6 to the holder 6 on the other hand.

When inserting the connecting element 9, it preferably abuts on the socket 24J. The inner diameter of socket 24J is preferably smaller than the outer diameter of connecting element 9, in particular such that the connecting element 9 does not enter socket 24J.

The connecting element 9 preferably pushes or presses the closure element 24 axially downwards or further into the cartridge 3 or towards the fluid 2, base element 26 and/or lower axial end of cartridge 3 or container 20.

When pushed, the closure element 24 is preferably moved such that its sealing element 24D is moved into the channel portion 23K and/or to open or break the sealing S2 so that the closure 21 or valve 29 is opened.

Here, the diameter of the channel portion 23K is greater than the diameter of sealing element 24D, in particular such that no new sealing is formed by the sealing element 24D in the second or open position shown in FIG. 7.

Particularly preferably, a channel is formed between the sealing element 24D and the channel portion 23K. In particular, the fluid 2 can flow through the channels 24G and 24H and around the sealing element 24D via said newly formed channel.

In particular, the fluid 2 can flow around the sealing element 24D and preferably via socket 24J into the connecting element 9. Thus, a fluidic connection is formed or established between cartridge 3, container 20 or tube 25 on the one hand and the nebulizer 1, delivery mechanism 5 or connecting element 9 on the other hand.

Thus, the closure element 24 and the closure part 23 preferably form or comprise the valve 29, in particular the closure element 24 or its sealing element 24D acting as a movable valve member and the second portion 23F acting as a valve seat.

Initially, the valve 29 is closed by the sealing element 24D pressing against the second portion 23F, in particular forming a sealing S2 in between. The valve 29 is preferably opened by the connecting element 9 pushing the closure element 24. Preferably, the sealing element 24D is moved away from the valve seat or second portion 23F in the axial direction, such that sealing S2 is broken and valve 29 is opened.

Preferably, when the closure element 24 is moved and/or the valve 29 is opened, the sealing element 24E moves out of the channel portion 23K and into the lower part of the second portion 23F, preferably wherein a sealing S4 is formed or established between the control portion 24B or sealing element 24E and the second portion 23F or inner portion 23B.

In particular, the sealing element 24D is moved from the second portion 23F into the channel portion 23K and simultaneously the sealing element 24E is moved from the channel portion 23K into the lower part of the second portion 23F, preferably such that the sealing S2 is broken and simultaneously or before or afterwards the sealing S4 is formed or established.

Particularly preferably, the valve 29 or this process or operation is reversible.

When the closure element 24 is moved axially in the opposite direction, sealing element 24E is moved out of the second portion 23F and into channel portion 23K and sealing element 24D is moved out of channel portion 23K and into second portion 23F. In particular, sealing S4 is broken and sealing S2 is formed or (re)established. Preferably, valve 29 is closed again by reestablishing sealing S2.

Preferably, the same portion of the closure part 23, in particular of second portion 23F, which initially forms sealing S2 with closure element 24, in particular with sealing element 24D, forms sealing S5 with the connecting element 9 after insertion or receiving thereof. In other words, when the connecting element 9 is inserted or received, sealing S2 is preferably replaced by sealing S5.

When the connecting element 9 is inserted into or received by the closure 21, closure part 23 or opening 23D, the closure element 24, in particular displacement portion 24B and/or connecting piece 25D, is pushed or moved (further) into the cartridge 3, container 20, volume 4 or fluid 2 to displace the displacement volume.

Accordingly, the displacement volume of fluid 2 is displaced into nebulizer 1, in particular connecting element 9, pressure chamber 11 and/or delivery mechanism 5.

Preferably, when the closure element 24 displaces the displacement volume, the valve 29 opens simultaneously or immediately before displacement of fluid 2. However, it is also possible that valve 29 opens during or at the end of the displacement.

The end position of the closure element 24 is preferably the position of the closure element 9, when the connecting element 9 has been completely inserted. Preferably, the end position of the closure element 24 depends on the length and/or variation in length of the connecting element 9 and, thus, can vary accordingly.

Preferably, the closure element 24 does not have to be pushed to the axial end of the closure part 23 in order to reach its end position, but rather may be (still) axially spaced apart from the axial end of the closure part 23 in its end position. However, it is also possible that the closure element 24 sits at least essentially flush with the axial end of the closure part 23 and/or protrudes into the volume 4 when reaching its end position.

Preferably, a chamber 23M above the displacement portion 24B or stop 24C will form when the closure element 24 is pushed down. Due to the sealing S3, preferably no fluid 2 can enter said chamber 23M during the downward movement of closure element 24. Hence, in this case, a low pressure or vacuum is created in said chamber 23M.

To relieve or compensate said low pressure or vacuum and/or to equalize the pressure, preferably a bypass 23L is provided in the closure part 23 or third portion 23G.

The bypass 23L is preferably formed as an axially extending channel or groove and/or as a channel-like notch, recess or indentation in the side wall of the third portion 23G.

The bypass 23L is preferably constructed such that fluid 2 can bypass the sealing element 24F via the bypass 23L and flow into the chamber 23M when or just before the connecting element 9 is (completely) inserted or received and the closure element 24 reaches its completely open or lower end position.

In particular, a fluidical connection to the chamber 23M is only established or the bypass 23L only opens shortly before complete displacement of the displacement volume or closure element 24. In particular, the axial length of bypass 23L is chosen accordingly.

In this way it is ensured that overpressure in the container 20 and/or displacement of fluid 2 into the nebulizer 1 is maintained during movement of closure element 24, in particular such that the overpressure is not compensated by fluid 2 being displaced into the chamber 23M.

However, it is also possible that opening of the bypass 23L or establishing a fluidical connection to the chamber 23M takes place already before the connecting element 9 is completely inserted or before the closure element 24 has reached its end position. Preferably, when moving the closure element 24 further down, after the bypass 23L has opened, fluid 2 is still displaced into the nebulizer 1/delivery mechanism 5/connecting element 9. In particular, the bypass 23L is small enough that a sudden pressure increase, caused by movement of the closure element 24, causes fluid 2 to be displaced into the nebulizer 1/delivery mechanism 5/connecting element 9 instead of chamber 23M.

Preferably, after the connecting element 9 has been completely inserted and/or after the closure element 24 has reached its end position, fluid 2 flows into the chamber 23M via the bypass 23L, thereby compensating the low pressure or vacuum created.

Preferably, the chamber 23M is fluidically connected to the volume 4 of the cartridge 3 by means of the bypass 23L when the closure element 24 is in and/or reaches the end position.

Preferably, no fluid 2 flows back from the delivery mechanism 5 and/or connecting element 9 into the cartridge 3 or container 20 when the bypass 23L opens and/or when fluid 2 flows into the chamber 23M. This is preferably achieved by the ventilation 22, in particular in the case of a direct gas connection by air or another gas entering the container 20 or cartridge 3 in particular via valve 22C, the air or other gas replacing the fluid 2 which has been displaced. Alternatively, fluid 2 flowing back from the delivery mechanism 5 and/or connecting element 9 into the cartridge 3 or container 20 can be prevented by the variable/collapsible volume 4 shrinking in case of indirect volume compensation when withdrawing fluid 2 from the cartridge 3.

Alternatively, the closure 21 can be embodied such that no chamber 23M creating a low pressure is formed, in particular the connecting element 24 having at least essentially a constant diameter over its entire axial length and the closure part 23 having an accordingly formed opening 23D. Also, the connecting element 9 can have such an enlarged diameter at least at its lower axial end.

Preferably, the cartridge 3, in particular the closure 21, is adapted to compensate length tolerances of the connecting element 9 and/or to sealingly receive connecting elements 9 with different lengths.

Length tolerances of the connecting element 9 can in particular be compensated by the closure element 24, in particular by moving the closure element 24 axially and/or by axially elastic or deformable constructions, e.g. of the socket 24J.

Preferably, the sealings S5, S6 between the connecting element 9 or holder 6 on the one hand and the closure part 23 on the other hand can be established, even when using connecting elements 9 with different lengths and/or when moving the connecting element 9 axially, as the connecting element 9 is laterally/radially sealingly received by and/or connected with the closure part 23. In this way, length tolerances of the connecting element 9 can be compensated.

Preferably, all the above-mentioned aspects and features also apply for the connecting element 9 having a different (insertion) length. In particular, valve 29 is adapted to open for connecting elements 9 of different (insertion) length.

Preferably, the closure 21, in particular its closure part 23 and/or closure element 24, is/are adapted such that the sealings between the closure part 23 and the closure element 24 can be established or broken as described above for connecting elements 9 of different (insertion) lengths.

In particular, sealing S4 is formed/established and/or sealings S2 and S3 are broken also for shorter connecting element 9, when the cartridge 3 is connected to the delivery mechanism 5. Thus, in order to break sealing S3, the axial stroke D of the closure element 24 is preferably at least the initial distance (distance in the initial/delivery state of the cartridge 3) between the sealing element 24F and the upper end of the bypass 23L.

Further, the displacement volume is preferably large enough such that at least about one dose of fluid 2 is displaced, even if only a shorter axial stroke D of the closure element 24 is performed.

Figure 8:
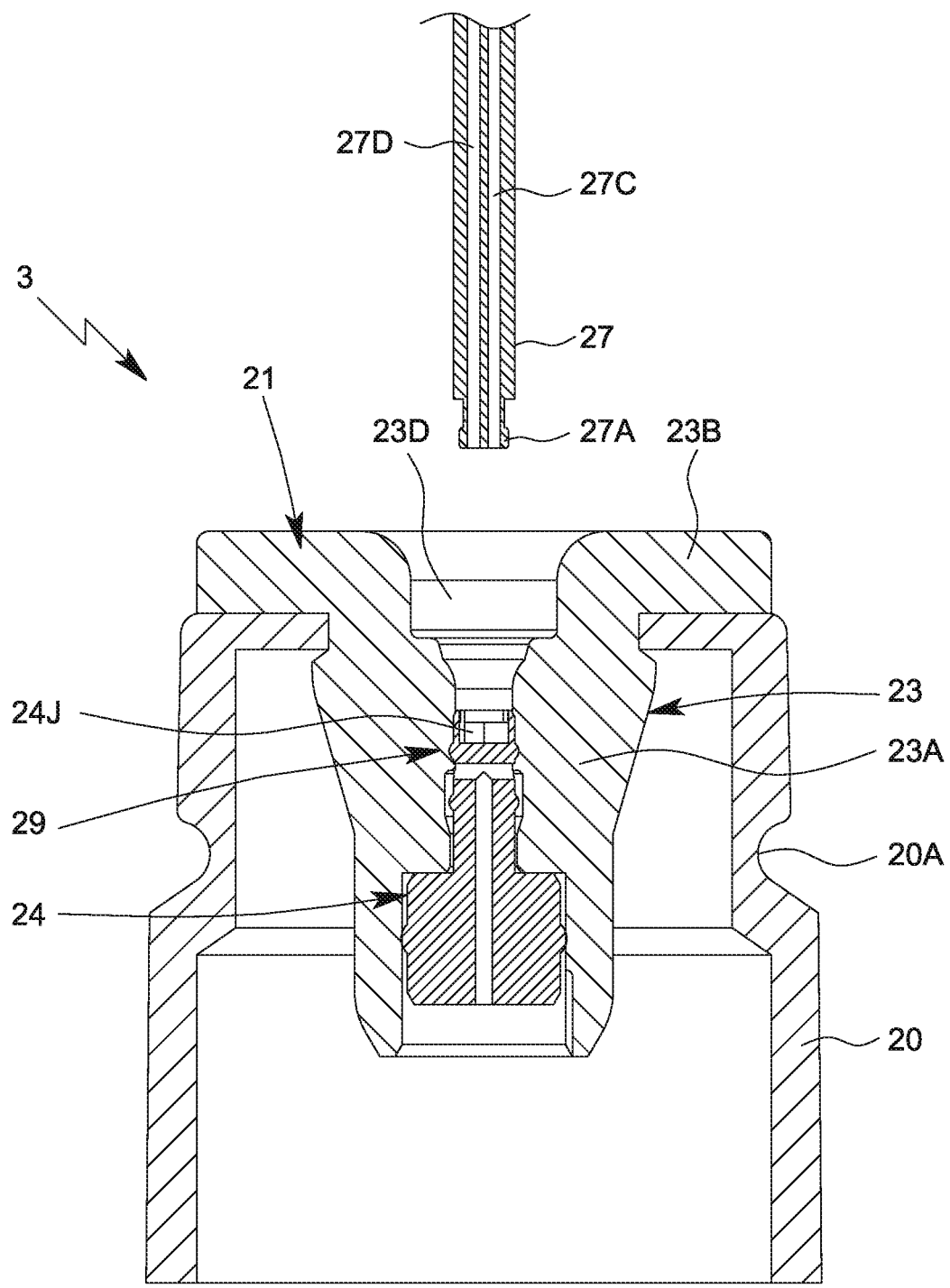
FIG. 8 is a schematic section of a variation of the cartridge according to FIG. 3 before being filled with fluid.
Figure 9:
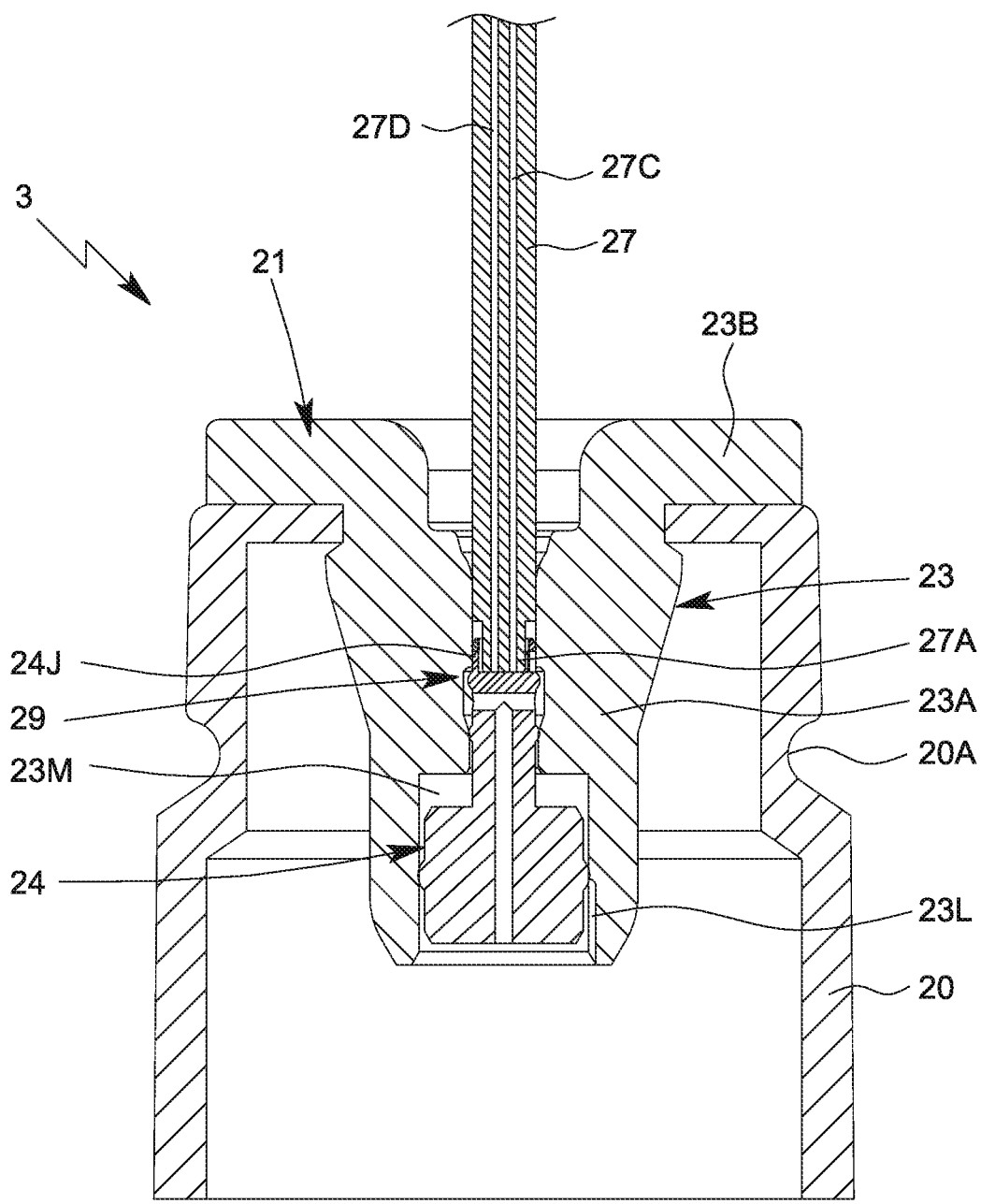
FIG. 9 is a schematic section of the cartridge according to FIG. 8 when being filled with fluid.

FIGS. 8 to 11 illustrate how the cartridge 3 can be filled with fluid 2. FIG. 8 shows in a schematic section the cartridge 3 before being filled with fluid and FIG. 9 shows the cartridge 3 during the filling process (the fluid 2 is not shown).

Figure 10:
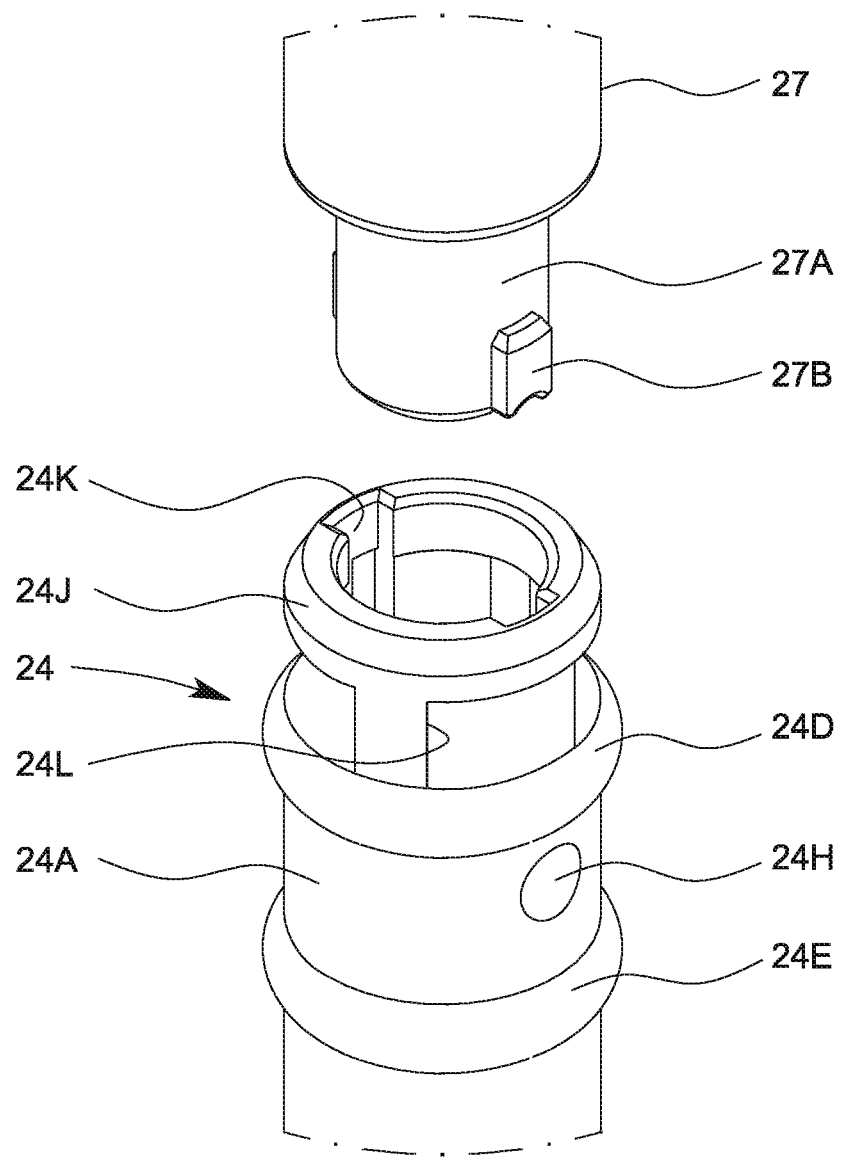
FIG. 10 is a schematic partial perspective view of a closure element of the cartridge before connection to a filling element according to FIG. 8.
Figure 11:
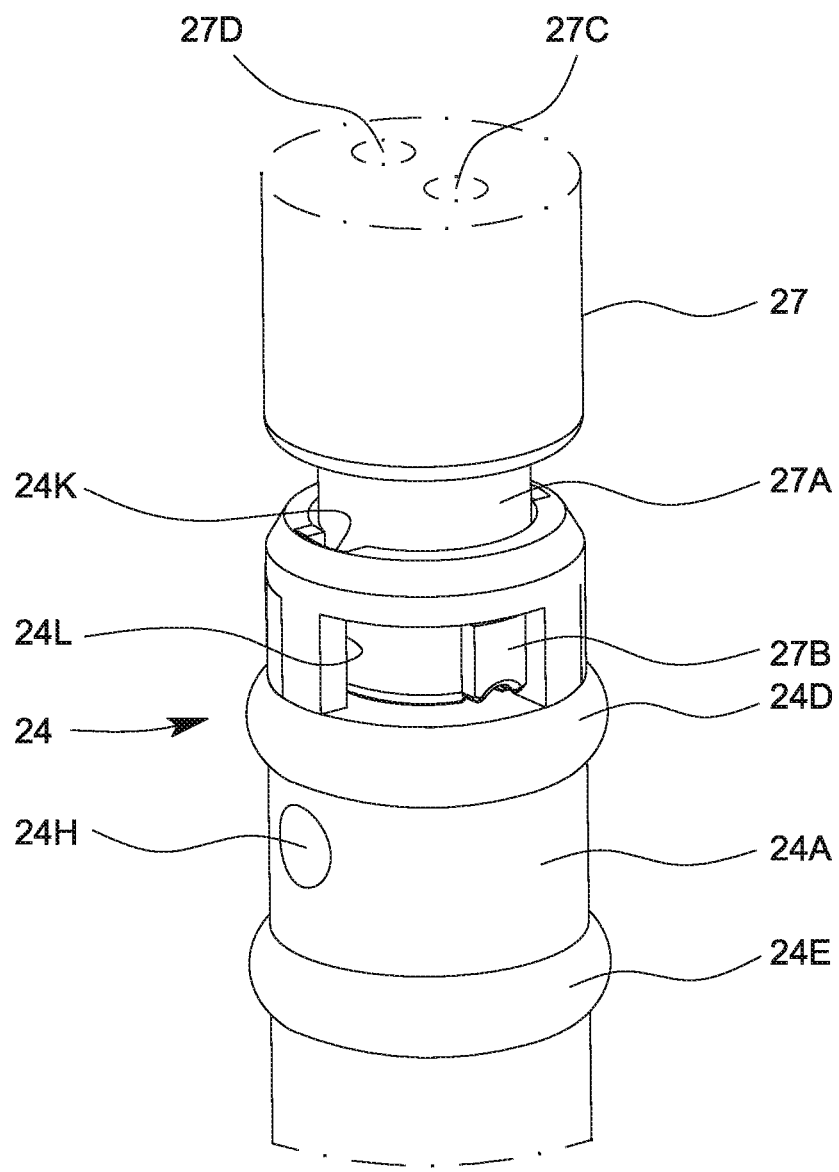
FIG. 11 is a schematic partial perspective view of the closure element when connected to the filling element according to FIG. 9.

Additionally, FIGS. 10 and 11 are perspective views showing how a filling element 27 can be connected with the closure element 24 for filling. FIG. 10 shows the upper part of closure element 24 together with filling element 27 before being connected and FIG. 11 shows closure element 24 and filling element 27 when connected.

Cartridge 3 is preferably filled with the fluid 2 from the top, in particular via closure 21. In particular, the cartridge 3 can be filled with the fluid 2 when the closure 21 has been mounted on the container 20 and/or when the cartridge 3 has already been at least essentially assembled.

Particularly preferably, the cartridge 3, container 20 or volume 4 can be filled with fluid 2 through the closure 21, in particular through the opening 23D. In particular, no parts of the cartridge 3 need to be removed for filling.

Filling of the cartridge 3 is preferably performed with a filling element 27 which is preferably hollow and/or elongate.

The filling element 27 preferably comprises a head 27A which in particular forms or comprises an outlet for the fluid 2 to be filled and/or an inlet for air or another gas contained in cartridge 3 before filling.

Preferably, fluid 2 can be conveyed through the filling element 27 and can be dispensed at the outlet or head 27A.

The head 27A can preferably be detachably connected with the closure element 24, in particular socket 24J, particularly preferably by form-fit in axial direction.

Preferably, the head 27A has an outer diameter that corresponds to the inner diameter of socket 24J, in particular such that head 27A fits into socket 24J.

Particularly preferably, socket 24J and head 27A are embodied as a bayonet mount.

The socket 24J preferably comprises at least one vertical or axial slot 24K and at least one circumferential slot 24L. In particular, circumferential slot 24L joins with the lower axial end of axial slot 24K. The circumferential slot 24L can for example be embodied as a recess in socket 24J, as in particular shown in FIGS. 10 and 11.

The head 27A preferably comprises one or more radial pins 27B which correspond to or match with the slots 24K, 24L.

When the filling element 27 is connected with the closure element 24, the head 27A is inserted in socket 24J with the at least one pin 27B sliding into the at least one axial slot 24K. By rotating the filling element 27, for example by 90°, the pin 27B rotates across the circumferential slot 24L.

In this way, pin 27B is preferably fixed in the slot 24L, at least against axial movement.

After connecting filling element 27 with closure element 24 it is preferably not possible to detach them by vertical or axial movement. Rather, for detaching, filling element 27 has to be rotated back to the position where pin 27B lines up with the vertical slot 24K and subsequently moved away from closure element 24 in the axial or vertical direction.

For filling, the filling element 27 is preferably connected to closure element 24 and then pushed axially downwards or in the direction of the bottom of cartridge 3 or container 20. The closure element 24 is then pushed downwards by the filling element 27, in particular in a similar manner as described in connection with FIG. 7.

In particular, by pushing or moving the filling element 27 in the axial direction, valve 29 opens or is opened. Thus, a fluidical connection between filling element 27 and cartridge 3, volume 4 or container 20 is formed or established. Fluid 2 can preferably enter cartridge 3, volume 4 or container 20 via the fluidical connection established within closure 21.

Preferably, the closure element 24 is not pushed down or moved as far as in the case when being connected to the nebulizer 1. Preferably, for filling, the bypass 23L remains closed, such that during filling no fluid 2 can enter the chamber 23M. This preferably ensures that the closure element 24 can move back into its initial position, without fluid 2 contained in the chamber 23M blocking or preventing such a movement.

For filling the cartridge 3, volume 4 or container 20 with fluid 2, any air or other gas contained therein needs to be removed. This can either be done before the filling is started or as a first step of the filling process, in particular creating a vacuum in cartridge 3, volume 4 or container 20.

Alternatively, removal of air or other gas contained in cartridge 3, volume 4 or container 20 can be performed during the filling process, in particular replacing the air or other gas gradually by the fluid 2. This can for example be achieved if ventilation 22 is embodied such that it works in both directions, in particular allowing gas to exit the cartridge 3 for filling and to enter the cartridge 3 when fluid is conveyed out of cartridge 3.

Particularly preferably, removing air or another gas from cartridge 3, volume 4 or container 20 during filling, in particular gradually replacing the air or other gas by the fluid 2, is realized by the filling element 27 having at least two separate channels 27C, 27D. In particular, one channel 27C is used for conveying fluid 2 through filling element 27 into cartridge 3 and the other channel 27D is used for conveying the air or other gas out of the cartridge 3, in particular simultaneously.

When cartridge 3, volume 4 or container 20 is at least essentially completely filled with fluid 2 or shortly before, the filling element 27 is preferably moved in the axial or vertical direction away from the cartridge 3. The closure element 24 is preferably moved in the same direction or upwards, in particular due to the preferably form-fit engagement of filling element 27 and closure element 24.

Filling preferably continues while the filling element 27 is moved away, in particular to ensure that the cartridge 3 is completely filled with fluid 2.

When the closure element 24 has moved back into its initial or closed position, filling is preferably stopped or completed, in particular cartridge 3, volume 4 or container 20 being (completely) filled with fluid 2, in particular including displacement volume.

Then, the filling element 27 is preferably detached from closure element 24, in particular the head 27A being detached from the socket 24J by rotation of the filling element 27 in the manner described above.

When the closure element 24 has moved back into its initial position, the valve 29 is preferably closed again such that the cartridge 3, volume 4 or container 20 is sealed against the environment.

After filling is completed and the filling element 27 has been removed, cartridge 3 or closure 21 can be provided with the cover 21A for additional sealing or protection.

In the following, further embodiments of the nebulizer 1 and/or cartridge 3 are described with reference to FIGS. 12 to 21 focusing on differences in comparison to the previously described embodiment. However, the previous aspects, features and explanations apply preferably additionally or correspondingly even without repetition if not explicitly stated otherwise.

Figure 12:
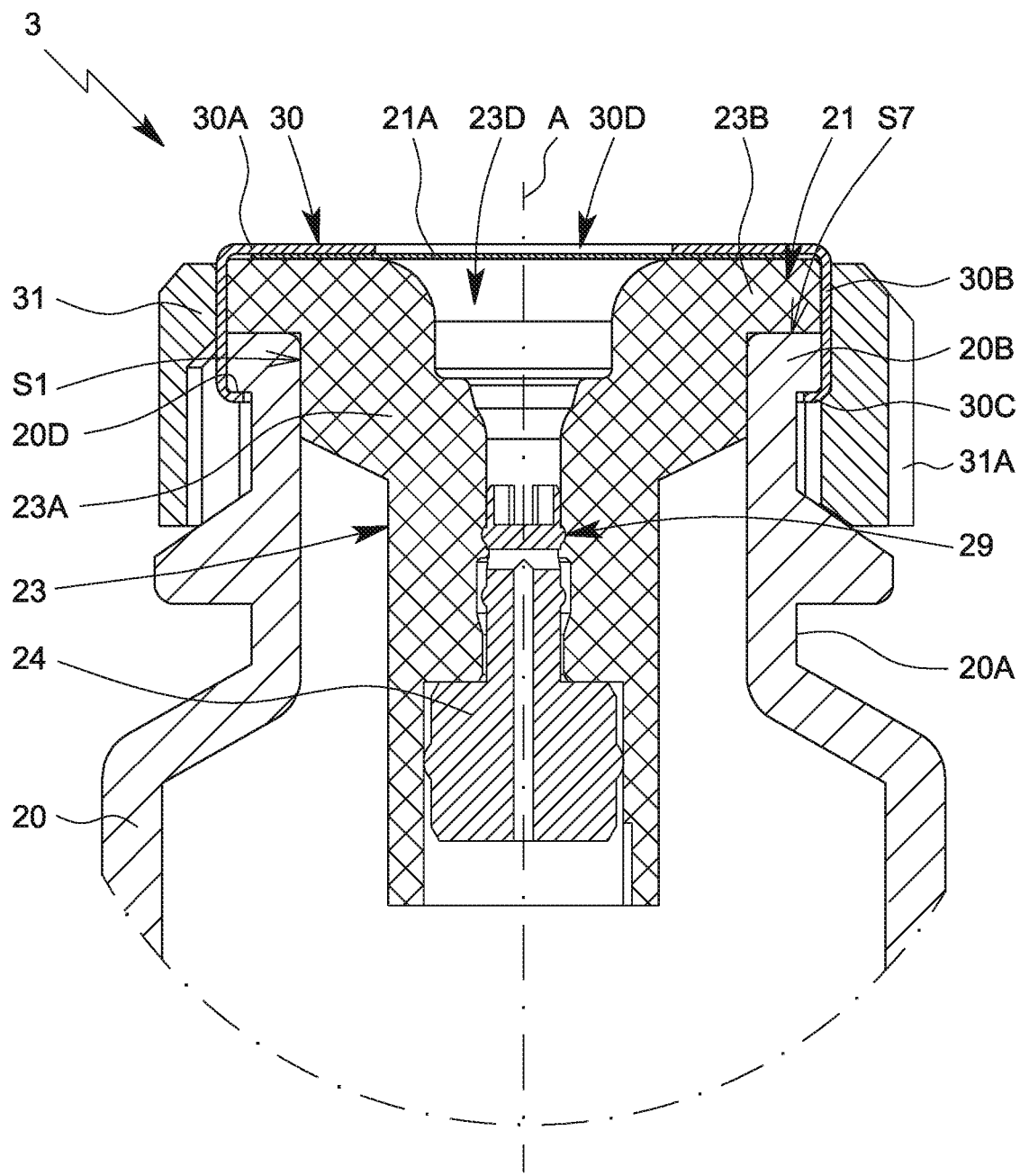
FIG. 12 is a schematic section of the cartridge in the region of the closure according to a second embodiment.

FIG. 12 shows the cartridge 3 in the region of the closure 21 in a schematic section according to a second embodiment of the present invention.

According to the second embodiment, the cartridge 3 or closure 21 preferably comprises a securing element 30.

The securing element 30 is preferably provided or adapted to secure, hold or fix the closure 21 or closure part 23 to the container 20. Particularly preferably, the securing element 30 secures, holds or fixes the closure 21 or closure part 23 in the axial direction and/or in a sealing and/or form-fit manner.

The securing element 30 is preferably attached to the axial end of the container 20, in particular its portion 20B. Mostly preferred, the securing element 30 forms the axial end of the cartridge 3.

The securing element 30 is preferably formed as a cap or cover, in particular covering the closure 21 or closure part 23 radially and/or axially.

Preferably, the securing element 30 comprises a top portion 30A, a side portion 30B and/or a securing portion 30C.

The securing element 30 is preferably integrally formed or formed as one piece.

Preferably, the top portion 30A forms a front side and/or axial end of the cartridge 3 and/or rests axially on top of the closure 21 or closure part 23, in particular its outer portion 23B, and/or extends at least essentially in the radial direction, horizontally in the normal operating position and/or at least essentially perpendicular to the axis A of the cartridge 3 or container 20.

Preferably, the side portion 30B forms a shell surface of the securing element 30 and/or covers the closure 21 or closure part 23, in particular its outer portion 23B, and/or the top/end of the container 20, in particular its portion 20B, radially and/or from the side. Preferably, the side portion 30B extends at least essentially in the axial direction, vertically in the normal operating position and/or at least essentially parallel to the axis A of the cartridge 3 or container 20.

In particular, the side portion 30B is circumferential and/or (radially) encompasses the closure 21 or closure part 23, in particular its portion 23B, and/or the container 20, in particular its portion 20B.

Preferably, the securing element 30, in particular its side portion 30B, fixes or secures the closure 21 or closure part 23, in particular portion 23B, radially, in particular in addition to the press-fit between closure part 23, in particular inner portion 23A, and container 20, in particular portion 20B.

The securing portion 30C preferably protrudes radially towards the axis A of the cartridge 3 or container 20, is at least essentially horizontal in the normal operating position and/or extends at least essentially perpendicular to the axis A of the cartridge 3 or container 20.

Particularly preferably, the securing portion 30C engages with or reaches below a circumferential flange/edge 20D of the container 20 and/or formed by the portion 20B.

In the shown example, the flange/edge 20D is preferably formed by the preferably flange-like portion 20B of the container 20. In particular, according to the second embodiment, the portion 20B preferably protrudes radially outwards or away from the axis A of container 20 or cartridge 3, thus forming edge 20D. However, also other solutions are possible here, for example the edge 20D being formed by an indentation in container 20 or the like. In these cases, the portion 20B can also protrude inwardly like in the previous embodiment.

Particularly preferably, the closure part 23, in particular outer portion 23B, and the container 20, in particular the portion 20B, are clamped together by the securing element 30, in particular between the top portion 30A and the securing portion 30C. In this way, the closure 21 or closure part 23 is preferably axially fixed or secured by the securing element 30, mostly preferred in a sealing and/or form-fitting manner.

Particularly preferably, an axial sealing S7 is formed/established between the closure 21, in particular its outer portion 23B, and the container 20, in particular its portion 20B, mostly preferred by means of the securing element 30.

Preferably, the container 20 or its outer portion 23B comprises an axial abutment face for the closure 21, in particular the closure part 23 or its outer portion 23B. The sealing S7 is preferably formed/established by axial press/tight-fit of the closure 21 or closure part 23, in particular outer portion 23B, onto the container 20, in particular onto said abutment face, particularly preferably by means of the securing element 30.

The securing element 30 is preferably made of a material which is more rigid than the closure part 23 and/or which is less rigid than the container 20. Preferably, the securing element 30 is made of metal, particularly preferably of aluminum.

The securing element 30, in particular the top portion 30A, is preferably at least essentially ring-like and/or comprises a central opening or recess 30D.

The central recess 30D is preferably positioned and/or dimensioned such that the opening 23D of the closure 21 or closure part 23 is not covered by the securing element 30 or its top portion 30A, and/or such that the opening 23D remains accessible and/or such that the securing element 30 does not interfere with the connecting element 9 when connecting the cartridge 3 to the delivery mechanism 5.

In particular, the connecting element 9 of the nebulizer 1 can pass or reach through the securing element 30, in particular its central recess 30D.

The cartridge 3, closure 21 or securing element 30 can optionally comprise or hold the film or cover 21A.

As already mentioned, the cover 21A preferably seals the opening 23D or interior of the container 20, in particular the fluid 2, and/or forms a barrier to the surroundings. In particular, the cover 21A protects the cartridge 3, opening 23D and/or fluid 2 from contamination, for example by dust.

Preferably, the shelf-life of the cartridge 3 is increased by providing the cover 21A. In addition, the cover 21A preferably provides a tamper-proof seal or originality seal such that a user can easily see if the cartridge 3 is unopened/sealed.

The cover 21A is preferably at least essentially disc-shaped.

The cover 21A is preferably arranged between the closure 21 or closure part 23 on the one hand and the securing element 30, in particular its top portion 30A, on the other hand.

The cover 21A can be attached to the closure 21 or closure part 23 or, additionally or alternatively, to the securing element 30, in particular from below, mostly preferred by welding.

Preferably, the cover 21A is glued, heat-sealed, in particular by heat-sealing lacquer, or heat-welded to the closure 21/closure part 23 and/or securing element 30/top portion 30A.

However, it is also possible that the cover 21A is not attached/welded at all and is only held in a force-fitting and/or clamped manner between securing element 30/top portion 30A and closure 21/closure part 23.

Preferably, the cover 21A covers, closes or seals the container 20, closure 21, closure part 23 and/or opening 23D, in particular in the region of the central recess 30D, at least before the cartridge 3 is inserted into the nebulizer 1.

When the cartridge 3 is inserted or connected, the connecting element 9 preferably passes or reaches through the securing element 30, in particular its central recess 30D, and pierces or breaks the cover 21A as already described in connection with the previous embodiment.

Preferably, when the cartridge 3 is fully inserted, also the holder 6 or portions thereof reach(es) through the securing element 30 or central recess 30D.

Before assembly of the cartridge 3, the securing element 30 is preferably embodied as a flat ring. Then, when manufacturing or assembling the cartridge 3, the securing element 30, optionally with the already attached cover 21A, is preferably arranged on the closure 21 or closure part 23, in particular such that the central recess 30D is in the correct position and/or coaxially aligned with the opening 23D, and is then crimped onto the cartridge 3, thereby forming portions 30A, 30B and 30C.

Particularly preferably, the securing element 30 is embodied as a crimp cap.

As already mentioned above, according to second embodiment, the portion 20B of container 20 preferably protrudes outwards or in the direction away from the central or longitudinal axis A of cartridge 3 or container 20.

Accordingly, a circumferential indentation 23C of the closure part 23, as in the previous embodiment, can be omitted since in the present embodiment there is no corresponding inwardly protruding container portion engaging therewith. Instead, the closure 21 or closure part 23 is preferably held by press/tight-fit at an inner circumferential wall of container 20 or portion 20B and/or a (radial) sealing S1 is formed there.

Preferably, the outer diameter of the closure 21 or closure part 23 in that region is (slightly) larger than the inner diameter of the portion 20B such that the press/tight fit and/or sealing S1 is enabled or facilitated.

However, as already explained above, also for the second embodiment including the securing element 30 it is possible to form the container 20 with the portion 20B protruding inwardly.

Alternatively, it is also possible to provide a container 20 having both an outwardly protruding portion 20B and an inwardly protruding portion.

Particularly preferably, both the radial sealing S1 and the axial sealing S7 are formed/established between the closure 21, in particular closure part 23, and container 20. Preferably, in this way, a particularly liquid- and/or gas-tight connection is achieved. However, it is also possible to provide the cartridge 3 only with the radial sealing S1 or only with the axial sealing S7.

Thus, preferably at least two sealings S1, S7 are provided by the closure part 23, in particular wherein the sealings S1, S2 take effect and/or seal in different directions, namely at least essentially axially and at least essentially radially.

The closure 21, closure part 23, container 20 and/or portion 20B are/is preferably embodied at least essentially similar or identical to the corresponding components of the previous embodiment.

In the example shown, the closure part 23, in particular its inner portion 23A, preferably has at least two different outer diameters and/or is tapered. In particular, a first diameter of the closure part 23, in particular its inner portion 23A, corresponds to the inner diameter of the container 20 or its portion 20B and a second diameter of the closure part 23, in particular its inner portion 23A, is preferably smaller than the corresponding inner diameter of the container 20 in that region.

Preferably, the first outer diameter of the closure part 23, in particular its inner portion 23A, is (slightly) larger than the inner diameter of the portion 20B such that the press/tight fit and/or sealing S1 is enabled or facilitated, as already mentioned.

Optionally the cartridge 3 comprises a coding element 31. In particular, it is also possible to provide the cartridge 3 according to the previous embodiment with such a coding element 31.

The coding element 31 is preferably located at the top of the cartridge 3 and/or encompasses the closure part 23, in particular outer portion 23B, the container 20, in particular portion 20B, and/or the securing element 30, in particular the side portion 30B. Particularly preferably, the coding element 31 is clipped or snapped onto the closure 21 or securing element 30.

The coding element 31 is preferably at least essentially ring-shaped.

The coding element 31 preferably is colored or comprises a color code and/or a label (not shown). In particular, the coding element 31 is used to indicate, identify, label or mark the cartridge 3, for example by providing differently colored coding elements 31 for cartridges 3 with different ingredients or fluids 2.

Alternatively or additionally, the coding element 31 can be shaped differently for different ingredients or fluids 2. For example, the coding element 31 can comprise coding ribs 31A which protrude from the coding element 31. Likewise, the coding element 31 could also comprise coding notches (not shown).

The number and/or positions of the coding notches and/or ribs 31A are preferably different for different types of cartridges 3, in particular cartridges 3 containing different active ingredients or fluids 2, or for coding elements 31 indicating different types of cartridges 3.

Preferably, the nebulizer 1, in particular the holder 6, comprises corresponding ribs and/or notches (not shown). In particular, the ribs and/or notches of the nebulizer 1 or holder 6 are arranged such that only cartridges 3 of a certain type or with a corresponding coding element 31 can be inserted into the nebulizer 1. This preferably ensures that only cartridges 3 intended for usage with the nebulizer 1 can actually be inserted into nebulizer 1.

Figure 13:
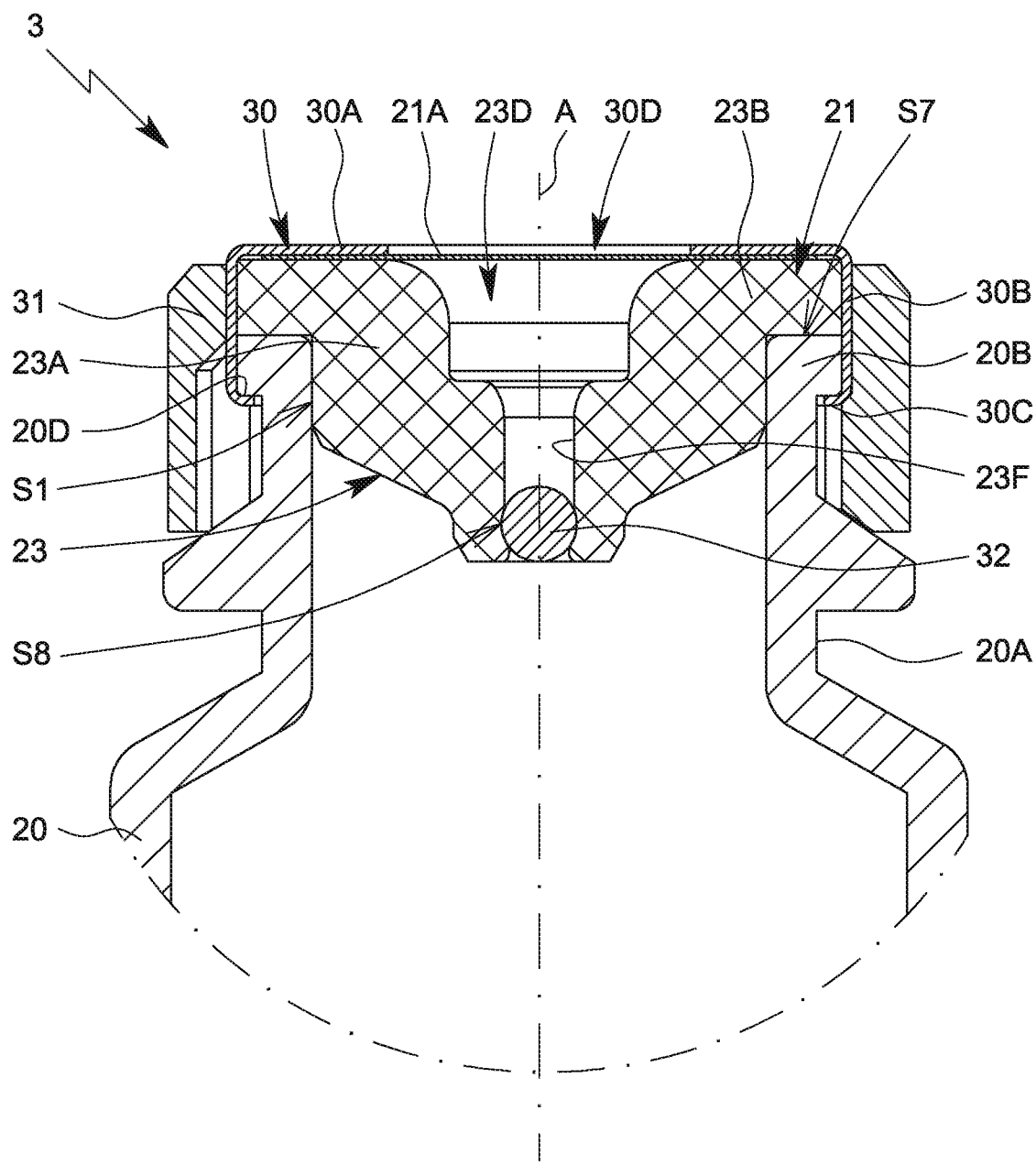
FIG. 13 is a schematic section of the cartridge in the region of the closure according to a third embodiment.

FIG. 13 shows the cartridge 3, in particular the closure 21, according to a third embodiment.

According to the third embodiment, the closure 21 preferably comprises a spherical seal 32. In particular, the closure element 24 is embodied as or replaced by the spherical seal 32 in the third embodiment.

The spherical seal 32 is preferably formed as a ball.

The spherical seal 32 is preferably made of a material which is more rigid or harder than the closure part 23, particularly preferably hard plastic.

The spherical seal 32 is preferably located within the opening 23D, particularly preferably in the second portion 23F of the closure part 23 or opening 23D, at least initially or before the cartridge 3 is inserted or connected.

The spherical seal 32 is preferably press/tight-fitted into the closure part 23, opening 23D or second portion 23F. In particular, the diameter of the spherical seal 32 is (slightly) larger than the inner diameter of the closure part 23, opening 23D or second portion 23F, in particular such that in this way, the press/tight-fit is enabled or facilitated.

In particular due to the (more) flexible closure part 23 or second portion 23F the spherical seal 32 flexes the closure part 23 or second portion 23F apart when being inserted or press/tight-fitted into the closure part 23, opening 23D or second portion 23F.

Particularly preferably, a sealing S8 is formed between the spherical seal 32 on the one hand and the closure part 23 or its second part 23F on the other hand.

In particular, the spherical seal 32 seals or closed the opening 23D, in particular in a liquid- and/or gas-tight manner.

It is also possible to reduce the inner diameter of the closure part 23, opening 23D or second portion 23F in the region of the spherical seal 32 to facilitate the press/tight-fit and/or forming of sealing S8.

The connecting element 9 is preferably adapted to push the spherical seal 32, mostly preferred out of the closure 21 or closure part 23 and/or into the container 20.

In particular, the connecting element 9 is made of a rigid material, preferably metal. Preferably, the connecting element 9 is also adapted to pierce or break the optional cover 21A.

Figure 16:
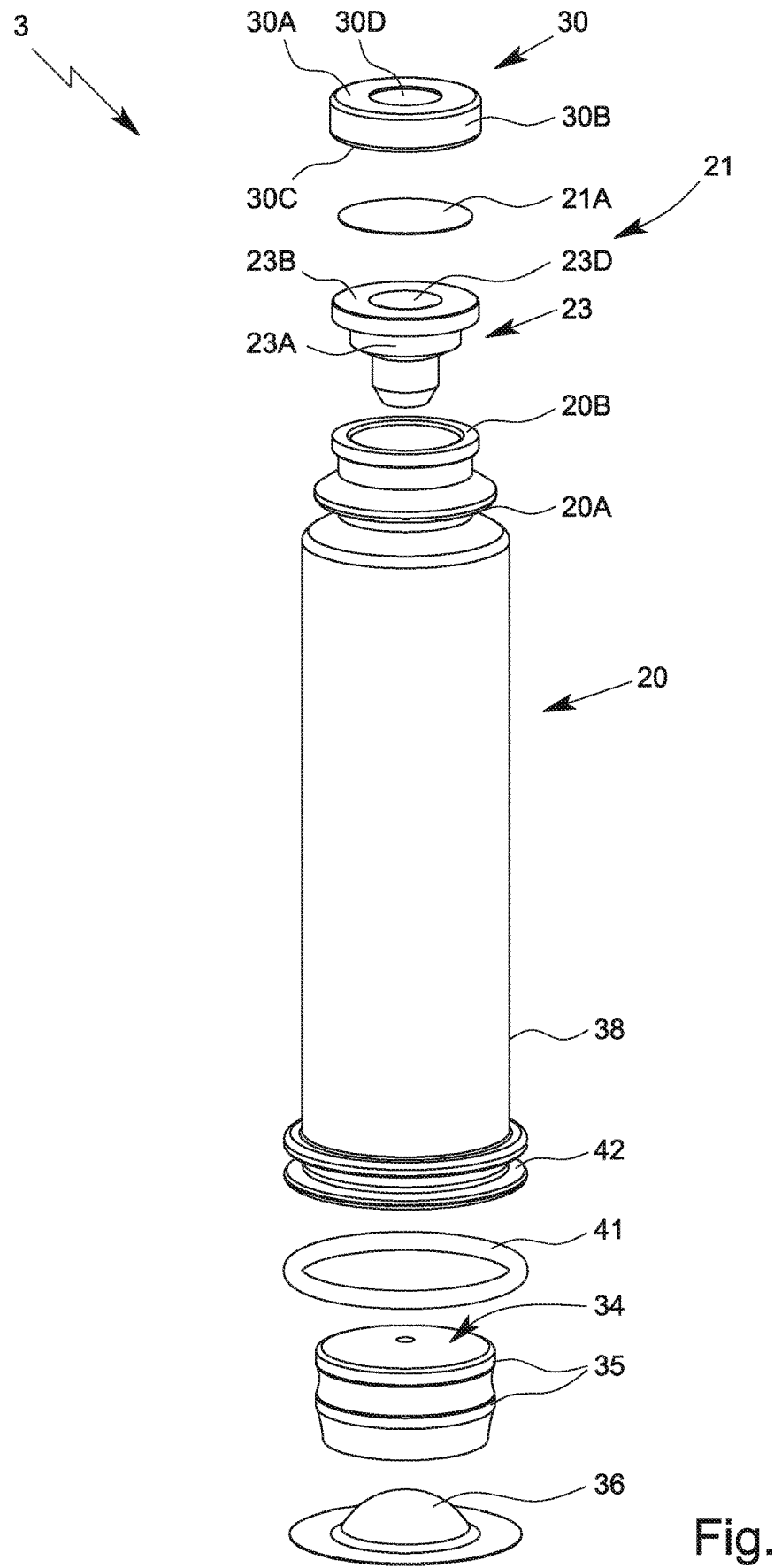
FIG. 16 is a schematic exploded view of the cartridge according to FIG. 14.

When the cartridge 3 is inserted into the nebulizer 1, the connecting element 9 preferably pushes the spherical seal 32 out of the closure 21, closure part 23 or opening 23D, and/or breaks the sealing S8. Preferably, a sealing S5 between the connecting element 9 and the closure part 23 is formed, in particular at the same location of the previous sealing S8. In other words, the sealing S8 between the spherical seal 32 and the closure part 23 is preferably replaced by the sealing S5 between the connecting element 9 and the closure part 23.

The spherical seal 32 is preferably pushed into the interior of the cartridge 3 or container 20.

Since the cartridge 3 or closure 21 according to the third embodiment preferably does not comprise the closure element 24 for displacing a displacement volume, a respective chamber 23M for a displacement portion 24B can be omitted. Thus, it is not necessary to embody the closure part 23 with a third portion 23G. In particular, the closure 21 or closure part 23, particularly its inner portion 23A or opening 23D, can be shorter than in the previous embodiments.

FIGS. 14 to 16 show the cartridge 3 according to a fourth embodiment. FIG. 14 shows the entire cartridge 3 in a schematic section. FIG. 15 shows a detail of the cartridge 3 according to FIG. 14 in the region of the closure 21. FIG. 15A is a perspective view of the closure 21. FIG. 15B shows a detail of the cartridge 3 corresponding to FIG. 15 when connected to the nebulizer 1. FIG. 16 is an exploded perspective view of the cartridge 3 according to FIG. 14 or the fourth embodiment.

According to the fourth embodiment, the closure 21, in particular the closure part 23, comprises a membrane or sealing wall 33.

Preferably, the sealing wall 33 is located within the opening 23D of the closure part 23 and/or seals or closes the cartridge 3, closure 21, closure part 23 and/or opening 23D, in particular in a liquid- and/or gas-tight manner.

The membrane or sealing wall 33 is preferably at least essentially disc-shaped. Preferably, the sealing wall 33 extends in the radial direction and/or at least essentially horizontally in the normal operating position.

Preferably, the sealing wall 33 is connected with the closure part 23 along its circumference.

Particularly preferably, the sealing wall 33 is integrally formed or formed as one piece with the closure part 23. In particular, the sealing wall 33 is made of the same, preferably flexible, material as the closure part 23, particularly preferably butyl rubber.

The sealing wall 33 is preferably pierceable or breakable, in particular by the connecting element 9.

Thus, the connecting element 9 is preferably adapted to pierce or break the sealing wall 33.

Figure 15:
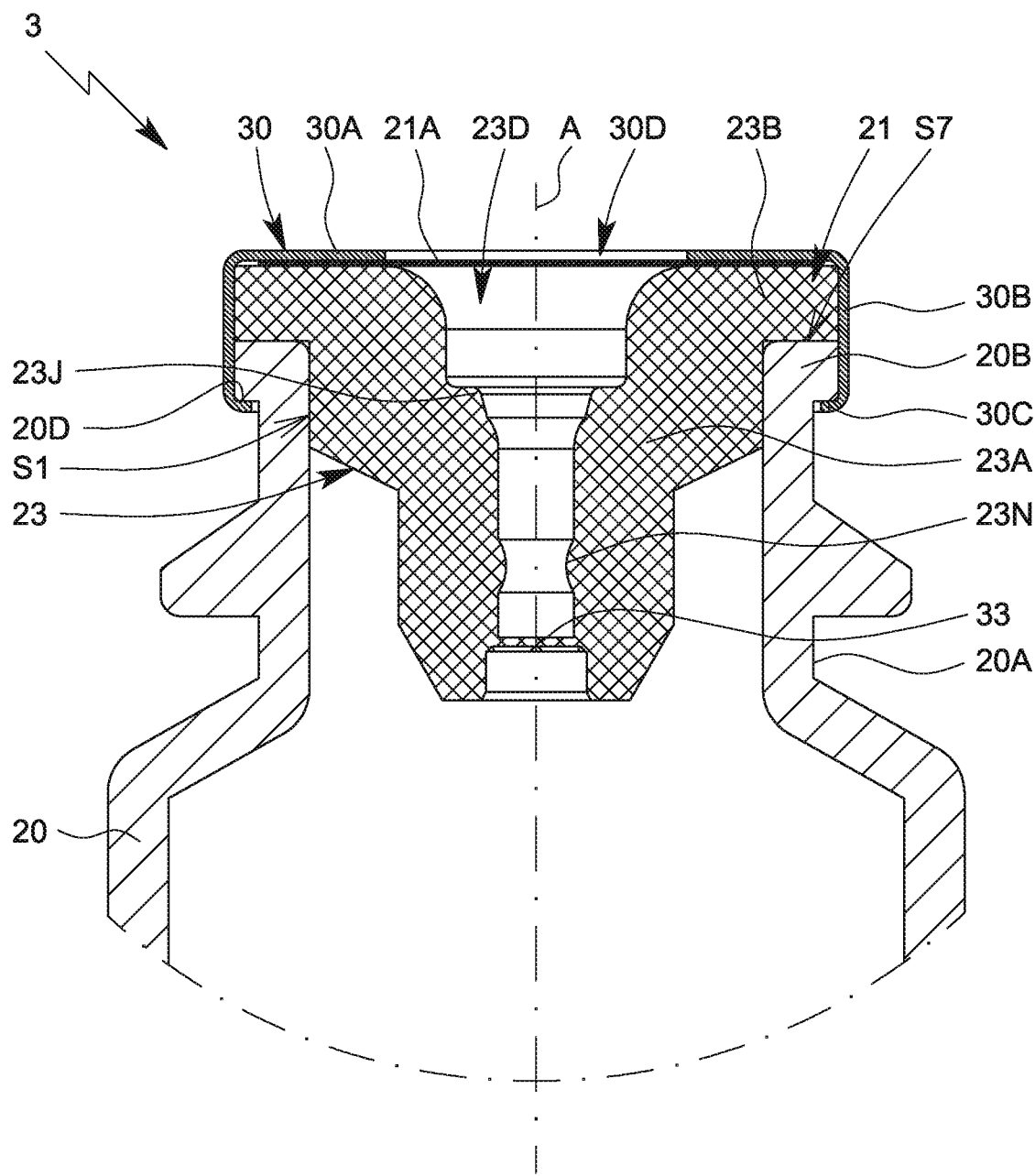
FIG. 15 is a schematic section of the cartridge according to FIG. 14 in the region of the closure.
Figure 15A:
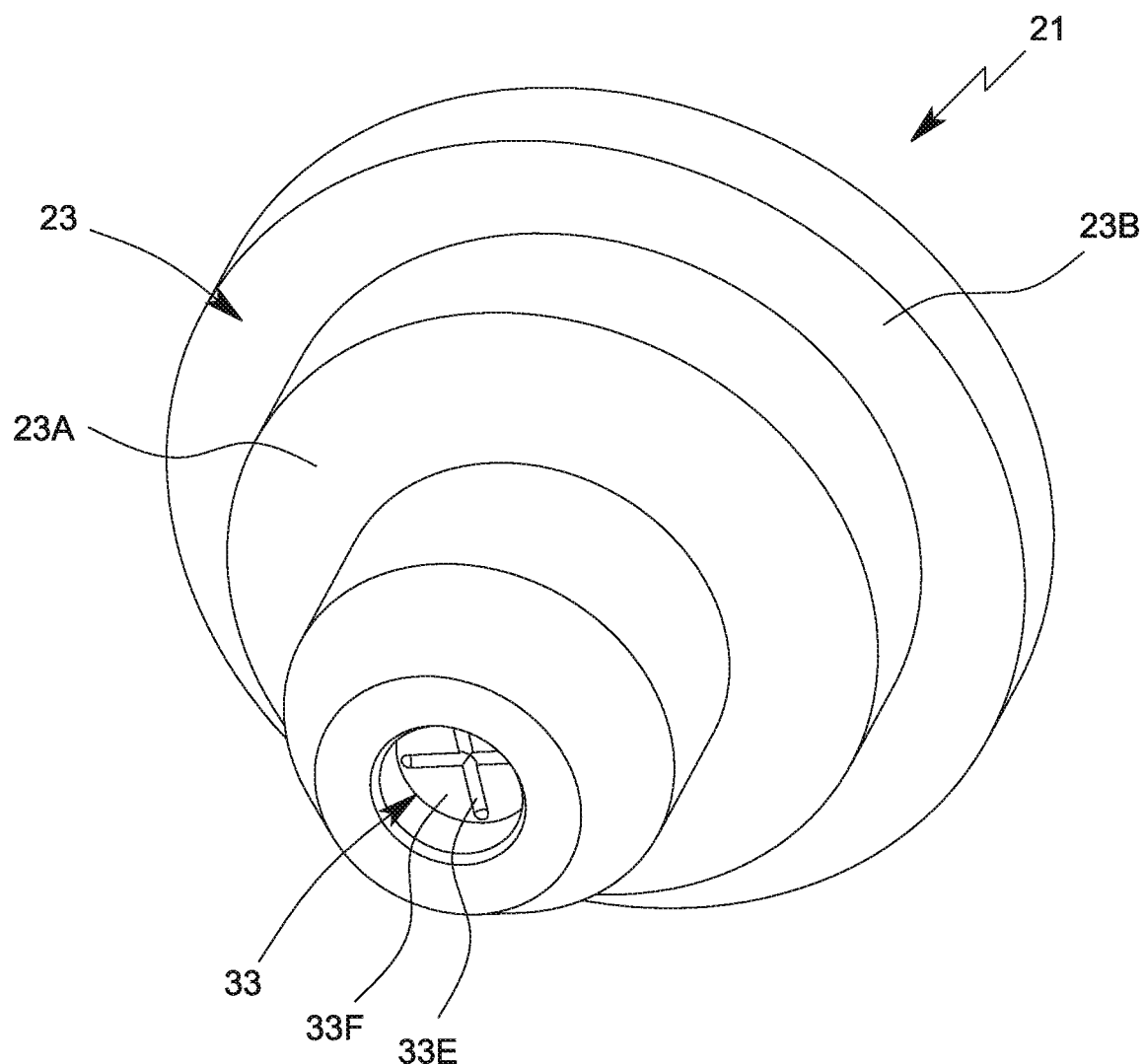
FIG. 15A is a perspective view of the closure according to FIG. 15.

Preferably, the sealing wall 33 comprises at least one recessed portion 33E of reduced thickness, as shown in FIG. 15A.

The recessed portion 33E preferably forms a predetermined breaking point of the sealing wall 33, in particular when being pierced/broken by the connecting element 9.

Preferably, the thickness of the recessed portion 33E is less than 0.1 mm or 0.05 mm.

The recessed portion 33E preferably partitions the sealing wall 33 into a plurality of flexing portions 33F. Preferably, the flexing portions 33F have at least essentially the same shape and/or size.

Particularly preferably, the recessed portion 33E is at least essentially cross-like or formed as a cross, as shown in FIG. 15A. In particular, the recessed portion 33E partitions the sealing wall 33 into four flexing portions 33F. In this case, the flexing portions 33F are preferably at least essentially shaped as four preferably at least essentially similarly shaped/sized circular sectors.

However, also other solutions are possible here, for example a recessed portion 33E partitioning the sealing wall 33 into just two, in particular half-disk shaped, flexing portions 33F.

An at least essentially star-shaped recessed portion 33E is possible as well, which partitions the sealing wall 33 into three preferably at least essentially similarly shaped/sized circular sectors.

Preferably, the flexing portions 33F are connected with each other via the recessed portion 33F in the initial/delivery state. In particular, the sealing wall 33 is integrally formed or formed as one piece.

When the connecting element 9 is pushed against the sealing wall 33, the sealing wall 33 preferably tears/breaks along the recessed portion 33E.

The flexing portions 33F preferably flex apart when the connecting element 9 is further pushed into the cartridge 3 such that the connecting element 9 can pass the flexing portions 33F.

Preferably, the flexing portions 33F of the sealing wall 33 remain connected to the closure 21, in particular closure part 23, also after the sealing wall 33 has been teared/broken, i.e. after the connecting element 9 has been (completely) inserted.

Particularly preferably, a defined breaking of the sealing wall 33, in particular tearing along the recessed portion 33E and/or flexing apart of the flexing portions 33F, is made possible, in particular without the sealing wall 33 or flexing portions 33F being completely separated from the closure 21 or closure part 23. In particular, it is prevented that the flexing portions 33F fall off into the fluid 2.

Figure 15B:
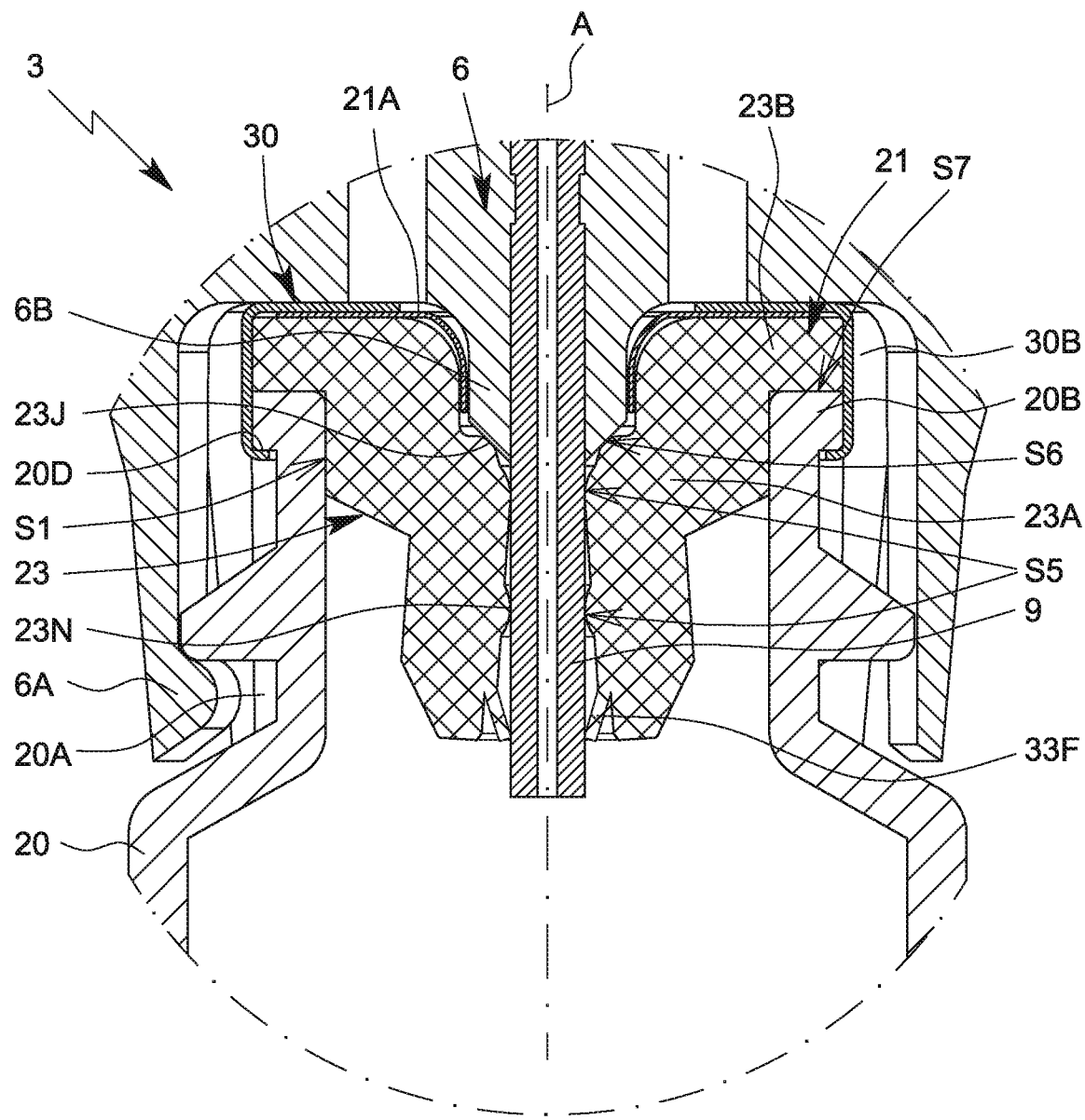
FIG. 15B is a schematic section of the cartridge according to FIG. 15 connected to the nebulizer.

FIG. 15B shows in a schematic section according to FIG. 15 the cartridge 3 when being connected, where the sealing wall 33 is broken and the flexing portions 33F are flexed apart.

Preferably, the closure 21, in particular closure part 23 or opening 23D, comprises a sealing portion 23N. The sealing portion 23N is preferably integrally formed with the closure part 23.

Particularly preferably, the sealing portion 23N is embodied as a circumferential bulge within the opening 23D or as a portion of the opening 23D with reduced diameter. In particular, the inner diameter of the sealing portion 23N is smaller than the outer diameter of the connecting element 9.

When the connecting element 9 is received by the closure 21, in particular in the opening 23D of closure part 23, the flexible/deformable/stretchable closure part 23 is preferably flexed/stretched apart by the connecting element 9, in particular in the region of the sealing portion 23N.

Preferably, in the region of the sealing portion 23N, a particularly tight sealing S5 is formed/established. Preferably, also further sealings S5 between the connecting element 9 and the closure 21, in particular closure part 23, are formed/established at other regions, as shown in FIG. 15B. Preferably, one or more further sealing(s) S5 is/are formed/established between the connecting element 9 and the flexing portions 33F.

Further, also one or more sealings S6 between the holder 6 and the closure 21, in particular closure part 23, can be formed/established, as already described in connection with the first embodiment.

In the shown example, the closure 21 does not comprise a closure element 24 or spherical seal 32. However, it is also possible to include the closure element 24 or the spherical seal 32 in the fourth embodiment and/or to include the sealing wall 33 in any of the previous embodiments. In these cases, the sealing wall 33 preferably provides an additional seal. Preferably, the sealing wall 33 is located above the closure element 24 or spherical seal 32 or closer to the top, in particular such that the connecting element 9 first needs to pierce or break the sealing wall 33 before it can push the closure element 24 or spherical seal 32.

As already mentioned, the cartridge 3 preferably comprises a variable volume 4. In the fourth embodiment shown in FIGS. 14 to 18, the cartridge 3 is equipped with a movable element or piston, hereinafter referred to as fluid piston 34.

Preferably, the fluid piston 34 is axially movable within the container 20, in particular in order to reduce the volume 4. In this sense, also the cartridge 3 of the fourth embodiment preferably comprises a variable volume 4.

Figure 14:
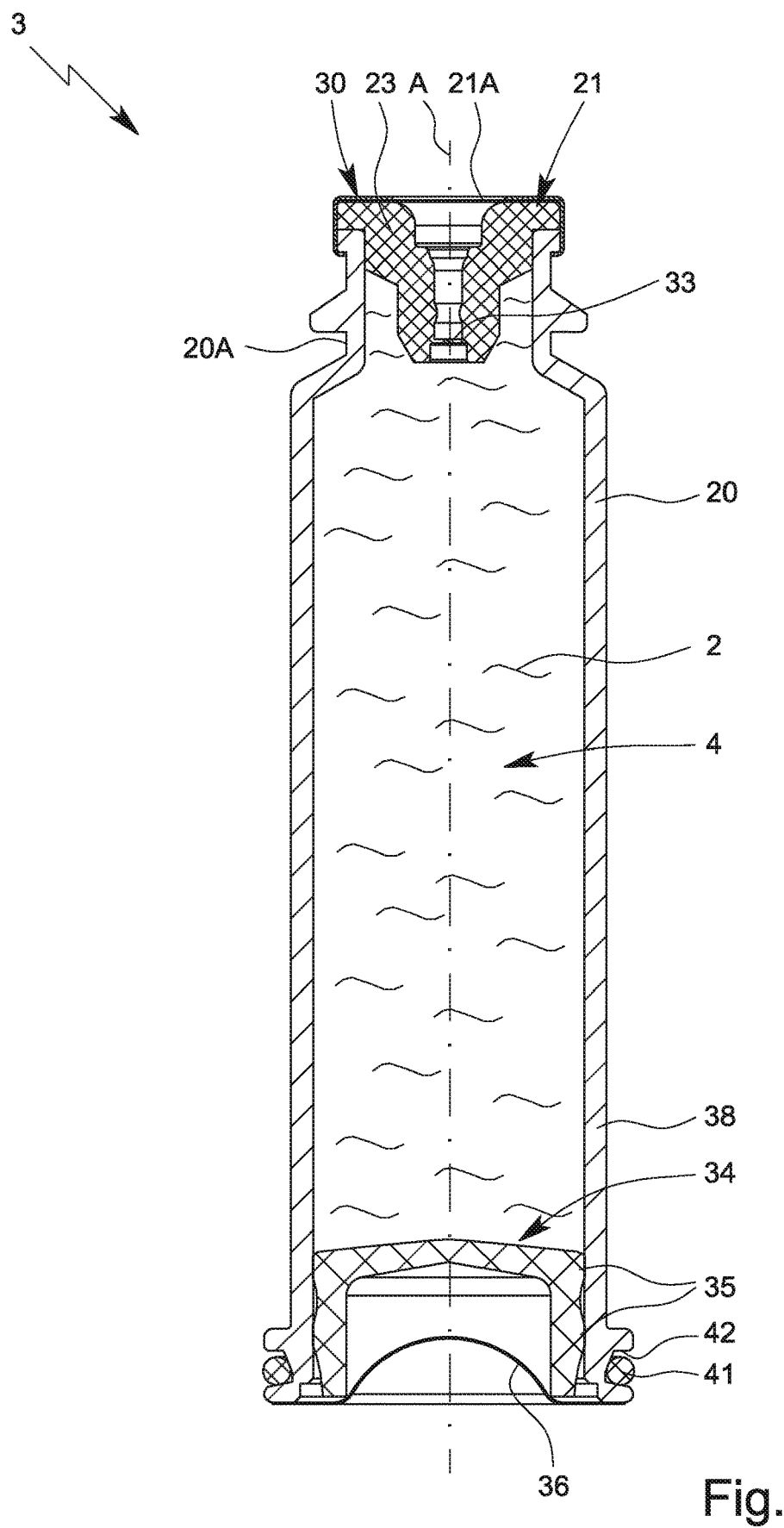
FIG. 14 is a schematic section of the cartridge according to a fourth embodiment.

FIG. 14 shows the cartridge 3 in the delivery and/or a completely filled state, the fluid piston 34 being in its initial position before withdrawing any fluid 2 from the container 20.

In the initial position and/or delivery state, the volume 4 of the cartridge 3 is maximized and/or the fluid piston 34 is arranged at a base or axial end of the cartridge 3 and/or opposite to the closure 21.

When withdrawing the fluid 2 out of the cartridge 3, the fluid piston 34 moves axially towards the outlet or closure 21, here upwards, thereby reducing the volume 4 of the cartridge 3.

Preferably, the cartridge 3 is provided with a piston seal 35 acting between the fluid piston 34 and the container/casing 20. In the present embodiment, the fluid piston 34 and the piston seal 35 are formed integrally. With other words, the fluid piston 34 preferably comprises or forms the piston seal 35. However, other constructional solutions are possible as well, in particular wherein the piston seal 35 is formed as a sealing ring or a sealing lip and/or held by the fluid piston 34.

Optionally, the cartridge 3 might be provided with an (axial) base seal 36, preferably wherein the base seal 36 covers or seals the cartridge 3, in particular its axial end or base. Mostly preferred, the base seal 36 covers or seals the gap between the fluid piston 34 and the container/casing 20.

The base seal 36 preferably serves as a barrier against contamination, e.g. dust, and/or can be used as a quality seal and/or label and/or might comprise notes or user instructions.

In the present embodiment, the base seal 36 is preferably curved, in particular concavely on a side facing away from the closure 21 and/or convexly on a side facing the closure 21. Mostly preferred, the base seal 36 is at least essentially dome-like shaped. However, other constructional solutions are possible as well, in particular wherein the base seal 36 is ring-like.

Preferably, the base seal 36 is attached, in particular bonded, to the bottom/axial end of the cartridge 3. In the current embodiment, the base seal 36 is preferably attached, in particular bonded, to the container 20, in particular a bottom thereof. Preferably, the base seal 36 is not attached/bonded to the fluid piston 34 such that the fluid piston 34 is freely movable.

The base seal 36 is preferably opened/pierced/cut open when using/tensioning the nebulizer 1 for the first time, as will be explained in the following with reference to FIGS. 17 and 18.

FIGS. 17 and 18 show the nebulizer 1 in a schematic section similar to FIG. 1 with inserted/connected cartridge 3 according to the fourth embodiment. FIG. 17 shows the nebulizer 1 in the non-tensioned/initial state and FIG. 18 shows the nebulizer 1 in the tensioned state.

In FIGS. 17 and 18 the cartridge 3 has been fluidically connected to the delivery mechanism 5 of the nebulizer 1. In particular, the cover 21A and the sealing wall 33 have been pierced/broken/opened by the connecting element 9. Further, the respective sealings between the closure 21 or closure part 23 on the one hand and the connecting element 9 and holder 6 on the other hand have been established. The connecting element 9 and a portion of the holder 6 are passing or reaching through the securing element 30, in particular its central recess 30D, as already described.

In particular in order to help to move the fluid piston 34 (or to collapse a bag contained in the cartridge 3) during withdrawal of a dose of the fluid 2 and/or tensioning of the nebulizer 1, the nebulizer 1 might be equipped with an optional air pump 37.

The air pump 37 preferably comprises a pump piston 38 and a cylinder 39 cooperating with the pump piston 38. Thus, the air pump 37 comprises or forms a piston/cylinder arrangement for pressurizing the fluid 2 in the cartridge 3 and/or for increasing the air pressure in a pump chamber 40 formed by the pump piston 38 and the cylinder 39, in particular during withdrawal of a dose of the fluid 2 and/or tensioning of the nebulizer 1.

The cylinder 39 is preferably formed by the axial end and/or housing part 18 of the nebulizer 1. However, other constructional solutions are possible as well, in particular wherein the cylinder 39 is formed by an element or insert attached to or arranged in the nebulizer 1, in particular its housing part 18.

Preferably, the cartridge 3, in particular the container 20, mostly preferred its axial end, forms or is used as the pump piston 38.

The cartridge 3, in particular the container 20, preferably cooperates with the cylinder 39 preferably formed by the housing part 18, in particular so that a piston/cylinder arrangement for pressurizing the fluid 2 in the cartridge 3 is formed.

The air pump 37 preferably comprises a pump chamber 40, preferably wherein the pump chamber 40 is formed by the pump piston 38 and the cylinder 39. In particular, the volume of the pump chamber 40 is defined or varied by the position or movement of the pump piston 38 within the cylinder 39.

Mostly preferred, the pump chamber 40 is radially limited by means of the cylinder 39 and/or axially limited by means of the pump piston 38 and/or fluid piston 34.

Preferably, the air pump 37 acts directly on the fluid piston 34 in order to pressurize the fluid 2 in the volume 4 of the cartridge 3.

Preferably, the cartridge 3 comprises an air seal 41 acting between the pump piston 38 and the cylinder 39 and/or arranged between the pump piston 38 and the cylinder 39, in particular such that the gap between the pump piston 38 and the cylinder 39 is sealed.

Preferably, the air seal 41 is embodied as a seal ring, i.e. O-ring. However, other constructional solutions are possible as well, in particular wherein the air seal 41 is embodied as a sealing lip.

Preferably, the air seal 41 extends around the pump piston 38, in particular in a circumferential grove 42 thereof.

Preferably, the nebulizer 1 or air pump 37 comprises at least one air valve 43 for controlling or limiting the (maximum) air pressure and/or for aerating the air pump 37 or its pump chamber 40 and/or for preventing any underpressure (negative pressure with respect to the ambient pressure) in the air pump 37 or pump chamber 40. However, the air valve 43 is only optional and can be omitted.

In the present embodiment, the air valve 43 is preferably dome-like shaped, curved and/or at least essentially hemispherical.

Preferably, the air valve 43 opens preferably very easily (i.e. at a very low-pressure difference between the ambient pressure and the pressure in the pump chamber 40) towards the interior of the air pump 37 or pump chamber 40 in order to allow ambient air to flow into the pump chamber 40 in order to prevent any underpressure in the pump chamber 40. With other words, the air valve 43 preferably forms an inlet valve.

Further, the air valve 43 can flex or open to the outside, i.e. away from the interior of the air pump 37, and allows air to escape from the pump chamber 40, mostly preferred only if the pressure inside the pump chamber 40 is significantly higher than the ambient air pressure, i.e. only if the pressure difference reaches or exceeds a maximum value corresponding to a maximum air pressure. With other words, the air valve 43 preferably also forms a control valve.

Optionally, the nebulizer 1, housing part 18, air pump 37 or air valve 43 comprises a (sterile) filter 44 such that impurities or foreign substances of the air are prevented from entering the pump chamber 40. The filter 44 is in particular arranged within or upstream (with regard to air flowing into the pump chamber 40) of air valve 43. Preferably, the filter 44 is embodied as a filter membrane, a perforated plate or a combination thereof.

Figure 17:
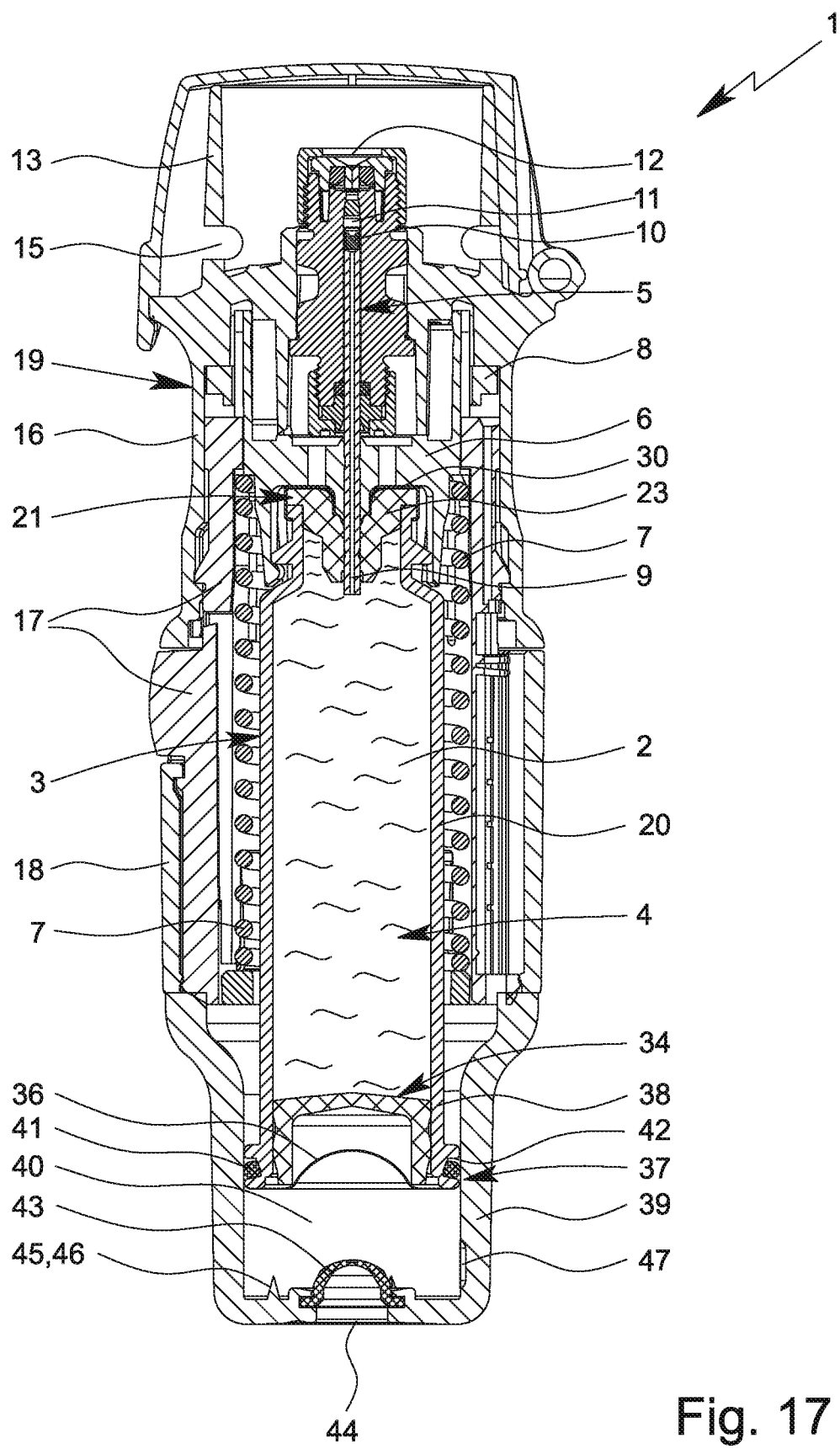
FIG. 17 is a schematic section of the nebulizer in the non-tensioned state with the cartridge according to FIG. 14.
Figure 18:
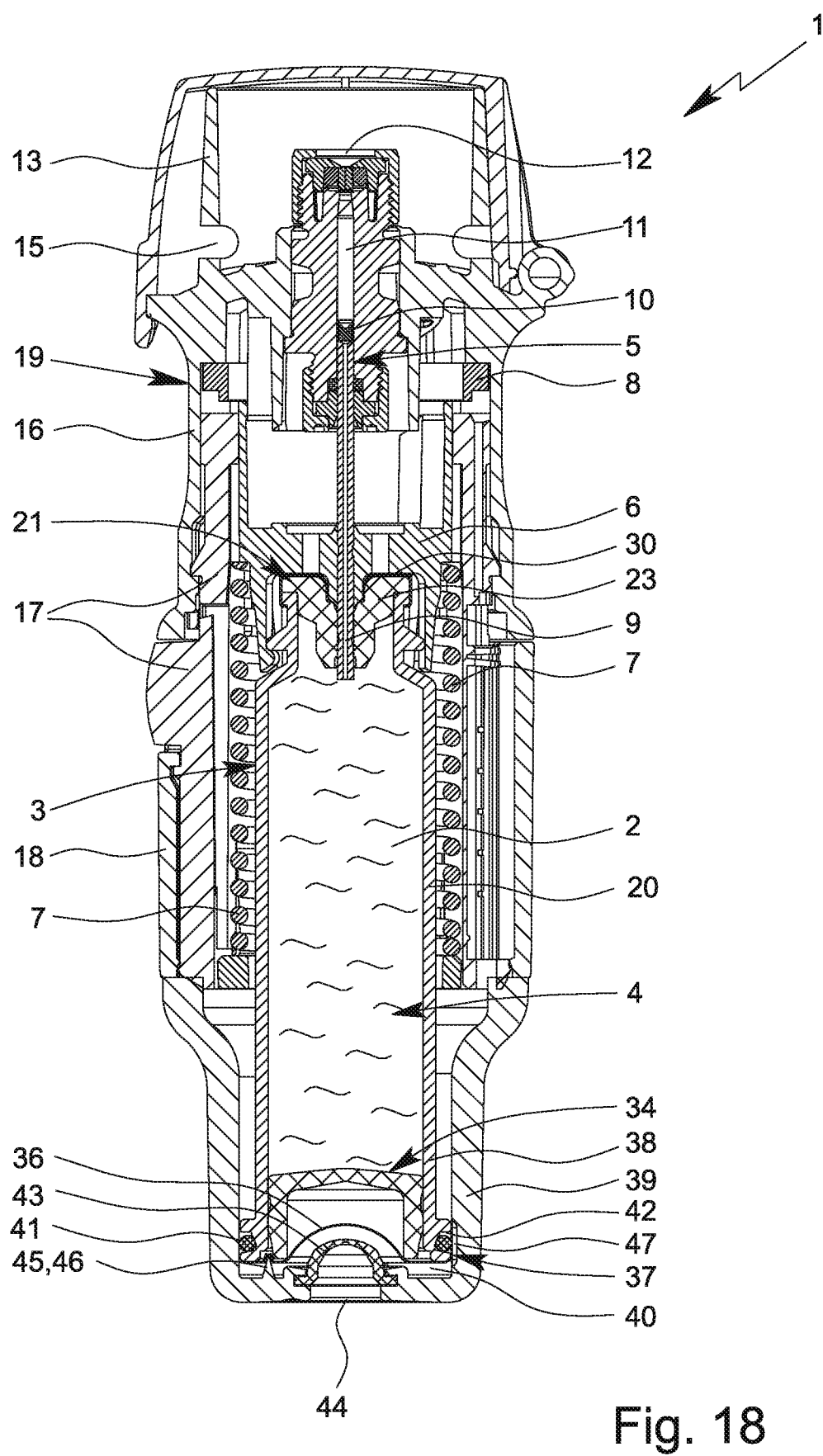
FIG. 18 is a schematic section of the nebulizer according to FIG. 17 in the tensioned state.

FIG. 17 shows the nebulizer 1 in the delivery/unused/initial state. FIG. 18 shows the nebulizer 1 when being used/tensioned for the first time, i.e. when the base seal 36 attached to the axial end of the cartridge 3 is open.

The delivery/unused/initial state of the nebulizer 1/cartridge 3 is preferably the state in which the nebulizer 1/cartridge 3 is delivered from the factory. Mostly preferred, the nebulizer 1 is not tensioned in the delivery/unused state of the nebulizer 1 and/or the cartridge 3, in particular the base seal 36 is intact/unopened/unpierced in the delivery/unused state of the cartridge 3.

The nebulizer 1 preferably comprises an opening device 45 for opening the base seal 36, preferably when using/tensioning the nebulizer 1 for the first time.

In particular, the opening device 45 is adapted to pierce/cut open the base seal 36, preferably between the pump piston 38 and the cylinder 39 and/or in a circular/annular manner and/or such that air can flow through the base seal 36.

Preferably, the opening device 45 comprises at least one opening element 46, preferably wherein the opening element 46 comprises a sharp/tapered end/tip in order to open, pierce or cut open the base seal 36. Mostly preferred, the opening element 46 is embodied as a spike or set of spikes. However, other constructional solutions are possible as well.

Preferably, the opening device 45, in particular the opening element 46, is formed by or integrally with the housing part 18 or cylinder 39.

When the nebulizer 1 is tensioned and/or the cartridge 3 moves downwards and/or towards the air valve 43, the volume of the pump chamber 40 is reduced and the pressure therein is increased. In this way, a force is exerted on the fluid piston 34 which helps or supports to move the fluid piston 34 axially and/or to decrease the volume 4. In this way, any underpressure in the volume 4 can be avoided during the withdrawal of a dose of the fluid 2 from the container 20.

With other words, a pressure impulse acts on the volume 4 or fluid 2 at the beginning of and/or during the tensioning of the nebulizer 1 and/or withdrawal of fluid 2 from the cartridge 3. This helps withdrawing the fluid 2 in doses from the cartridge 3 without forming any gas bubbles within the cartridge 3.

Particularly preferably, fluid 2 is pressed/displaced into the delivery mechanism 5 by means of the fluid piston 34, thus filling the pressure chamber 11. In particular, by means of the air pump 37, it is ensured that the displacement of fluid 2 into the delivery mechanism 5 remains at least essentially constant for each actuation/use of the nebulizer 1 such that the preferred dose of fluid 2 is dispensed.

Optionally, the nebulizer 1, in particular the air pump 37, comprises an (over-) pressure means/depressurization means/pressure relief means 47, hereinafter referred to as pressure relief means 47, preferably wherein the pressure relief means 47 is adapted to control and/or limit the air pressure within the air pump 37 or its pump chamber 40, preferably independently of the velocity of tensioning/cocking/loading of the nebulizer 1, i.e. independently of the speed with which the housing part 18 is rotated relative to the upper housing part 16.

Mostly preferred, the pressure relief means 47 is adapted to decrease the pressure in the air pump 37 or its pump chamber 40, preferably dependent on the (axial) position of the cartridge 3 within the nebulizer 1 or housing part 18.

Preferably, the pressure relief means 47 is embodied as a bypass or a bypass channel which is integrated into the pump piston 38 or cylinder 39.

Mostly preferred, the pressure relief means 47 is formed by a longitudinal/axial groove within the cylinder 39 and/or housing part 18.

The pressure relief means 47 is preferably activated or activatable and/or opened or openable when a predefined (axial) position of the pump piston 38 within/relative to the cylinder 39 is reached, in particular when the pump piston 38 reaches its lower axial (end) position and/or (only) during tensioning the nebulizer 1, in particular at the end of the tensioning process as shown in FIG. 18.

Mostly preferred, the pressure relief means 47 is adapted to bypass the air seal 41 and/or pneumatically connect the air pump 37 or its pump chamber 40 to the atmosphere/environment, in particular such that a (remaining) overpressure—compared to the ambient pressure—in the nebulizer 1 or air pump 37, in particular its pump chamber 40, can be compensated.

In this way, the air pressure is (abruptly) reduced to ambient pressure, when a predefined axial position of the pump piston 38 within the cylinder 39 is reached and/or when the tensioning process ends.

Thus, due to the air pump 37 and the pressure relief means 47 only a very short pressure impulse is generated in order to support moving the fluid piston 34 during withdrawal of a dose of the fluid 2 and/or tensioning of the nebulizer 1.

In particular due to the short pressure impulse, the fluid piston 34 is only temporarily and/or during the tensioning process pushed against the fluid 2 within the container 20 such that fluid 2 is displaced into the delivery mechanism 5.

With other words, the pressure relief means 47 ensures that the pump chamber 40 is pressureless/unpressurized after the tensioning process is completed. This prevents a leakage out of the nebulizer 1, in particular its nozzle 12.

Figure 19:
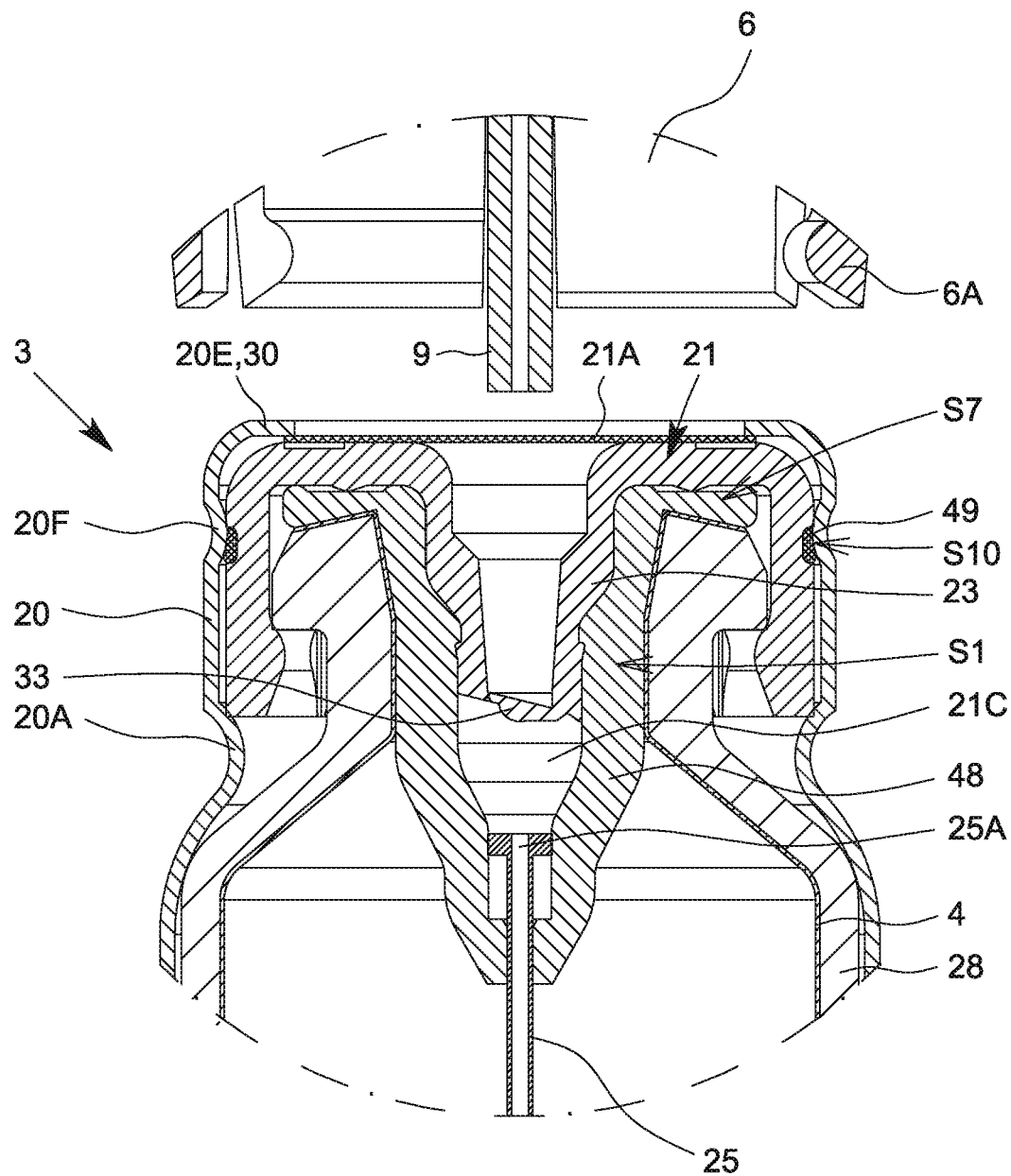
FIG. 19 is a schematic section of the cartridge with a closed sealing wall according to a fifth embodiment.
Figure 20:
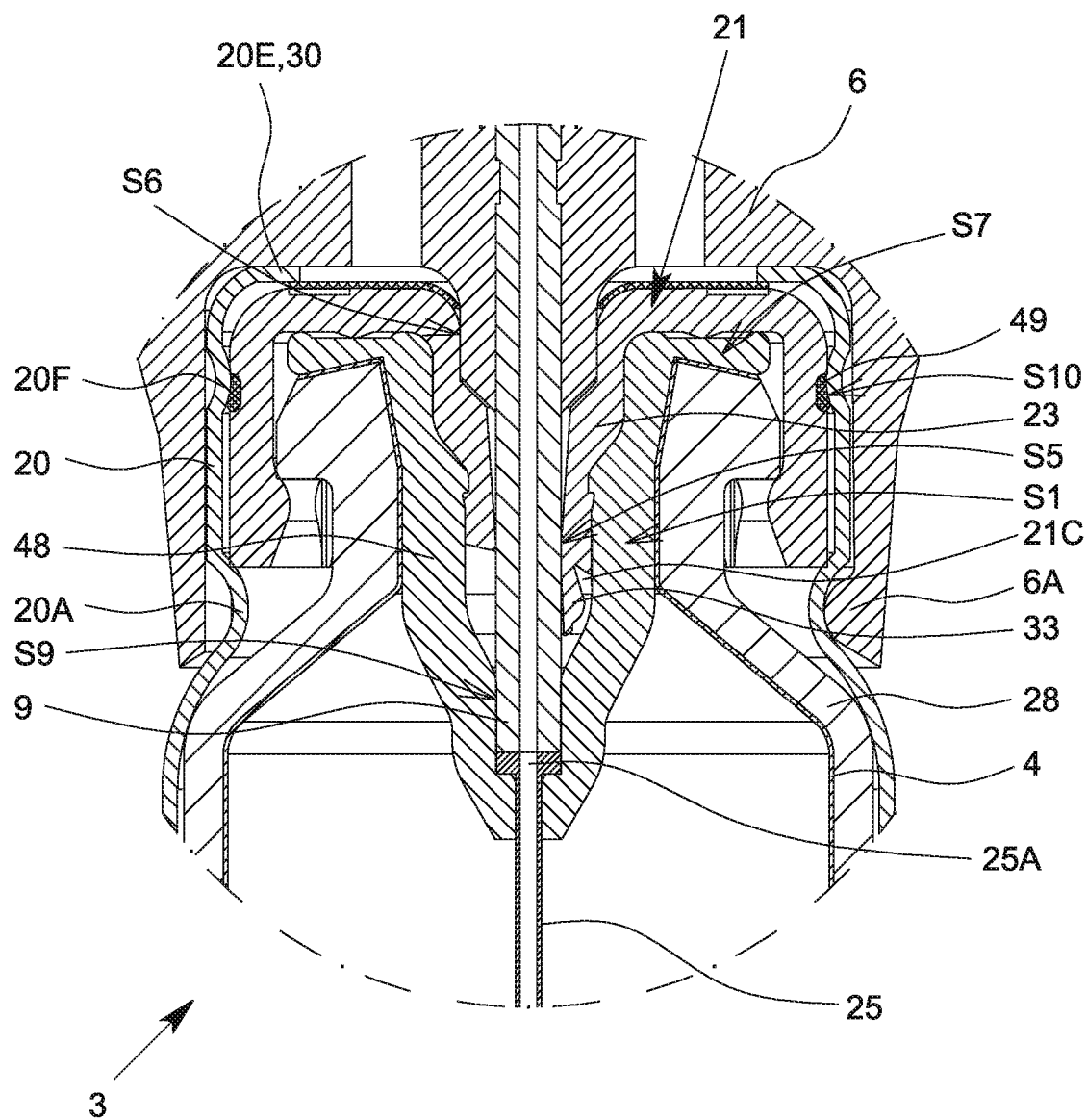
FIG. 20 is a schematic section of the cartridge according to the fifth embodiment with an opened sealing wall, connected to a partially shown nebulizer.
Figure 21:
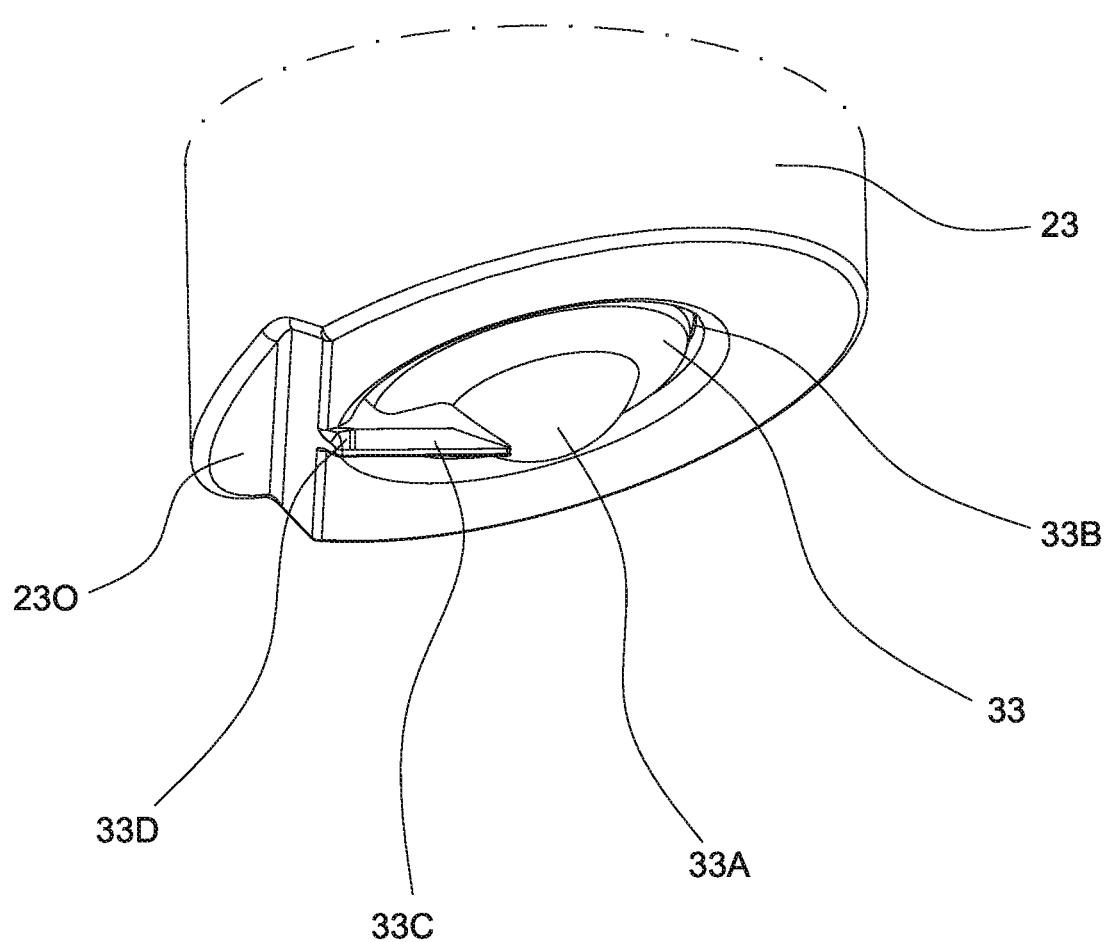
FIG. 21 is a perspective detail of the cartridge according to the fifth embodiment.

FIGS. 19 to 21 show the cartridge 3 according to a fifth embodiment of the present invention. FIG. 19 shows the cartridge 3 before being connected to the delivery mechanism 5 and/or with closed or intact cover 21A and/or membrane or sealing wall 33. FIG. 20 shows the cartridge 3 when connected to the delivery mechanism 5 and/or with opened or pierced cover 21A and/or membrane or sealing wall 33. FIG. 21 is a schematic detail of the membrane or sealing wall 33 in the closed or intact state.

According to the fifth embodiment, the cartridge 3 or closure 21 can optionally comprise an adapter/sealing element 48 in particular for connecting the tube 25 to the closure 21 or closure part 23.

Preferably, the closure part 23 and adapter 48 are connected with each other by press/tight-fit. However, also other solutions are possible here, for example the closure part 23 and adapter 48 being formed integrally or as one piece.

Preferably, the fixed end 25A of the tube 25 is axially moveable relative to and/or within the closure 21 and/or adapter 48. The fixed end 25A is preferably only fixed with respect to radial movement, at least initially or in the delivery state.

The delivery state is to be understood as the state before the cartridge 3 is connected to or inserted into the nebulizer 1.

After the cartridge 3 has been connected to the delivery mechanism 5 of the nebulizer 1, the fixed end 25A is preferably also fixed with respect to axial movement.

The fixed end 25A and/or tube 25 is preferably adapted to compensate length tolerances of connecting element 9.

In the delivery state or before the cartridge 3 is connected to the delivery mechanism 5 of the nebulizer 1, fixed end 25A and/or tube 25 is preferably arranged in the adapter 48 in an initial position which allows to push the fixed end 25A and/or tube 25 further downwards in the axial direction.

Preferably, the fixed end 25A and/or tube 25 is held in said initial position by (radial) force-fit.

When the connecting element 9 is inserted and/or when the cartridge 3 is connected to the delivery mechanism 5 of the nebulizer 1, the connecting element 9 pushes or moves the fixed end 25A and/or tube 25 (further) down in the axial direction (i.e. towards the inside of the cartridge 3), depending on the axial length of the connecting element 9.

In this way, it is preferably possible to compensate for length variations of the connecting element 9.

FIG. 20 shows the case where the tube 25 has been pushed or moved maximally. However, also cases are possible where the tube 25 is pushed/moved downwards only partly or not at all, in particular when the connecting element 9 is shorter as in the example shown in FIG. 20.

However, the tube 25 in the fifth embodiment is preferably only optional. Hence, the following explanations, features and advantages described in connection with the fifth embodiment can preferably also be implemented independently from the tube 25.

According to the fifth embodiment, the cartridge 3 preferably comprises the intermediate container 28 and/or the variable/collapsible volume 4 in the form of a flexible/collapsible bag.

Preferably, the radial sealing S1 and/or the axial sealing S7 between the closure 21 and the container 20 or, as in the depicted example, between the closure 21 and/or closure part 23 on the one hand and the intermediate container 28 and/or bag on the other hand, is realized by the adapter 48. In this case, the adapter 48 is preferably embodied as a sealing element. In particular, in the case without tube 25, the adapter 48 is only provided as sealing element for the cartridge 3.

The adapter/sealing element 48 preferably extends axially into container 20 or 28 and can optionally also protrude radially over the edge of an opening of the container 20 or 28. In particular, the adapter/sealing element 48 is held or fixed between closure 21, in particular closure part 23, and container 20 or 28 by radial and/or axial press/tight-fit. Particularly preferably, a gas- and/or liquid-tight connection or sealing is formed between the adapter/sealing element 48 and the container 20 or 28, in particular radially and/or axially.

Preferably, the adapter/sealing element 48 is funnel- and/or cone-shaped and/or attached to the closure part 23. In particular, the adapter/sealing element 48 is flexible and/or adapted to sealingly receive the closure part 23 and/or connecting element 9, in particular its axial end, mostly preferred in a press/tight-fit manner.

Preferably, the closure 21 comprises the adapter/sealing element 48.

The adapter/sealing element 48 is preferably made of rubber, in particular nitrile rubber, butadiene rubber, styrene-butadiene rubber, isoprene rubber, styrene-isoprene rubber, butyl rubber, ethylene propylene diene monomer rubber, or the like, and/or (flexible) plastic, in particular thermoplastics and/or thermoplastic elastomers, such as polyamide, polyethylene, polypropylene, polyurethane, polybutylene terephthalate or polyether block amide or the like. Other suitable materials might be used as well.

Preferably, the connecting element 9—once inserted—and the adapter/sealing element 48 are connected sealingly and/or in a press-fitting manner. In particular, the (flexible) adapter/sealing element 48 is (laterally) expanded by the connecting element 9, preferably its axial end and/or the outer edge thereof, in particular such that a liquid- and/or gas-tight connection or sealing S9 is formed between the connecting element 9, preferably its axial end and/or the outer edge thereof, and the adapter/sealing element 48.

In the depicted example, both the closure part 23 and the adapter/sealing element 48 are connected sealingly and/or in press-fit manner with the connecting element 9. With other words, two sealing locations or sealings S5, S9 are established with the connecting element 9: a first one between the lateral side or shell surface of connecting element 9 and the closure part 23 and a second one between the axial end of the connecting element 9 and the adapter/sealing element 48.

Preferably, in this case, when being inserted or received, the connecting element 9 first forms or establishes the sealing S5 with the closure part 23 and after passing through the closure part 23 forms or establishes the sealing S9 with the adapter/sealing element 48.

The sealing S5 is preferably formed or established in the closure part 23 at least essentially at the level where the membrane or sealing wall 33 is located in the delivery state. In other words, the sealing formed by the membrane or sealing wall 33 is preferably replaced by the sealing S5 when the connecting element 9 is inserted into the closure part 23.

Preferably, a (further) sealing S6 is established between the holder 6 and the closure 21, in particular the closure part 23, particularly preferably in the axial and/or radial direction, as already explained above in connection with the first embodiment.

In the following, the membrane or sealing wall 33 according to the fifth embodiment is discussed in further detail. The following explanations, features and advantages can preferably also be implemented independently from the tube 25 and/or adapter/sealing element 48, i.e. they also apply to the cartridge 3 not having tube 25 and/or adapter/sealing element 48. In particular, they can also apply to the membrane or sealing wall 33 according to the fourth embodiment.

The membrane or sealing wall 33 is preferably embodied as a diaphragm or septum. Preferably, the membrane or sealing wall 33 is integrated in and/or arranged within the closure 21, in particular closure part 23 or opening 23D, particularly preferably at an end face of the closure 21 or closure part 23 facing away from the top of the cartridge 3.

The membrane or sealing wall 33 preferably forms a seal, in particular sealing the closure 21 or closure part 23 from the fluid 2.

The shape of the membrane or sealing wall 33 preferably corresponds to the connecting element 9, in particular the membrane or sealing wall 33 being at least essentially circular or disc-like and/or having at least essentially a diameter equal to or (slightly) smaller than the outer diameter of the connecting element 9.

Preferably, in the region of the sealing wall 33, the diameter of opening 23D is (slightly) smaller than the outer diameter of the connecting element 9 in order to form/establish a sealing S5 between the closure part 23 and connecting element 9 after the sealing wall 33 has been broken, in particular when the cartridge 3 is connected to the delivery mechanism 5.

In the delivery state, the membrane or sealing wall 33 is preferably integrally formed or formed as one piece with the closure 21 or closure part 23. Particularly preferably, the closure 21 or closure part 23 and the membrane or sealing wall 33 are injection-molded as one piece.

Preferably, the membrane or sealing wall 33 comprises a central or raised portion 33A, a circumferential portion 33B, a connecting portion 33C and/or a film hinge 33D, as best seen in FIG. 21.

The membrane or sealing wall 33 and/or the different portions 33A to 33D of the membrane or sealing wall 33 are preferably formed as one piece, in particular being injection-molded.

The central or raised portion 33A is preferably arranged in the center of the membrane or sealing wall 33 and/or embodied as a thickened portion of the membrane or sealing wall 33. The raised portion 33A is preferably formed as a dome or spherical segment. In particular, the central or raised portion 33A is arranged on the side of the membrane or sealing wall 33 facing away from the top of the cartridge 3.

Particularly preferably, the membrane or sealing wall 33 is at least essentially flat on the side facing the top of the cartridge 3 and/or curved or bulged on the opposite side, in particular due to providing the raised portion 33A on said side.

The circumferential portion 33B preferably connects the membrane or sealing wall 33 with the closure part 23 in the delivery state. In particular, the circumferential portion 33B forms a ring or a section of a ring which integrally connects the membrane or sealing wall 33 with the closure part 23 in the delivery state.

The circumferential portion 33B is preferably arranged along the circumference of the membrane or sealing wall 33, at least in part. In particular, only the section of the circumference of the membrane or sealing wall 33 which comprises the connecting portion 33C and/or film hinge 33D does not comprise the circumferential portion 33B.

The circumferential portion 33B preferably is embodied very thin and/or forms a predetermined breaking point of the membrane or sealing wall 33.

Preferably, the thickness of the circumferential portion 33B is less than 0.1 mm or 0.05 mm.

The connecting portion 33C is preferably formed web-like or formed as a ridge or reinforcing rib. In particular, the connecting portion 33C extends from the center of the membrane or sealing wall 33 and/or the raised portion 33A to the closure part 23. Particularly preferably, the connecting portion 33C forms a bridge or additional connection from the closure part 23 to the center of the membrane or sealing wall 33 or raised portion 33A.

In particular, the membrane or sealing wall 33 is (integrally) connected to the closure part 23 via the connecting portion 33C, preferably in addition to being (integrally) connected via the circumferential portion 33B.

The connecting portion 33C is preferably integrally formed with the raised portion 33A, membrane or sealing wall 33 and/or closure part 23.

Particularly preferably, the connecting portion 33C and/or raised portion 33A is ten times or twenty times thicker than the circumferential portion 33B.

The membrane or sealing wall 33 or connecting portion 33C preferably forms or comprises a film hinge 33D. In particular, the membrane or sealing wall 33 can swing or hinge away by means of said film hinge 33D.

When the cartridge 3 is connected to the delivery mechanism 5 of the nebulizer 1, the connecting element 9 is preferably inserted into the closure part 23, in particular from the top of the cartridge 3.

The connecting element 9 is preferably adapted to break or pierce through the membrane or sealing wall 33.

The opening 23D preferably has a funnel-shaped or tapered portion which aligns or guides the connecting element 9 to the membrane or sealing wall 33. In particular, the connecting element 9 is positioned and/or constructed such that it can pierce or break the membrane or sealing wall 33 in a defined or precise manner.

When the connecting element 9 is pushed onto the membrane

When pushing the connecting element 9 further down, the membrane or sealing wall 33 preferably further tears along the whole circumferential portion 33B and hinges away, preferably while still being connected to the closure part 23 via the film hinge 33D.

The membrane or sealing wall 33 preferably tears along the circumferential portion 33B and tilts aside in a defined manner and/or in a manner reproducible for similarly manufactured cartridges 3 or is adapted thereto. In particular, the force required to break the membrane or sealing wall 33 is at least essentially the same for similarly manufactured cartridges 3.

This preferably ensures that the membrane or sealing wall 33, when the cartridge 3 is connected to the delivery mechanism 5, does not block or affect the connecting element 9, fixed end 25A of the tube 25 and/or the delivery mechanism 5. In particular, the membrane or sealing wall 33 does not tear completely and/or remains connected with the closure part 23 via the film hinge 33D and/or is kept in the pocket 21C.

The closure part 23, in particular its end face, can further comprise a step or cut-out 230 located adjacent to the film hinge 33D, as in particular shown in FIG. 21. The cut-out 230 can form the pocket 21C or a part thereof. In particular, the cut-out 230 makes it possible or easier for the membrane or sealing wall 33 to tilt or hinge aside.

The cartridge 3 according to the fifth embodiment preferably comprises the intermediate container 28 and the outer container 20. The outer container 20 preferably covers the intermediate container 28 and/or closure 21. In particular, the intermediate container 28 and/or closure 21 are arranged within the outer container 20.

Preferably, a top portion 20E of the outer container 20 forms a front side and/or axial end of the cartridge 3. The outer container 20 or its top portion 20E preferably serves as the securing element 30, in particular axially fixing or securing the closure 21, mostly preferred in a sealing and/or form-fitting manner. In particular, the closure 21 is clamped between the top portion 20E of the outer container 20 and the intermediate container 28.

Preferably, the container 20 or its top portion 20E has an opening at the top, in particular for inserting the connecting element 9 into the cartridge 3. In the delivery state, the opening is preferably covered by the cover 21A.

The intermediate container 28 is preferably made of a rigid material, in particular glass, metal or hard plastic, particularly preferably cyclic olefin polymers. The outer container 20 is preferably made of a rigid material, in particular metal, particularly preferably aluminum.

Preferably, the closure 21 is sealed against the intermediate container 28, in particular by (radial) sealing S1, (axial) sealing S7 and/or adapter/sealing element 48.

Preferably, according to the fifth embodiment, the cartridge 3 comprises a further sealing S10 between the closure 21 and the outer container 20. In particular, a gas- and/or liquid tight connection between the closure 21 and outer container 20 is formed.

Particularly preferably, the sealing S10 between the closure 21 and the container 20 is formed by or comprises a sealing member 49.

The sealing S10 or sealing member 49 preferably seals the cartridge 3 in the radial direction.

The sealing member 49 is preferably in the form of a ring, gasket or molded seal. The sealing member 49 is preferably located in a circumferential recess or notch of the closure 21.

The closure 21 and sealing member 49 can also be integrally formed, particularly preferably by two-component injection-molding.

The outer container 20 can have a protrusion or indentation 20F, protruding towards, abutting and/or pressing on the closure 21 and/or sealing member 49, in particular to provide or increase press/tight-fit between container 20 and closure 21 and/or sealing member 49, particularly preferably forming the sealing S10 thereby.

The sealing S10 or sealing member 49 preferably seals the cartridge 3 from the environment. Thus, fluid 2 is prevented from escaping the cartridge 3, even if it has escaped the intermediate container 28, in particular by escaping through the walls of intermediate container 28 by evaporation and/or diffusion. This is in particular relevant if the fluid 2 is an ethanolic formulation which has a higher evaporation and diffusion rate than an aqueous formulation.

Preferably, at least the outer container 20 is at least essentially resistant against evaporation and diffusion. This is in particular achieved by the outer container 20 being made of an appropriate material, in the case of an ethanolic fluid 2 for example metal, in particular aluminum. Thus, even if fluid 2 can escape intermediate container 28, it is trapped within cartridge 3 by the outer container 20, sealing member 49 and/or sealing S10.

Especially preferably, already escaping of the fluid 2 from the intermediate container 28 is prevented.

However, the sealing member 49 or sealing S10 is preferably provided in addition, and/or as a fail-safe, such that no fluid 2 can escape the cartridge 3 or outer container 20, even if it has escaped the intermediate container 28.

Preferably, in addition to the outer container 20, also the intermediate container 28, closure 21, closure part 23 and/or adapter/sealing element 48, is/are at least essentially resistant against evaporation or diffusion. However, in particular parts which do not come into direct contact with the fluid 2 can be made of materials which are less evaporation/diffusion resistant.

Particularly preferably, sealings S1, S7 and/or S10 prevent not only leakage of the fluid 2, but also (long-term) evaporation or diffusion of the fluid 2.

Preferably, the outer container 20 and/or other evaporation or diffusion resistant components and/or sealings of the cartridge 3 also prevent or minimize diffusion in the opposite direction, i.e. diffusion of gas from the environment into the volume 4 or intermediate container 28. This prevents in particular the fluid 2 from being contaminated.

The cartridge 3 is preferably storage-stable and/or can be stored over a longer period of time, in particular more than one, two or three years, without substantial loss and/or contamination of fluid 2.

Individual features, aspects and/or principles described can be realized independently from each other and may also be combined with one another in any combination as desired and may be used particularly in the shown nebulizer 1, but also in similar or different nebulizers/dispensing devices.

Unlike free standing equipment or the like, the proposed nebulizer 1 is preferably designed to be portable and in particular is a mobile hand operated device.

The proposed solution may, however, be used not only in the nebulizer 1 specifically described here, but also in other nebulizers or inhalers or in other devices for the delivery of liquid formulations.

Preferably, the fluid 2 is a liquid, as already mentioned above, especially an aqueous pharmaceutical formulation or an ethanolic pharmaceutical formulation, in particular having polar characteristics.

However, fluid 2 may also contain other pharmaceutical formulation, a suspension or the like, preferably based on water or ethanol.

Preferred ingredients and/or formulations of the preferably medicinal fluid 2 are listed in particular in WO 2009/115200 A1, preferably on pages 25 to 40, or in EP 2 614 848 A1, paragraphs 0040 to 0087, which are incorporated herewith by reference. In particular, these may be aqueous or non-aqueous solutions, mixtures, formulations containing ethanol or free from any solvent or the like.

ALTERNATIVE COMBINATIONS

The present invention relates in particular to any one of the following aspects which can be realized independently or in any combination, also in combination with any aspects above:

| | List of reference numerals: |
|---|---|
| 1 | nebulizer |
| 2 | fluid |
| 3 | cartridge |
| 4 | variable/collapsible volume |
| 5 | delivery mechanism |
| 6 | holder |
| 6A | engagement portion |
| 6B | sealing portion |
| 7 | energy store/drive spring |
| 8 | blocking element |
| 9 | connecting element |
| 10 | non-return valve |
| 11 | pressure chamber |
| 12 | nozzle |
| 13 | mouthpiece |
| 14 | aerosol |
| 15 | air supply opening |
| 16 | upper housing part |
| 17 | inner housing part |
| 18 | lower housing part |
| 19 | housing |
| 19A | piercing element |
| 20 | container/casing |
| 20A | recess |
| 20B | (top) portion |
| 20C | edge |
| 20D | flange |
| 20E | top portion |
| 20F | indentation |
| 21 | closure |
| 21A | (closure) cover |
| 21B | cover portion |
| 21C | pocket |
| 22 | aeration/ventilation |
| 22A | aeration opening |
| 22B | (ventilation) cover |
| 22C | valve |
| 22D | valve member |
| 22E | valve seat |
| 22F | filter |
| 23 | closure part |
| 23A | inner portion |
| 23B | outer portion |
| 23C | neck |
| 23D | opening |
| 23E | first portion |
| 23F | second portion |
| 23G | third portion |
| 23H | tapered portion/surface |
| 23J | sealing element |
| 23K | channel portion |
| 23L | bypass |
| 23M | chamber |
| 23N | sealing portion |
| 23O | cut-out |
| 24 | closure element |

-continued

| | List of reference numerals: |
|---|---|
| 24A | control portion |
| 24B | displacement portion |
| 24C | stop |
| 24D | sealing element |
| 24E | sealing element |
| 24F | sealing element |
| 24G | axial channel |
| 24H | radial channel |
| 24J | socket |
| 24K | slot |
| 25 | tube |
| 25A | fixed end |
| 25B | free end |
| 25C | immersion element |
| 25D | connecting piece |
| 26 | base element |
| 26A | sealing element |
| 27 | filling element |
| 27A | head |
| 27B | pin |
| 27C | (fluid) channel |
| 27D | (air) channel |
| 28 | intermediate container |
| 29 | valve |
| 30 | security element |
| 30A | top portion |
| 30B | side portion |
| 30C | securing portion |
| 30D | central recess |
| 31 | coding element |
| 31A | coding rib |
| 32 | spherical seal |
| 33 | membrane/sealing wall |
| 33A | raised portion |
| 33B | circumferential portion |
| 33C | connecting portion |
| 33D | film hinge |
| 33E | recessed portion |
| 33F | flexing portion |
| 34 | fluid piston |
| 35 | piston seal |
| 36 | base seal |
| 37 | air pump |
| 38 | pump piston |
| 39 | cylinder |
| 40 | pump chamber |
| 41 | air seal |
| 42 | groove |
| 43 | air valve |
| 44 | filter |
| 45 | opening device |
| 46 | opening element |
| 47 | pressure relief means |
| 48 | adapter/sealing element |
| 49 | sealing member |
| A | axis |
| D | axial stroke/distance |
| S1 | sealing (container - closure) |
| S2 | sealing (closure part - sealing part) |
| S3 | sealing (closure part - closure element) |
| S4 | sealing (closure part - closure element) |
| S5 | sealing (connecting element - closure part) |
| S6 | sealing (closure - holder) |
| S7 | sealing (container - closure) |
| S8 | sealing (closure part - spherical seal) |
| S9 | sealing (connecting element - adapter) |
| S10 | sealing (container - closure) |

The invention claimed is:

1. A cartridge (3) for containing a fluid (2) to be nebulized by a nebulizer (1), the cartridge (3) comprising:
a closure (21) with an opening (23D) for receiving a connecting element (9) of the nebulizer (1) for fluidically connecting the cartridge (3) to the nebulizer (1), wherein:

the connecting element (9) includes a rigid capillary tube, sized and shaped to be received into the opening (23D) when the connecting element (9) is moved axially onto the cartridge (3), the closure (21) comprises a moveable closure element (24) forming a valve (29) that is opened when the rigid capillary tube of the connecting element (9) is received in order to provide a fluidic connection of the cartridge (3) or fluid (2) to the connecting element (9), wherein the valve (29) is adapted to stay open as long as the connecting element (9) is held in the closure (21) or opening (23D) thereof, axial movement of the rigid capillary tube against one end of the closure element (24) causes an opposite end of the closure element (24) to move axially into the fluid (2) as the connecting element (9) is received into the opening (23D), such that the opposite end of the closure element (24) displaces a displacement volume of the fluid (2) through an axial channel (24G) within the closure element (24) and into the rigid capillary tube of the connecting element (9), and thereafter to a delivery mechanism (5) of the nebulizer (1), and a size of the displacement volume is at least two doses of the fluid (2) to be nebulized, where one dose of the fluid is defined as an amount of the fluid (2) that is nebulized out to a user upon one actuation of the nebulizer (1) by the user.

2. The cartridge according to claim 1, wherein the closure (21) comprises a closure part (23) holding the movable closure element (24).

3. The cartridge according to claim 2, wherein the closure part (23) is softer or more flexible than the closure element (24).

4. The cartridge according to claim 2, wherein the closure part (23) forms a sealing (S1) with an integrally formed portion (20B) of an outer container (20) of the cartridge (3) as well as a sealing (S5, S6) with the connecting element (9) and/or a holder (6) thereof.

5. The cartridge according to claim 1, wherein a channel portion (23K) of the closure (21) is opened when the connecting element (9) is received, the channel portion (23K) fluidically connecting the cartridge (3) to the connecting element (9).

6. The cartridge according to claim 1, wherein the size of the displacement volume is at least twice a size of one of: (i) 1 µl to 80 µl of the fluid 2, (ii) at least 5 µl, (iii) at least 10 µl, (iv) at least 20 µl, (v) about 15 µl, and (vi) about 50 µl.

7. The cartridge according to claim 1, wherein the cartridge (3) is adapted to be filled with the fluid (2) through the valve (29) or closure element (24), wherein the valve (29) or closure element (24) is adapted to couple in form-fit manner with a filling element (27) so that the valve (29) or closure element (24) can be closed.

8. The cartridge (3) of claim 1, wherein:

the cartridge (3) includes a container (20) containing the fluid (2);

the closure (21) comprises an integrally formed closure part (23) forming a sealing (S1, S7) with an integrally formed portion (20B) of the container (20) of the cartridge (3) as well as a sealing (S5, S6) with the connecting element (9), the cartridge (3) comprises a securing element (30) assisting in the sealing (S1, S7) by securing and urging the closure (21) into the container (20), and the closure part (23) is clamped between the securing element (30) and the container (20) and thereby is pressed onto and into the container (20) by way of the securing element (30).

9. The cartridge according to claim 8, wherein, the sealing (S1, S7) with the closure (21) and the container (20) of the cartridge (3) are made by direct abutment of portions of the closure (21) against the container (20) both in the axial direction and the radial direction of the cartridge (3).

10. The cartridge according to claim 9, wherein the closure (21) or the closure part (23) forms a head of the cartridge (3).

11. The cartridge according to claim 9, wherein the closure (21) or closure part (23) form a sealing against the container (20) of the cartridge (3).

12. The cartridge according to claim 9, wherein the container (20) forms an outer cylindrical shell of the cartridge (3).

13. The cartridge according to claim 9, wherein the container (20) is of one-piece construction with a portion (20B) holding the closure (21).

14. The cartridge according to claim 9, wherein the closure (21) or its closure part (23) comprises a circumferential notch or neck (23C) for engagement with the container (20) and/or forming a sealing (S1) with the container (20).

15. The cartridge according to claim 9, wherein the cartridge (3) comprises a tube (25) for conveying the fluid (2), and wherein at least one of: (i) a fixed end (25A) of the tube (25) is connected to the closure element (24), and a free end (25B) of the tube (25) is configured to be immersed in the fluid (2), and (ii) the tube (25) flexible.

16. The cartridge according to claim 9, wherein the closure (21) or the opening (23D) comprises a first portion (23E) and a second portion (23F) for forming the sealing (S5, S6) at the first and second portion (23E, 23F), respectively, when the connecting element (9) is received.

17. The cartridge according to claim 16, wherein the first portion (23E) is tapered and/or in that the second portion (23F) is substantially cylindrical.

18. The cartridge according to claim 9, wherein the cartridge (3) comprises a variable or collapsible volume (4) for the fluid (2).

19. The cartridge according to claim 8, wherein the securing element (30) secures the closure (21) to the container (20) in the axial direction.

20. The cartridge according to claim 19 wherein the securing element (30) is embodied as a crimp cap.

21. The cartridge according to claim 19, wherein the securing element (30) is formed ring-like and/or comprises a central recess (30D).

22. The cartridge according to claim 19, wherein the securing element (30) of the cartridge (3) comprises a closure cover (21A), covering the closure (21) axially and/or on a front side.

23. The cartridge according to claim 8, wherein the securing element presses the closure part (23) into the container (20) in the axial direction, thereby forming the sealing (S7) between the closure part (23) and outer container (20) in the axial direction.

24. The cartridge according to claim 9, wherein the closure (21) comprises a spherical seal (32) located, preferably press-fitted, within the opening (23D) sealing the opening (23D) initially before receiving the connecting element (9).

25. The cartridge according to claim 9, wherein the closure (21) comprises a sealing wall (33) located within the opening (23D) sealing the opening (23D) initially before receiving the connecting element (9).

26. The cartridge according to claim 25, wherein the sealing wall (33) is formed as one piece with the closure part (23).

27. The cartridge according to claim 25, wherein the sealing wall (33) comprises a film hinge (33D) and a circumferential portion (33B) of reduced thickness, so that the sealing wall (33) tears along the circumferential portion (33B) and tilts aside upon insertion of the connecting element (9).

28. A nebulizer (1) for a fluid (2), comprising:
an insertable cartridge (3) containing the fluid (2) to be nebulized,
a holder (6) for holding the cartridge (3),
a delivery mechanism (5) for delivering and/or pressurizing the fluid (2), and
a connecting element (9) for fluidically connecting the cartridge (3) to the delivery mechanism (5) or a pump thereof, wherein:
the cartridge (3) comprises a container (20) containing the fluid (2) and a closure (21) with an opening (23D) for receiving the connecting element (9) for fluidically connecting the cartridge (3) to the nebulizer (1),
the connecting element (9) includes a rigid capillary tube sized and shaped to be received into the opening (23D) when the connecting element (9) is moved axially onto the cartridge (3),
the closure (21) comprises a moveable closure element (24) forming a valve (29) that is opened when the rigid capillary tube of the connecting element (9) is received in order to provide a fluidic connection of the cartridge (3) or fluid (2) to the connecting element (9), wherein the valve (29) is adapted to stay open as long as the connecting element (9) is held in the closure (21) or opening (23D) thereof,
axial movement of the rigid capillary tube against one end of the closure element (24) causes an opposite end of the closure element (24) to move axially into the fluid (2) as the connecting element (9) is received into the opening (23D), such that the opposite end of the closure element (24) displaces a displacement volume of the fluid (2) through an axial channel (24G) within the closure element (24) and into the rigid capillary tube of the connecting element (9), and thereafter to the delivery mechanism (5), and
a size of the displacement volume is at least two doses of the fluid (2) to be nebulized, where one dose of the fluid is defined as an amount of the fluid (2) that is nebulized out to a user upon one actuation of the nebulizer (1) by the user.

29. The nebulizer according to claim 28, wherein the connecting element (9) is adapted to push the closure element (24) of the closure (21) further into the cartridge (3) to permanently open the cartridge (3) for fluid withdrawal and to displace fluid (2) into the connecting element (9).

30. The nebulizer according to claim 28, wherein the closure (21) comprises an integrally formed closure part (23) forming a sealing (S1) with an integrally formed portion (20B) of an outer container (20) of the cartridge (3) as well as a sealing (S5, S6) with the connecting element (9) and/or a holder (6) thereof.

31. The nebulizer (1) of claim 28, wherein:
the closure (21) comprises an integrally formed closure part (23) forming a sealing (S1, S7) with an integrally formed portion (20B) of the container (20) of the cartridge (3) as well as a sealing (S5, S6) with the connecting element (9),
the cartridge (3) comprises a securing element (30) assisting in the sealing (S1, S7) by securing and urging the closure (21) into the container (20), and
the closure part (23) is clamped between the securing element (30) and the container (20) and thereby is pressed onto and into the container (20) by way of the securing element (30).

32. The nebulizer according to claim 31, wherein the sealing (S1, S7) with the container (20) of the cartridge (3) is made via direct abutment against the container (20) both in an axial direction and a radial direction of the cartridge (3).

33. The nebulizer according to claim 28 wherein the sealing (S1, S7) includes a first sealing (S5) formed between the closure (21) and the connecting element (9) and a second sealing (S6) formed between the closure (21) and the holder (6).

34. The nebulizer according to claim 33, wherein the first sealing (S5) is formed by press fit in radial direction.

35. The nebulizer according to claim 33, wherein the second sealing (S6) is formed by press fit in an at least essentially axial direction.

36. The according to claim 28, wherein the connecting element (9) is constructed as a piercing element.

37. The nebulizer according to claim 28, wherein the connecting element (9) passes through a central recess (30A) of a securing element (30) of the cartridge (3) when the cartridge is inserted into the nebulizer (1).

38. The nebulizer according to claim 28, wherein the connecting element (9) is adapted to push a spherical seal (31) of the closure (21) further into the cartridge (3) to permanently open the cartridge (3) for fluid withdrawal.

39. The nebulizer according to claim 28, wherein the connecting element (9) is adapted to pierce a closure cover (21A) and/or sealing wall (32) of the closure (21) to permanently open the cartridge (3) for fluid withdrawal.

40. A method, comprising:
arranging a cartridge (3) containing a fluid (2) to be nebulized by a nebulizer (1) for nebulizing the fluid (2), where the cartridge (3) comprises a closure (21) with an opening (23D),
fluidically connecting the cartridge (3) to a delivery mechanism (5) of the nebulizer (1), and
inserting a connecting element (9) of the nebulizer (1) into the closure (21) of the cartridge (3) to fluidically connect the cartridge (3) with the delivery mechanism (5) or a pump thereof, where the connecting element (9) includes a rigid capillary tube sized and shaped to be received into the opening (23D) when the connecting element (9) is moved axially onto the cartridge (3), such that:
(i) a moveable closure element (24) of the closure (21) forms a valve (29) that is opened when the rigid capillary tube of the connecting element (9) is received in order to provide a fluidic connection of the cartridge (3) or fluid (2) to the connecting element (9), wherein the valve (29) is adapted to stay open as long as the connecting element (9) is held in the closure (21) or opening (23D) thereof, and
(ii) axial movement of the rigid capillary tube against one end of the closure element (24) causes an opposite end of the closure element (24) to move axially into the fluid (2) as the connecting element (9) is received into the opening (23D), such that the opposite end of the closure element (24) displaces a displacement volume of the fluid (2) through an axial channel (24G) within the closure element (24) and into the rigid capillary tube of the connecting element (9), and thereafter to a delivery mechanism (5) of the nebulizer (1), wherein a size of the displacement volume is at least two doses of the fluid (2) to be nebulized, where one dose of the fluid is defined as an amount of the fluid (2) that is nebulized out to a user upon one actuation of the nebulizer (1) by the user.

41. The method according to claim 40, wherein the connecting element (9) pierces or breaks a cover (21A) of the cartridge (3) when connecting the cartridge (3) to the delivery mechanism (5).

42. The method according to claim 40, wherein the connecting element (9) is passed through a central recess (30A) of a securing element (30) of the cartridge (3) when connecting the cartridge (3) to the delivery mechanism (5).

* * * * *